United States Patent
Perera

(10) Patent No.: US 9,994,915 B2
(45) Date of Patent: Jun. 12, 2018

(54) MIR-211 EXPRESSION AND RELATED PATHWAYS IN HUMAN MELANOMA

(71) Applicant: Sanford-Burnham Medical Research Institute, La Jolla, CA (US)

(72) Inventor: Ranjan Perera, Overland Park, KS (US)

(73) Assignee: SANFORD-BURNHAM MEDICAL RESEARCH INSTITUTE, La Jolla, CA (US)

( * ) Notice: Subject to any disclaimer, the term of this patent is extended or adjusted under 35 U.S.C. 154(b) by 0 days. days.

(21) Appl. No.: 15/130,856

(22) Filed: Apr. 15, 2016

(65) Prior Publication Data

US 2016/0340744 A1   Nov. 24, 2016

Related U.S. Application Data

(63) Continuation of application No. 13/840,648, filed on Mar. 15, 2013, which is a continuation-in-part of application No. 13/271,030, filed on Oct. 11, 2011.

(60) Provisional application No. 61/442,108, filed on Feb. 11, 2011, provisional application No. 61/391,948, filed on Oct. 11, 2010.

(51) Int. Cl.
| | |
|---|---|
| *C12Q 1/68* | (2018.01) |
| *C12N 15/113* | (2010.01) |
| *A61K 38/17* | (2006.01) |
| *C12N 15/11* | (2006.01) |
| *G01N 33/574* | (2006.01) |

(52) U.S. Cl.
CPC ........ *C12Q 1/6886* (2013.01); *A61K 38/1709* (2013.01); *C12N 15/113* (2013.01); *C12N 15/1138* (2013.01); *G01N 33/5743* (2013.01); *C12N 2310/14* (2013.01); *C12N 2310/141* (2013.01); *C12N 2310/531* (2013.01); *C12N 2320/10* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 4,486,194 A | 12/1984 | Ferrara |
| 4,487,603 A | 12/1984 | Harris |
| 4,925,678 A | 5/1990 | Ranney |
| 4,959,217 A | 9/1990 | Sanders et al. |
| 5,167,616 A | 12/1992 | Haak et al. |
| 5,169,383 A | 12/1992 | Gyory et al. |
| 5,225,182 A | 7/1993 | Sharma |
| 5,898,031 A | 4/1999 | Crooke |
| 6,107,094 A | 8/2000 | Crooke |
| 6,235,310 B1 | 5/2001 | Wang et al. |
| 6,395,713 B1 | 5/2002 | Beigelman et al. |
| 6,586,524 B2 | 7/2003 | Sagara |
| 2002/0130430 A1 | 9/2002 | Castor |
| 2003/0077829 A1 | 4/2003 | MacLachlan |
| 2004/0203145 A1 | 10/2004 | Zamore et al. |
| 2007/0265220 A1 | 11/2007 | Rossi et al. |
| 2007/0292528 A1* | 12/2007 | Bubendorf ........... C12Q 1/6886 424/537 |
| 2009/0311269 A1 | 12/2009 | Allen et al. |

FOREIGN PATENT DOCUMENTS

| | | |
|---|---|---|
| EP | 0 586 520 B1 | 3/1994 |
| EP | 0 618 925 B1 | 10/1994 |
| WO | WO-94/02595 | 2/1994 |
| WO | WO-99/07409 | 2/1999 |
| WO | WO-99/31262 | 6/1999 |
| WO | WO-99/32619 | 7/1999 |
| WO | WO-00/01846 A2 | 1/2000 |
| WO | WO-00/03683 A2 | 1/2000 |
| WO | WO-00/44895 A1 | 8/2000 |
| WO | WO-00/44914 A1 | 8/2000 |
| WO | WO-00/53722 A2 | 9/2000 |
| WO | WO-01/29058 A1 | 4/2001 |
| WO | WO-01/36646 A1 | 5/2001 |
| WO | WO-01/75164 A2 | 10/2001 |
| WO | WO-02/08754 A1 | 1/2002 |
| WO | WO-03/046185 A1 | 6/2003 |
| WO | WO-03/047518 A2 | 6/2003 |
| WO | WO-2006/068232 A1 | 6/2006 |
| WO | WO-2009/099905 A2 | 8/2009 |
| WO | WO-2009/147525 A1 | 12/2009 |

OTHER PUBLICATIONS

Gavrilova-Ruch et al., Effects of imipramine on ion channels and proliferation of IGR1 melanoma cells; Biology, vol. 188, pp. 137-148, 2002.*
de Fougerolles et al., Interfering with disease: a progress report on siRNA-based therapeutics, Nature Reviews, Drug Discovery, vol. 6, pp. 443-453, 2007.*
Adah et al., "Chemistry and biochemistry of 2',5'-Oligoadenylate-Based Antisense Strategy," Curr. Med. Chem., (2001), 8:1189-1212.
Akhtar et al., "Cellular uptake and intracellular fate of antisense oligonucleotides," Trends Cell Bio., (1992), 2:139-144.
Allshire, R., "RNAi and Heterochromatin—a Hushed-Up Affair," Science, (2002), 297:1818-1819.
Aqeilan et al., "miR-15a and MiR-16-1 in cancer: discovery, function and future perspectives," Cell Death and Diff 17:215-220 (2010).
Bass et al., "Double-Stranded RNA as a Template for Gene Silencing," Cell, (2000), 101:235-238.
Bass, B.L., "The short answer," Nature, (2001), 411:428-429.
Bemis et al., "MicroRNA-137 Targets Microphthalmia-Associated Transcription Factor in Melanoma Cell Lines," Cancer Res 68:1362-1368 (2008).

(Continued)

*Primary Examiner* — Addison D Ault
(74) *Attorney, Agent, or Firm* — Foley & Lardner LLP

(57) ABSTRACT

Provided herein are methods for the diagnosis of human melanoma by assessing MITF, miR-211, TRPM1, and/or KCNMA1 and methods for the diagnosis of resistance to chemotherapeutic agents by assessing the regulatory pathways of PGC1α. Methods for treating melanoma, including drug-resistant melanoma, are also provided.

8 Claims, 40 Drawing Sheets

(56) References Cited

OTHER PUBLICATIONS

Bettinger et al., "Size Reduction of Galactosylated PEI/DNA Complexes Improves Lectin-Mediated Gene Transfer into Hepatocytes," Bioconjugate Chem., (1999), 10:558-561.
Bloch et al., "KCNMA1 gene amplification promotes tumor cell proliferation in human prostate cancer," Oncogene 26:2525-2534 (2007).
Carr et al., "Gene-expression profiling in human cutaneous melanoma," Oncogene 22:3076-3080 (2003).
Chen et al., "Complementary analysis of microRNA and mRNA expression during phorbol 12-myristate 13-acetate (TPA)-induced differentiation of HL-60 cells," Biotechnol Lett. 30(12):2045-2052 (2008).
Chen, "MicroRNAs as Oncogenes and Tumor Suppressors," N Engl J Med. 353:1768-1771 (2005).
Choi, et al., "Effect of Poly(ethylene glycol) Grafting on Polyethylenimine as a Gene Transfer Vector in vitro," Bull. Korean Chem. Soc., (2001), 22(1):46-52.
Clemens et al., "The Double-Stranded RNA-Dependent Protein Kinase PKR: Structure and Function," J. Interferon and Cytokine Res., (1997), 17:503-524.
Conry et al., "Phase I Trial of a Recombinant Vaccinia Virus Encoding Carcinoembryonic Antigen in Metastatic Adenocarcinoma: Comparision of Intradermal versus Sucutaneous Administration," Clin. Cancer Res., (1999), 5:2330-2337.
Diebold et al., "Mannose Polyethylenimine Conjugates for Targeted DNA Delivery into Dendritic Cells*," J. Biol. Chem., (1999), 274(27):19087-19094.
Elbashir et al., "Duplexes of 21-nulceotide RNAs mediate RNA interference in cultured mammalian cells," Nature, (2001), 411:494-498.
Elbashir et al., "RNA interference is mediated by 21- and 22-nucleotide RNAs," Genes Dev., (2001), 15:188-200.
Erbacher et al., "Transfection and Physical Properties of Various Saccharide, Poly(ethylene glycol), and Antibody-Derivatized Polyethylenimines (PEI)", J Gene Med., (1999), 1:210-222.
Felicetti et al., "Caveolin-1 tumor-promoting role in human melanoma," Int J Cancer, 125(7):1514-1522 (2009).
Felicetti et al., "MicroRNA-221 and -222 pathway controls melanoma progression." Expert Rev Anticancer Ther. 8(11):1759-1765 (2008).
Felicetti et al., "The Promyelocytic Leukemia Zinc Finger-MicroRNA-221/222 Pathway Controls Melanoma Progression through Multiple Oncogenic Mechanisms," Cancer Res., 68(8):2745-2754 (2008).
Fire et al., "Potent and specific genetic interference by double-stranded RNA in Caenorhabditis elegans," Nature, (1998), 391:806-811.
Fire, A., "RNA-triggered gene silencing," Trends Genet., (1999), 15(9):358-363.
Furgeson et al., "Modified Linear Polyethylenimine—Cholesterol Conjugates for DNA Complexation," Bioconjugate Chem., (2003), 14:840-847.
Gaur et al., "Characterization of MicroRNA Expression Levels and Their Biological Correlates in Human Cancer Cell Lines," Cancer Res., 67(6):2456-2468 (2007).
Godbey et al., "Poly(ethylenimine) and its role in gene delivery," Journal of Controlled Release,(1999), 60:149-160.
Godbey et al., "Tracking the intracellular path of poly(ethylenimine)/DNA complexes for gene delivery," PNAS, USA, (1999), 96:5177-5181.
Gonzalez et al., "New Class of Polymers for the Delivery of Macromolecular Therapeutics," Bioconjugate Chem., (1999), 10:1068-1074.
Hall et al., "Establishment and maintenance of a heterochromatin domain," Science, (2002), 297:2232-2237.
Hamilton et al., "A species of Small Antisense RNA in Post-transcriptional Gene Silencing in Plants," Science, (1999), 286:950-951.

Hammond et al., "An RNA-directed nuclease mediates post-transcriptional gene silencing in *Drosophila* cells," Nature, (2000), Nature, 404:293-296.
Hofland et al., "Formulation and Delivery of Nucleic Acids," Handbook of Experimental Pharmacology, (1991), 137:165-192.
Hutvagner et al., "A microRNA in a multiple-turnover RNAi enzyme complex," Science, (2002), 297:2056-2060.
Igoucheva et al., "MicroRNA-dependent regulation of cKIT in cutaneous melanoma," Biochem Biophys Res Commun., 379(3):790-794 (2009).
International Search Report and Written Opinion dated Apr. 27, 2012 for PCT Patent Application No. PCT/US2011/055735.
Jenuwein, T., "An RNA-Guided Pathway for the Epigenome," Science, (2002), 297:2215-2218.
Jukic et al., "Microrna profiling analysis of differences between the melanoma of young adults and older adults," J of Transl Med., 8:27 (2010).
Khaitan et al., "Role of KCNMAI gene in breast cancer invasion and metastasis to brain," BMC Cancer, (2009), 9:258.
Kunath et al., "The Structure of PEG-Modified Poly(Ethylene Imines) Influences Biodistribution and Pharmacokinetics of Their Complexes with NF-κB Decoy in Mice," Pharmaceutical Research, (2002), 19(6):810-817.
Lee et al., "Expression of small interfering RNAs targeted against HIV-1 rev transcripts in human cells," Nature Biotechnology, (2002), 19:500-505.
Lee et al., "Modified Liposome Formulations for Cytosolic Delivery of Macromolecules," ASC Syrnp. Ser. (2000), 752:184-192.
Lijambio et al., "A microRNA DNA methylation signature for human cancer metastasis," PNAS 105(36):13556-13561 (2008).
Lin et al., "Policing rouge genes," Nature, (1999), 402:128-129.
Lujambio et al., "Genetic Unmasking of an Epigenetically Silenced microRNA in Human Cancer Cells," Cancer Res., 67(4):1424-1429 (2007).
Lynam-Lennon et al., "The roles of microRNA in cancer and apoptosis," Biol Rev Camb Philos Soc., 84(1):55-71 (2009).
Ma et al., "Profiling and Discovery of Novel miRNAs from Formalin-Fixed, Paraffin-Embedded Melanoma and Nodal Specimens," J Mol Diagnostics, 11(5):420-429 (2009).
Maurer et al., "Lipid-based systems for the intracellular delivery of genetic drugs," Mol. Membr. Biol., (1999), 16:129-140.
Mazar et al., "The Regulation of miRNA-211 Expression and Its Role in Melanoma Cell Invasiveness," PLoS One, 5(11):e13779(1-14)(2010).
McManus et al., "Gene silencing using micro-RNA designed hairpins," RNA, (2002), 8:842-850.
Miller et al., "Transcriptional Regulation of the Melanoma Prognostic Marker Melastatin (TRPM1) by MITF in Melanocytes and Melanoma," Cancer Res., 64:509-516 (2004).
Miyagishi et al., "U6 promoter-driven siRNAs with four uridine 3' overhangs efficiently suppress targeted gene expression in mammalian cells," Nature Biotechnology, (2002), 19:497-500.
Molnar et al., "Changes in miRNA expression in solid tumors: an miRNA profiling in melanomas," Semin Cancer Biol., 18(2):111-122 (2008).
Mueller et al., "miRNA Expression Profiling in Melanocytes and Melanoma Cell Lines Reveals miRNAs Associated with Formation and Progression of Malignant Melanoma," J Invest Dermatol., 129:1740-1751 (2009).
Mueller et al., "Role of miRNAs in the progression of malignant melanoma," Br J Cancer, 101:551-556 (2009).
Novina et al., "siRNA-directed inhibition of HIV-1 infection," Nature Medicine, (2002), 8(7):681-686.
Oancea et al., TRPM1 Forms Ion Channels Associated with Melanin Content in Melanocytes, Sci Signal 2(70):ra21 (2009).
Ogris, et al., "DNA/polyethylenimine transfection particles: Influence of ligands, polymer size, and PEGylation on internalization and gene expression", AAPA PharmSci,(2001), 3(3):1-11.
Paul et al., "Effective expression of small interfering RNA in human cells," Nature Biotechnology, (2002), 19:505-508.
PCT International Search Report and Written Opinion in related PCT Patent Application No. PCT/US11/55735.

(56) References Cited

OTHER PUBLICATIONS

Petersen et al., "Polyethylenimine-graft-Poly(ethylene glycol) Copolymers: Influence of Coploymer Block Structure on DNA Complexation and Biological Activites as Gene Delivery System," Bioconjugate Chem., (2002), 13:845-854.

Philippidou et al., "Signatures of MicroRNAs and Selected MicroRNA Target Genes in Human Melanoma," Cancer Res., 70(10):4163-4173 (2010).

Reinhart et al., "MicroRNAs in plants," Gene. & Dev., (2002), 16:1616-1626.

Reinhart et al., "Small RNAs correspond to centromere heterochromatic repeats," Science, (2002), 297:1831.

Sato et al., "Resolution of liver cirrhosis using vitamin A-coupled liposomes to deliver siRNA against a collagen-specific chaperone," Nature Biotechnol., (2008), 26(4):431-442.

Schmittgen T., "Regulation of microRNA processing in development, differentiation and cancer," J Cell Mol Med., 12(5B):1811-1819 (2008).

Schultz et al., "MicroRNA let-7b targets important cell cycle molecules in malignant melanoma cells and interferes with anchorage-independent growth," Cell Res., (2008), 18:549-557.

Segura et al., "Aberrant miR-182 expression promotes melanoma metastasis by repressing FOXO3 and microphthalmia-associated transcription factor," PNAS, 106(6):1814-1819 (2009).

Sharp, P.A., "RNAi and double-stranded RNA," Genes & Dev., (1999), 13:139-141.

Shenouda et al., MicroRNA function in cancer: oncogene or a tumor suppressor? Cancer Metastasis Rev. 28:369-378 (2009).

Shoag et al., "PGC-1 Coactivators Regulate NITF and the Tanning Response," Molecular Cell, (2013), 49:145-157.

Strauss, E., "Candidate 'Gene Silencers' Found," Science, (1999), 286(5441):886.

Thomas et al., "Enhancing polyethylenimine's delivery of plasmid DNA into mammalian cells," PNAS, (2002), 99(23): 14640-14645.

Volpe et al., "Regulation of heterochromatic silencing and histone H3 lysine-9 methylation by RNAi," Science, (2002), 297:1833-1837.

Wang et al., "MicroRNA-204/211 alters epithelial physiology," FASEB, (2010), 24(5):1552-1571.

Zamore et al., "RNAi: Double-Stranded RNA Directs the ATP-Dependent Cleavage of mRNA at 21 to 23 Nucleotide Intervals," Cell, (2000), 101:25-33.

\* cited by examiner

FIG. 13A

TRPM1 Promoters (MC, SKMEL28, A375, WM1552C – Final).apr

```
                                              Section 1
                                    10        20        30        40        50        60        70        79
Melanocytes TRPM1 promoter    (1) TAGATCTCTCAGATGCTGGGAAGACCCAGCCCCTGCAGAGAGGAATAGTTCAGGGTTTTTTTTTTCTTTCCTCC
SKMEL-28 TRPM1 promoter       (1) TAGATCTCTCAGATGCTGGGAAGACCCAGCCCCTGCAGAGAGGAATAGTTCAGGGTTTTTTTTTTCTTTCCTCC
A375 TRPM1 promoter           (1) TAGATCTCTCAGATGCTGGGAAGACCCAGCCCCTGCAGAGAGGAATAGTTCAGGGTTTTTTTTTCTTTCCTCC
WM1552C TRPM1 promoter        (1) TAGATCTCTCAGATGCTGGGAAGACCCAGCCCCTGCAGAGAGGAATAGTTCAGGGTTTTTTTTTCTTTCCTCC Section 2
                                    90       100       110       120       130       140       150      158
Melanocytes TRPM1 promoter   (80) TGGGCTTGAGAAAGCTCATGGAAAGCTGGAATAACCACGCATACTGTTACAGCAAATCAACACAGCTCCCACCGGGTG
SKMEL-28 TRPM1 promoter      (80) TGGGCTGAGAAAGCTCATGGAAAGCTGGAATAACCACGCATACTGTTACAGCAAATCAACAGACTCCCACCGGGTG
A375 TRPM1 promoter          (80) TGGGCTGAGAAAGCTCATGGAAAGCTGGAATAACCACGCATACTGTTACAGCAAATCAACAGACTCCCACCGGGTG
WM1552C TRPM1 promoter       (80) TGGGCTGAGAAAGCTCATGGAAAGCTGGAATAACCACGCATACTGTTACAGCAAATCAACAGACTCCCACCATGGTG Section 3
                                   170       180       190       200       210       220       230      237
Melanocytes TRPM1 promoter  (159) GTTTTCAGGTGACTGTGGATGCCAAGCAGGCAAGCTCCTGGTGAAGGGGAGAGCAGGATTAGAAGCACTCAGAAGG
SKMEL-28 TRPM1 promoter     (159) GTTTTCAGGTGACTGTGGATGCCAAGCAGGCAAGCTCCTGGTGAAGGGGAGAGCAGGATTAGAAGCACTCAGAAGG
A375 TRPM1 promoter         (159) GTTTTCAGGTGACTGTGGATGCCAAGCAGGCAAGCTCCTGGTGAAGGGGAGAGCAGGATTAGAAGCACTCAGAAGG
WM1552C TRPM1 promoter      (159) GTTTTCAGGTGACTGTGGATGCCAAGCAGGCAAGCTCCTGGTGAAGGGGAGAGCAGGATTAGAAGCACTCAGAAGG Section 4
                                   250       260       270       280       290       300       310      316
Melanocytes TRPM1 promoter  (238) GGCTGAGAGTCATGTGGGCTCACACTGCATTTGCAGCTGGTTCACCTGACCTCAGGCCCCAACTTAGATGAGGAAGG
SKMEL-28 TRPM1 promoter     (238) GGCTGAGAGTCATGTGGGCTCACACTGCATTTGCAGCTGGTTCACCTGACCTCAGGCCCCAACTTAGATGAGGAAGG
A375 TRPM1 promoter         (238) GGCTGAGAGTCATGTGGGCTCACACTGCATTTGCAGCTGGTTCACCTGACCTCAGGCCCCAACTTAGATGAGGAAGG
WM1552C TRPM1 promoter      (238) GGCTGAGAGTCATGTGGGCTCACACTGCATTTGCAGCTGGTTCACCTGACCTCAGGCCCCAACTTAGATGAGGAAGG Section 5
                                   330       340       350       360       370       380       390     395
Melanocytes TRPM1 promoter  (317) ATTAGCAGTAATTAATGCCATGTGCCGCTTCTCCCAGCTCCCCGGGCCACGAACACTGCCCAGCTGATGAGGGATTC
SKMEL-28 TRPM1 promoter     (317) ATTAGCAGTAATTAATGCCATGTGCCGCTTCTCCCAGCTCCCCGGGCCACGAACACTGCCCAGCTGATGAGGGATTC
A375 TRPM1 promoter         (317) ATTAGCAGTAATTAATGCCATGTGCCGCTTCTCCCAGCTCCCCGGGCCACGAACACTGCCCAGCTGATGAGGGATTC
WM1552C TRPM1 promoter      (317) ATTAGCAGTAATTAATGCCATGTGCCGCTTCTCCCAGCTCCCCGGGCCACGAACACTGCCCAGCTGATGAGGGATTC
```

|                              |       | 410        | 420        | 430        | 440        | 450        | 460        | Section 6 474 |
|------------------------------|-------|------------|------------|------------|------------|------------|------------|---------------|
| Melanocytes TRPM1 promoter   | (396) | TGAAAGAACCATTATGTCCAATTATGTCTCAATTATGCAAACCCTGCTGACATTTCCAGCCAGGAAGGCGGCTGGGTGG |
| SKMEL-28 TRPM1 promoter      | (396) | TGAAAGAACCATTATGTCCAATTATGTCTCAATTATGCAAACCCTGCTGACATTTCCAGCCAGGAAGGCGGCTGGGTGG |
| A375 TRPM1 promoter          | (396) | TGAAAGAACCATTATGTCCAATTATGTCTCAATTATGCAAACCCTGCTGACATTTCCAGCCAGGAAGGCGGCTGGGTGG |
| WM1552C TRPM1 promoter       | (396) | TGAAAGAACCATTATGTCCAATTATGTCTCAATTATGCAAACCCTGCTGACATTTCCAGCCAGGAAGGCGGCTGGGTGG |

Section 7 553

|                              |       | 480        | 490        | 500        | 510        | 520        | 530        | 540        |
|------------------------------|-------|------------|------------|------------|------------|------------|------------|------------|
| Melanocytes TRPM1 promoter   | (475) | GAGGGGGCCATGGGGGGCCACTTCAAAGGAAAAAGCTCTAGCTCCCTACCTCTCACATCCTAAGGCTGCCTTTGTG |
| SKMEL-28 TRPM1 promoter      | (475) | GAGGGGGCCATGGGGGGCCACTTCAAAGGAAAAAGCTCTAGCTCCCTACCTCTCACATCCTAAGGCTGCCTTTGTG |
| A375 TRPM1 promoter          | (475) | GAGGGGGCCATGGGGGGCCACTTCAAAGGAAAAAGCTCTAGCTCCCTACCTCTCACATCCTAAGGCTGCCTTTGTG |
| WM1552C TRPM1 promoter       | (475) | GAGGGGGCCATGGGGGGCCACTTCAAAGGAAAAAGCTCTAGCTCCCTACCTCTCACATCCTAAGGCTGCCTTTGTG |

Section 8 632

|                              |       | 560        | 570        | 580        | 590        | 600        | 610        | 620        |
|------------------------------|-------|------------|------------|------------|------------|------------|------------|------------|
| Melanocytes TRPM1 promoter   | (554) | GGATTCCACACAGAACAGCCTGGAAGCTTGGGGCCCTGGCTTCCTTTCTGGCCTGGGAGTCAGTCAGTCATGGGCCATCG |
| SKMEL-28 TRPM1 promoter      | (554) | GGATTCCACACAGAACAGCCTGGAAGCTTGGGGCCCTGGCTTCCTTTCTGGCCTGGGAGTCAGTCAGTCATGGGCCATCG |
| A375 TRPM1 promoter          | (554) | GGATTCCACACAGAACAGCCTGGAAGCTTGGGGCCCTGGCTTCCTTTCTGGCCTGGGAGTCAGTCAGTCATGGGCCATCG |
| WM1552C TRPM1 promoter       | (554) | GGATTCCACACAGAACAGCCTGGAAGCTTGGGGCCCTGGCTTCCTTTCTGGCCTGGGAGTCAGTCAGTCATGGGCCATCG |

Section 9 711

|                              |       | 640        | 650        | 660        | 670        | 680        | 690        | 700        |
|------------------------------|-------|------------|------------|------------|------------|------------|------------|------------|
| Melanocytes TRPM1 promoter   | (633) | CTTCACAGCAATCATGAGGGCCCAGGCCCAAGTGCTCCTCCTCATGGGGACTGCTGCTCCTCTTAAAGGGTGGCCC |
| SKMEL-28 TRPM1 promoter      | (633) | CTTCACAGCAATCATGAGGGCCCAGGCCCAAGTGCTCCTCCTCATGGGGACTGCTGCTCCTCTTAAAGGGTGGCCC |
| A375 TRPM1 promoter          | (633) | CTTCACAGCAATCATGAGGGCCCAGGCCCAAGTGCTCCTCCTCATGGGGACTGCTGCTCCTCTTAAAGGGTGGACCC |
| WM1552C TRPM1 promoter       | (633) | CTTCACAGCAATCATGAGGGCCCAGGCCCAAGTGCTCCTCCTCATGGGGACTGCTGCTCCTCTTAAAGGGTGGACCC |

Section 10

|                              |       | 720        | 730        | 749        |
|------------------------------|-------|------------|------------|------------|
| Melanocytes TRPM1 promoter   | (712) | TCCTCACCCAGCTCCTGCCCTGCCCAAGGAGCTAGCT |
| SKMEL-28 TRPM1 promoter      | (712) | TCCTCACCCAGCTCCTGCCCTGCCCAAGGAGCTAGCT |
| A375 TRPM1 promoter          | (712) | TCCTCACCCAGCCCCTGCCCTGCCCAAGGAGCTAGCT |
| WM1552C TRPM1 promoter       | (712) | TCCTCACCCAGCCCCTGCCCTGCCCAAGGAGCTAGCT |

FIG. 13B

```
   1 tgatgcgtcc ccccccaacc tttccctcac ccctcccac cccagcccc gactccagcc
  61 agcgcctccc tccacccag gacgccactc atttcatctc atttaaggga aaatatata
 121 tctatctatt tgaggaaact gaggacctcg gaatctctag caagggctca acttcgaaaa
 181 tggcaacaac agagatgcaa aaagctaaaa agacacccc cccctttaaa tggttttctt
 241 tttgaggcaa gttggatgaa cagagaaggg aagagaggaa gaacgagagg aagagaaggg
 301 aaggaagtgt ttgtgtagaa gagagagaaa gacgaataga gttaggaaaa ggaagacaag
 361 caggtgggca ggaaggacat gcaccgagac caggcagggg cccaactttc acgtccagcc
 421 ctggcctggg gtcgggagag gtgggcgcta gaagatgcag cccaggatgt ggcaatcaat
 481 gacactattg gggtttccca ggatggattg gtcagggga gaaaggaaaa ggcaaaacac
 541 tccaggacct ctcccggatc tgtctcctcc tctagccagc agtatggaca gctggacccc
 601 tgaacttcct ctcctcttac ctgggcagag tgttgtctct cccaaattt ataaaaacta
 661 aaatgcattc cattcctctg aaagcaaaac aaattcataa ttgagtgata taaatagag
 721 aggttttcgg aagcagatct gtgaatatga aatacatgtg catatttcat tcccaggca
 781 gacatttttt agaaatcaat acatgcccca atattggaaa gacttgttct tccacggtga
 841 ctacagtaca tgctgaagcg tgccgtttca gccctcattt aattcaattt gtaagtagcg
 901 cagcagcctc tgtggggag gataggctga aaaaaaaaag tgggctcgta tttatctaca
 961 ggactccata tagtcatata taggcatata aatctattct ttttcttgt tttttcttt
1021 cttcctttct ttcaaaggtt tgcattaact tttcaaagta gttcctatag gggcattgag
1081 gagcttcctc attctgggaa aactgagaaa acccatattc tcctaataca acccgtaata
1141 gcatttttgc ctgcctcgag gcagagtttc ccgtgagcaa taaactcagc tttttgtgg
1201 ggcacagtac tggatttgac agtgattccc cacgtgtgtt catctgcacc caccgagcca
1261 ggcagaggcc agccctccgt ggtgcacaca gcacgcgcct cagtccatcc cattttagtc
1321 tttaaaccct caggaagtca cagtctccgg acaccacacc acatgagccc aacaggtcca
1381 cgatggatcc accagtccca ccccagcctt ttcctttcat ctgaacagaa tgtgcatttt
1441 tggaagcctc cctcactctc catgctggca gagcaggagg gagactgaag taagagatgg
1501 cagagggaga tggtggcaaa aaggtttaga tgcaggagaa cagtaagatg gatggttccg
1561 gccagagtcg atgtggggag gaacagaggg ctgaagggag aggggctga ctgttccatt
1621 ctagctttgg cacaaagcag cagaaagggg gaaaagccaa tagaaattc cttagcttcc
1681 ccaccatatg tatttctag gatttgagag gaaagagagg aaaatggggg aatgggttgc
1741 aaaatagaaa tgagcttaat ccaggccgca gagccaggga aggtgagtaa ctttaggagg
1801 gtgctagact ttagaaggca gataggaaga atcagtctaa actggccatg ctttggaagg
1861 gacaagacta tgtgctccgc tgcccaccct cagcctgcaa tgaggggactg aggccacga
1921 gtctttccag ctcttcctcc attctggcca gtccctgcat cctccctggg gtggaggatg
1981 gaaggaaagc tgggacaagc agggaacgca tgattcaggg atgctgtcac tcggcagcca
2041 gattccgaaa ctcccattct ccaatgactt cctcaaccaa tgggtggcct tgtgactgtt
2101 ctttaaggct gaagatatcc aggaagggg gcttggacac tggccaagga gacccttcg
2161 tgctgtggac acagctctct tcactctttg ctcatggcat gacacagcgg agaccgcctc
2221 caacaacgaa tttggggcta cgaagaggaa tagcgaaaaa gcaaatctgt ttcaactgat
2281 gggaaccta tagctataga acttggggc tatctcctat gcccctggac aggacagttg
2341 gctggggaca ggagaagtgc tcaatcttca tgagacaaag gggcccgata gggccagcag
2401 ccacaaggcc ttgacctgcc gagtcagcat gcccatctc tctgcacagc tgtccctaa
2461 acccaactca cgttctgta tgtcttaggc cagtatccca aacctcttcc acgtcactgt
2521 tctttccacc cattctccct ttgcatcttg agcagttatc caactaggat ctgccaagtg
2581 gatactgggg tgccactccc ctgagaaaag actgagccag gaactacaag ctcccccac
2641 attcctccca gcctgacct aattcttgag aggggctctc tcttcacgga ctgtgtctgg
2701 actttgagca ggcttctgcc ccttgcgttg gctctttgct gccagccatc aggtgggga
2761 ttagagcctg gtgtaagtgc gccagactct tccggtttcc aaagttcgtg cctgcgaacc
2821 caaacctgtg agtctcttct gcatgcagga gtttctcctg ggcagctggt cactccccag
```

FIG. 26A

```
2881  agaagctggg  ccttcatgga  cacatggaac  taagcctccc  aaatgggagt  tctggctgag
2941  cccagggtgg  ggagatcctg  ggaagggagg  cactggagga  agacggcacc  tcttccccca
3001  tggcagggtg  tgagggaggc  aggtttggaa  tggtgcgagt  atgcaatct   aagcagggt
3061  ctggtctctt  tgactccagg  ctggcctttg  gccgactgtc  tgctcaccca  gagacttgg
3121  actccggact  atccatggct  ccgaatctaa  gtgctgccca  ctccatgct   cacaccaca
3181  gaaggtcttc  ccatccoctt  tagattcgtg  cctcactcca  ccagtgagga  agatgcctct
3241  gtctttccca  cgactgccag  gagatagqga  agcccagcca  ggactgaccc  tccttcctcc
3301  agcctgccct  gacccacctg  gcaaagcagg  gcacatgggg  aggaagagac  tggaaccttt
3361  ctttgacagc  caggcctaga  cagacaggcc  tggggacact  ggccccatga  ggggaggaag
3421  gcaggcgcac  gaggtccagg  gaggcccttt  tctgatcatg  cccttctct   cccacccat
3481  ctccccacca  ccacctctgt  ggcctccatg  gtaccccac   agggctggcc  tccctagag
3541  ggtgggcctc  aaccacctgc  tcccgccacg  caccggttag  tgagacaggg  ctgccacggc
3601  aaccgccaag  cccccctcaa  ggtgggacag  taccccggac  ccatccactc  actcctgaga
3661  gggctccggc  ccagaatggg  aacctcagag  aagagctcta  aggagaagaa  accccatagc
3721  gtcagagagg  atatgtctgg  cttccaagag  aaaggaggct  ccgtttgca   aagtggagga
3781  gggacgaggg  acagggtttt  caccagccag  caacctgggc  cttgtactgt  ctgtgttttt
3841  aaaaccacta  aagtgcaaga  attcattgc   actgtttctc  cacttttat   tttctcttag
3901  gcttttgttt  ctatttcaaa  catactttct  tggttttcta  atggagtata  tagtttagtc
3961  atttcacaga  ctctggcctc  ctctcctgaa  atcctttgg   atggggaaag  ggaggtggg
4021  gagggtccga  ggggaagggg  accccagctt  ccctgtgccc  gctcacccca  ctccaccagt
4081  cccccgtcgc  cagccggagt  ctcctctcta  ccgccactgt  cacaccgtag  cccacatgga
4141  tagcacagtt  gtcagacaag  attccttcag  attccgagtt  gcctaccggt  tgttttcgtt
4201  gttgttgttg  ttgtttttct  ttttcttttt  tttttgaag   acagcaataa  ccacagtaca
4261  tattactgta  gtctctata   gttttacata  cattcatacc  ataactctgt  tctctcctct
4321  ttttgtttt   caactttaaa  aacaaaaata  aacgatgata  atctttactg  gtgaaaagga
4381  tggaaaaata  aatcaacaaa  tgcaaccagt  ttgtgagaaa  aaaaaaaaaa  agccgaaaaa
4441  aaaaaaaaaa  acacctgaat  gcggaagagc  tcggctcccg  tttagcattt  tgtacttaag
4501  gaaataaaaa  accaacaaag  gatctcacat  tttcttaaaa  agtgaagatt  gctgtatact
4561  atttattcaa  cttataattt  atgttactcc  ttgatctttg  tctttgtca   tgacaaagca
4621  tttatttaat  aaagttatgc  attcagtt
```

(SEQ ID NO: 41)

FIG. 26B

SEQUENCE LISTING

```
<160> NUMBER OF SEQ ID NOS: 42

<210> SEQ ID NO 1
<211> LENGTH: 22
<212> TYPE: RNA
<213> ORGANISM: Homo sapiens

<400> SEQUENCE: 1
ugagguagua gguuguauag uu                                                 22

<210> SEQ ID NO 2
<211> LENGTH: 22
<212> TYPE: RNA
<213> ORGANISM: Homo sapiens

<400> SEQUENCE: 2
ugagguagua gguugugugg uu                                                 22

<210> SEQ ID NO 3
<211> LENGTH: 22
<212> TYPE: RNA
<213> ORGANISM: Homo sapiens

<400> SEQUENCE: 3
ugagguagua gguuguaugg uu                                                 22

<210> SEQ ID NO 4
<211> LENGTH: 22
<212> TYPE: RNA
<213> ORGANISM: Homo sapiens

<400> SEQUENCE: 4
```
agagguagua gguugcauag uu                                              22

<210> SEQ ID NO 5
<211> LENGTH: 22
<212> TYPE: RNA
<213> ORGANISM: Homo sapiens

<400> SEQUENCE: 5
ugagguagga gguuguauag uu                                              22

<210> SEQ ID NO 6
<211> LENGTH: 22
<212> TYPE: RNA
<213> ORGANISM: Homo sapiens

<400> SEQUENCE: 6
ugagguagua gauuguauag uu                                              22

<210> SEQ ID NO 7
<211> LENGTH: 22
<212> TYPE: RNA
<213> ORGANISM: Homo sapiens

<400> SEQUENCE: 7
ugagguagua guuuguacag uu                                              22

<210> SEQ ID NO 8
<211> LENGTH: 22
<212> TYPE: RNA
<213> ORGANISM: Homo sapiens

<400> SEQUENCE: 8
ugagguagua guuugugcug uu                                              22

<210> SEQ ID NO 9
<211> LENGTH: 24
<212> TYPE: RNA
<213> ORGANISM: Homo sapiens

<400> SEQUENCE: 9
ucccugagac ccuuuaaccu guga                                            24

<210> SEQ ID NO 10
<211> LENGTH: 22
<212> TYPE: RNA
<213> ORGANISM: Homo sapiens

<400> SEQUENCE: 10
ucccugagac ccuaacuugu ga                                              22

<210> SEQ ID NO 11
<211> LENGTH: 22
<212> TYPE: RNA
<213> ORGANISM: Homo sapiens

<400> SEQUENCE: 11
uagcagcaca ucaugguuua ca                                              22

<210> SEQ ID NO 12
<211> LENGTH: 22
<212> TYPE: RNA
<213> ORGANISM: Homo sapiens

<400> SEQUENCE: 12

-continued uagcagcacg uaaauauugg cg                                              22

<210> SEQ ID NO 13
<211> LENGTH: 23
<212> TYPE: RNA
<213> ORGANISM: Homo sapiens

<400> SEQUENCE: 13
cccaguguuc agacuaccug uuc                                             23

<210> SEQ ID NO 14
<211> LENGTH: 22
<212> TYPE: RNA
<213> ORGANISM: Homo sapiens

<400> SEQUENCE: 14
uagcuuauca gacugauguu ga                                              22

<210> SEQ ID NO 15
<211> LENGTH: 22
<212> TYPE: RNA
<213> ORGANISM: Homo sapiens

<400> SEQUENCE: 15
uucccuuugu cauccuucgc cu                                              22

<210> SEQ ID NO 16
<211> LENGTH: 22
<212> TYPE: RNA
<213> ORGANISM: Homo sapiens

<400> SEQUENCE: 16
acagcaggca cagacaggca gu                                              22

<210> SEQ ID NO 17
<211> LENGTH: 23
<212> TYPE: RNA
<213> ORGANISM: Homo sapiens

<400> SEQUENCE: 17
agcuacauug ucugcugggu uuc                                             23

<210> SEQ ID NO 18
<211> LENGTH: 21
<212> TYPE: RNA
<213> ORGANISM: Homo sapiens

<400> SEQUENCE: 18
agcuacaucu ggcuacuggg u                                               21

<210> SEQ ID NO 19
<211> LENGTH: 21
<212> TYPE: RNA
<213> ORGANISM: Homo sapiens

<400> SEQUENCE: 19
aucacauugc cagggauuuc c                                               21

<210> SEQ ID NO 20
<211> LENGTH: 21
<212> TYPE: RNA
<213> ORGANISM: Homo sapiens

<400> SEQUENCE: 20
aucacauugc cagggauuac c                                      21

<210> SEQ ID NO 21
<211> LENGTH: 22
<212> TYPE: RNA
<213> ORGANISM: Homo sapiens

<400> SEQUENCE: 21
ccuauucuug guuacuugca cg                                     22

<210> SEQ ID NO 22
<211> LENGTH: 23
<212> TYPE: RNA
<213> ORGANISM: Homo sapiens

<400> SEQUENCE: 22
uguaaacauc cuacacucuc agc                                    23

<210> SEQ ID NO 23
<211> LENGTH: 22
<212> TYPE: RNA
<213> ORGANISM: Homo sapiens

<400> SEQUENCE: 23
aaaagcuggg uugagagggc ga                                     22

<210> SEQ ID NO 24
<211> LENGTH: 22
<212> TYPE: RNA
<213> ORGANISM: Homo sapiens

<400> SEQUENCE: 24
aacccguaga uccgaucuug ug                                     22

<210> SEQ ID NO 25
<211> LENGTH: 47
<212> TYPE: DNA
<213> ORGANISM: Homo sapiens

<400> SEQUENCE: 25
accacaatta attgtaatta agggaaatga attattaaaa caatttt          47

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
accacaatta attgtaattt acgcatatga attattaaaa caatttt          47

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttcccttTGT catccttcgc ct                                     22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aggcgaagga tgacaaaggg aa                                            22

<210> SEQ ID NO 29
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgtacttcaa tgacaatatt tcaagagaat attgtcattg aagtacgtct ttttt        55

<210> SEQ ID NO 30
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aaaaaagacg tacttcaatg acaatattct cttgaaatat tgtcattgaa gtacg        55

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgcggccgcc ttccctatat ctaaacaatg caaaatc                            37

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaccggtcac ccatccaggc gaggagc                                       27

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tacgcatatg aattattaaa acaatttt                                      28

```
<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tatgcgtaaa ttacaattaa ttgtgct                                          27

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gctcacatgt                                                             10

<210> SEQ ID NO 36
<211> LENGTH: 749
<212> TYPE: DNA
<213> ORGANISM: Homo sapiens

<400> SEQUENCE: 36
tagatctctc agatgctggg aagacccag ccctctgca gagagggata gttcagggtt        60
tgggtttttt ctttcctcct gggctgagaa agctcatgga aagctggaat aaccacgcat    120
actgttacag caaatccaac agagctccca ccgtggtggt tttcaggtga ctgtggatgc    180
caagcaggca agctcctggt gaaggggga gagcagggat tagaagcact cagaaggggc    240
tgagagtcat gtggggctca cactgcattt gcagctgggt tcaccctgac ctcaggccca    300
acttagatga ggaaggatta gcagtaatta gtgccatgtg ccgccttctc ccagctcccc    360
ggggcacgaa cactgcccag ctgatgaggg gattctgaaa gaaccattat gtccaattgt    420
ctcaattatg caaaccctgc tgacatttcc agccagggaa gggcggctgg gtgggagggg    480
gccatggcgg ggccacttca aaggaaaagc tctagctccc ctacctctct cacatcctaa    540
ggctgccttt gtgggattcc acacagaaca gcctggaagc ttggggcct ggcttccttt    600 tctggcctgg gagtcaggtc atggggccat cgcttcacag caatcatgag ggcccaggcc    660
caagtgctca catgctcctc atggggactg ctcctcttaa agggtgggcc ctcctcaccc    720
agctccctgc cctggccaag gagctagct                                      749

<210> SEQ ID NO 37
<211> LENGTH: 749
<212> TYPE: DNA
<213> ORGANISM: Homo sapiens

<400> SEQUENCE: 37
tagatctctc agatgctggg aagacccag ccctctgca gagagggata gttcagggtt        60
tgggtttttt ctttcctcct gggctgagaa agctcatgga aagctggaat aaccacgcat    120
actgttacag caaatccaac agagctccca ccgtggtggt tttcaggtga ctgtggatgc    180
caagcaggca agctcctggt gaaggggga gagcagggat tagaagcact cagaaggggc    240
tgagagtcat gtggggctca cactgcattt gcagctgggt tcaccctgac ctcaggccca    300
acttagatga ggaaggatta gcagtaatta gtgccatgtg ccgccttctc ccagctcccc    360
```

```
ggggcacgaa cactgcccag ctgatgaggg gattctgaaa gaaccattat gtccaattgt    420
ctcaattatg caaaccctgc tgacatttcc agccagggaa gggcggctgg gtgggagggg    480
gccatggcgg ggccacttca aaggaaaagc tctagctccc ctacctctct cacatcctaa    540
ggctgccttt gtggaggggg ccatggcggg gccacttcaa aggaaaagct ctagctcccc    600
tacctctctc acatcctaag gctgcctttg tgcttcacag caatcatgag ggcccaggcc    660
caagtgctca catgctcctc atggggactg ctcctcttaa agggtgggcc ctcctcaccc    720
agctccctgc cctggccaag gagctagct                                      749
```

<210> SEQ ID NO 38
<211> LENGTH: 749
<212> TYPE: DNA
<213> ORGANISM: Homo sapiens

<400> SEQUENCE: 38

```
tagatctctc agatgctggg gaagacccag cccctctgca gagagggata gttcagggtt     60
tgggtttttt ctttcctcct gggctgagaa agctcatgga aagctggaat aaccatgcat    120
actgttacag caaatccaac agagctccca ccgtggtggt tttcaggtga ctgtggatgc    180
caagcaggca agctcctggt gaaggggga gagcagggat tagaagcact cagaagggc      240 tgagagtcat gtggggctca cactgcattt gcagctgggt tcaccctgac ctcaggccca    300
acttagatga ggaaggatta gcagtaatta atgccatgtg ccgccttctc ccagctcccc    360
ggggcacgaa cactgcccag ctgatgaggg gattctgaaa gaaccattat gtccaattgt    420
ctcaattatg caaaccctgc tgacatttcc agccagggaa gggcggctgg gtgggagggg    480
gccatggcgg ggccacttca aaggaaaagc tctagctccc ctacctctct cacatcctaa    540
ggctgccttt gtggaggggg ccatggcggg gccacttcaa aggaaaagct ctagctcccc    600
tacctctctc acatcctaag gctgcctttg tgcttcacag caatcatgag ggcccaggcc    660
caagtgctca catgctcctc atggggactg ctcctcttaa agggtgggcc ctcctcaccc    720
agctccctgc cctggccaag gagctagct                                      749
```

<210> SEQ ID NO 39
<211> LENGTH: 749
<212> TYPE: DNA
<213> ORGANISM: Homo sapiens

<400> SEQUENCE: 39

```
tagatctctc agatgctggg gaagacccag cccctctgca gagagggata gttcagggtt     60
cgggtttttt ctttcctcct gggctgagaa agctcatgga aagctggaat aaccatgcat    120
actgttacag caaatccaac agggctccca ccatggtggt tttcaggtga ctgtggatgc    180
caagcaggca agctcctggt gaaggggga gagcagggat tagaagcact cagaagggc      240 tgagagtcat gtggggctca cactgcattt gcagctgggt tcaccctgac ctcaggccca    300
acttagatga ggaaggatta gcagtaatta atgccatgtg ccgccttctc ccagctcccc    360
ggggcacgaa cactgcccag ctgatgaggg gattctgaaa gaaccattat gtccaattgt    420
ctcaattatg caaaccctgc tgacatttcc agccagggaa gggcggctgg gtgggagggg    480
gccatggcgg ggccacttca aaggaaaagc tctagctccc ctacctctct cacatcctaa    540
ggctgccttt gtggaggggg ccatggcggg gccacttcaa aggaaaagct ctagctcccc    600
tacctctctc acatcctaag gctgcctttg tgcttcacag caatcatgag ggcccaggcc    660
```

| | |
|---|---|
| caagtgctca catgctcctc atggggactg ctcctcttaa agggtggacc ctcctcaccc | 720 |
| agcccctgc cctggccaag gagctagct | 749 |

<210> SEQ ID NO 40
<211> LENGTH: 8
<212> TYPE: DNA
<213> ORGANISM: Homo sapiens

<400> SEQUENCE: 40

| | |
|---|---|
| aaagggaa | 8 |

<210> SEQ ID NO 41
<211> LENGTH: 4648
<212> TYPE: DNA
<213> ORGANISM: Homo sapiens

<400> SEQUENCE: 41

| | |
|---|---|
| tgatgcgtcc cccccaacc tttccctcac cccctcccac cccagccccc gactccagcc | 60 |
| agcgcctccc tccaccccag gacgccactc atttcatctc atttaaggga aaaatatata | 120 |
| tctatctatt tgaggaaact gaggacctcg gaatctctag caagggctca acttcgaaaa | 180 |
| tggcaacaac agagatgcaa aaagctaaaa agacaccccc cccctttaaa tggttttctt | 240 |
| tttgaggcaa gttggatgaa cagagaaggg aagagaggaa gaacgagagg aagagaaggg | 300 |
| aaggaagtgt ttgtgtagaa gagagagaaa gacgaataga gttaggaaaa ggaagacaag | 360 |
| caggtgggca ggaaggacat gcaccgagac caggcagggg cccaactttc acgtccagcc | 420 |
| ctggcctggg gtcgggagag gtgggcgcta gaagatgcag cccaggatgt ggcaatcaat | 480 |
| gacactattg gggtttccca ggatggattg gtcaggggga gaaggaaaa ggcaaaacac | 540 |
| tccaggacct ctcccggatc tgtctcctcc tctagccagc agtatggaca gctgaccccc | 600 |
| tgaacttcct ctcctcttac ctgggcagag tgttgtctct ccccaaattt ataaaaacta | 660 |
| aaatgcattc cattcctctg aaagcaaaac aaattcataa ttgagtgata ttaaatagag | 720 |
| aggttttcgg aagcagatct gtgaatatga aatacatgtg catatttcat tccccaggca | 780 |
| gacattttt agaaatcaat acatgcccca atattggaaa gacttgttct tccacggtga | 840 |
| ctacagtaca tgctgaagcg tgccgtttca gccctcattt aattcaattt gtaagtagcg | 900 |
| cagcagcctc tgtggggggag gataggctga aaaaaaaaag tgggctcgta tttatctaca | 960 |
| ggactccata tagtcatata taggcatata aatctattct ttttctttgt ttttttcttt | 1020 |
| cttcctttct ttcaaaggtt tgcattaact tttcaaagta gttcctatag ggcattgag | 1080 |
| gagcttcctc attctgggaa aactgagaaa acccatattc tcctaataca acccgtaata | 1140 |
| gcattttgc ctgcctcgag gcagagtttc ccgtgagcaa taaactcagc ttttttgtgg | 1200 |
| ggcacagtac tggatttgac agtgattccc cacgtgtgtt catctgcacc caccgagcca | 1260 |
| ggcagaggcc agccctccgt ggtgcacaca gcacgcgcct cagtccatcc cattttagtc | 1320 |
| tttaacccct caggaagtca cagtctccgg acaccacacc acatgagccc aacaggtcca | 1380 |
| cgatggatcc accagtccca ccccagcctt ttcctttcat ctgaacagaa tgtgcatttt | 1440 |
| tggaagcctc cctcactctc catgctggca gagcaggagg gagactgaag taagagatgg | 1500 |
| cagagggaga tggtggcaaa aaggtttaga tgcaggagaa cagtaagatg gatggttccg | 1560 |
| gccagagtcg atgtggggag gaacagaggg ctgaagggag aggggctga ctgttccatt | 1620 |
| ctagctttgg cacaaagcag cagaaagggg gaaaagccaa tagaaatttc cttagcttcc | 1680 |
| ccaccatatg tattttctag gatttgagag gaaagagagg aaaatggggg aatgggttgc | 1740 |

```
aaaatagaaa tgagcttaat ccaggccgca gagccaggga aggtgagtaa ctttaggagg    1800
gtgctagact ttagaagcca gataggaaga atcagtctaa actggccatg ctttggaagg    1860
gacaagacta tgtgctccgc tgcccacctt cagcctgcaa tgagggactg aggcccacga    1920
gtctttccag ctcttcctcc attctggcca gtccctgcat cctccctggg gtggaggatg    1980
gaaggaaagc tgggacaagc agggaacgca tgattcaggg atgctgtcac tcggcagcca    2040
gattccgaaa ctcccattct ccaatgactt cctcaaccaa tgggtggcct tgtgactgtt    2100
ctttaaggct gaagatatcc aggaaggggg gcttggacac tggccaagga gacccttcg     2160
tgctgtggac acagctctct tcactctttg ctcatggcat gacacagcgg agaccgcctc    2220
caacaacgaa tttggggcta cgaagaggaa tagcgaaaaa gcaaatctgt ttcaactgat    2280
gggaacccta tagctataga acttgggggc tatctcctat gccctggac aggacagttg      2340
gctggggaca ggagaagtgc tcaatcttca tgagacaaag gggcccgata gggccagcag    2400
ccacaaggcc ttgacctgcc gagtcagcat gccccatctc tctgcacagc tgtcccctaa    2460
acccaactca cgtttctgta tgtcttaggc cagtatccca aacctcttcc acgtcactgt    2520
tctttccacc cattctccct ttgcatcttg agcagttatc caactaggat ctgccaagtg    2580
gatactgggg tgccactccc ctgagaaaag actgagccag gaactacaag ctcccccac     2640
attcctccca gcctggacct aattcttgag aggggctctc tcttcacgga ctgtgtctgg    2700
actttgagca ggcttctgcc ccttgcgttg gctctttgct gccagccatc aggtggggga    2760
ttagagcctg gtgtaagtgc gccagactct tccggtttcc aaagttcgtg cctgcgaacc    2820
caaacctgtg agtctcttct gcatgcagga gtttctcctg ggcagctggt cactccccag    2880
agaagctggg ccttcatgga cacatggaac taagcctccc aaatgggagt tctggctgag    2940
cccagggtgg ggagatcctg ggaagggagg cactggagga agacggcacc tcttccccca    3000
tggcagggtg tgagggaggc aggtttggaa tggtgcgagt atggcaatct aagcaggggt    3060
ctggtctctt tgactccagg ctggcctttg gccgactgtc tgctcaccca gagaccttgg    3120
actccggact atccatggct ccgaatctaa gtgctgccca ctcccatgct cacacccaca    3180
gaaggtcttc ccatcccctt tagattcgtg cctcactcca ccagtgagga agatgcctct    3240
gtctttccca cgactgccag gagatagggga agcccagcca ggactgaccc tccttcctcc    3300
agcctgccct gacccacctg gcaaagcagg gcacatgggg aggaagagac tggaaccttt    3360
ctttgacagc caggcctaga cagacaggcc tggggacact ggccccatga ggggaggaag    3420
gcaggcgcac gaggtccagg gaggcccttt tctgatcatg ccccttctct cccaccccat    3480
ctccccacca ccacctctgt ggcctccatg gtaccccca agggctggcc tcccctagag     3540
ggtgggcctc aaccacctgc tcccgccacg caccggttag tgagacaggg ctgccacggc    3600
aaccgccaag cccccctcaa ggtgggacag taccccggac ccatccactc actcctgaga    3660
gggctccggc ccagaatggg aacctcagag aagagctcta aggagaagaa acccatagc     3720
gtcagagagg atatgtctgg cttccaagag aaaggaggct ccgttttgca aagtggagga    3780
gggacgaggg acagggggttt caccagccag caacctgggc cttgtactgt ctgtgttttt    3840
aaaaccacta aagtgcaaga attacattgc actgttctc cactttttat tttctcttag      3900
gcttttgttt ctatttcaaa catactttct tggttttcta atggagtata tagtttagtc    3960
atttcacaga ctctggcctc ctctcctgaa atccttttgg atggggaaag ggaaggtggg    4020
gagggtccga ggggaagggg accccagctt ccctgtgccc gctcacccca ctccaccagt    4080
```

-continued

```
ccccggtcgc cagccggagt ctcctctcta ccgccactgt cacaccgtag cccacatgga    4140
tagcacagtt gtcagacaag attccttcag attccgagtt gcctaccggt tgttttcgtt    4200
gttgttgttg ttgttttct ttttcttttt tttttgaag acagcaataa ccacagtaca      4260
tattactgta gttctctata gttttacata cattcatacc ataactctgt tctctcctct    4320
tttttgtttt caactttaaa aacaaaaata aacgatgata atctttactg gtgaaaagga    4380
tggaaaaata aatcaacaaa tgcaaccagt ttgtgagaaa aaaaaaaaaa agccgaaaaa    4440
aaaaaaaaaa acacctgaat gcggaagagc tcggctcccg tttagcattt tgtacttaag    4500
gaaataaaaa accaacaaag gatctcacat tttcttaaaa agtgaagatt gctgtatact    4560
atttattcaa cttataattt atgttactcc ttgatctttg tcttttgtca tgacaaagca    4620
tttatttaat aaagttatgc attcagtt                                       4648
```

<210> SEQ ID NO 42
<211> LENGTH: 8
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42 taagccta                                                              8

MIR-211 EXPRESSION AND RELATED PATHWAYS IN HUMAN MELANOMA

CROSS REFERENCE TO RELATED APPLICATIONS

This application is a continuation of U.S. patent application Ser. No. 13/840,648, filed on Mar. 15, 2013 and published as US 2014/0134231, which is a continuation-in-part of U.S. patent application Ser. No. 13/271,030, filed Oct. 11, 2011 and published as US 2012/0108457, which claims priority to U.S. Provisional Patent Application Nos. 61/391,948, filed Oct. 11, 2010 and 61/442,108, filed Feb. 11, 2011, each of which is incorporated by reference in its entirety.

STATEMENT OF GOVERNMENT-SPONSORED RESEARCH

This invention was made with United States government support awarded by the following agencies: National Institutes of Health under Grant No. 1R01GM084881-01, and the National Science Foundation under Grant No. FIBR 0527023. The United States government has certain rights in the invention.

FIELD OF THE INVENTION

The present invention relates to methods of diagnosing and treating human melanoma, including human melanoma characterized by resistance to at least one chemotherapeutic agent.

BACKGROUND OF THE INVENTION

The following discussion of the background of the invention is merely provided to aid the reader in understanding the invention and is not admitted to describe or constitute prior art to the present invention.

Melanoma, a cancer of the pigment-producing cells in the skin epidermis, can be highly metastatic, and malignant melanomas are relatively resistant to standard chemotherapy. A major cause for melanoma initiation is extensive or intermittent exposure to the sun's radiation over a period of time, and the extent of melanin pigmentation is an important risk factor. The exact molecular mechanisms that lead to melanoma are complex and poorly understood, and may involve both mutagenic DNA lesions and epigenetic misregulation. The complexity is added by the involvement of several different signal transduction pathways, such as the Hedgehog pathway, which controls BCL2-mediated apoptosis; mutations in the Patched gene, the endpoint of the Hedgehog pathway, have also been correlated with skin cancers [3,12-15].

A frequent causative mechanism for an inherited form of predisposition to melanoma is thought to be a chromosomal deletion over 9p21. The 9p21 site harbors the tumor suppressor gene INK4a and accompanies additional inactivating mutations that lead to the constitutive activation of genes such as BRAF [16,17]. INK4a encodes one of several cyclin-dependent protein kinase inhibitors, which is located adjacent to an alternate reading frame of the human $p14^{ARF}$. $P14^{ARF}$ binds to the Mdm2 protein in several cell lines (though remains untested in melanoma cell lines, to our knowledge) and thereby abrogates Mdm2's binding to p53, causing p53 to be stabilized and nuclear localized. The loss of INK4a therefore may lead to interference of two separate pathways of cell cycle control: CDK signaling and suppression of p53 activity by Mdm2-induced acceleration of p53 degradation. Methylation near the 5' upstream region of INK4a has been shown in some 10% of melanomas [7], suggesting that epigenetic down-regulation of this gene may be important for melanoma development. The activation of BRAF alone may be insufficient to cause metastatic melanoma, but additional mutagenic or epigenetic events such as the inactivation of tumor suppressor genes, e.g., Pten [18], may be important. There is evidence that the NOTCH signaling pathway is also important for distinguishing normal melanocytes from melanoma cells [19,20]. But, BRAF is mutated in over 60% of human melanoma. Several small-molecule inhibitors of BRAF are known, such as vemurafenib, but a significant hurdle to its use exists due to the emergence of vemurafenib-resistant cells Measurement of genome-wide DNA copy number variations, together with analysis of somatic mutations in specific marker genes, can be used to distinguish among different melanoma subtypes with reasonable accuracy [21]. Particularly noteworthy is the recent demonstration of abnormally high oncogenic potentials of single melanoma cells [22], emphasizing the need for a better understanding the molecular mechanisms of melanoma progression.

In the search for such an understanding, attention has recently focused on the role of small non-coding RNA molecules in cancer development [23-27] and in melanoma in particular [28-32]. miRNAs influence cancer development by serving either as tumor suppressors or oncogenes [33-39] by their negative regulatory effects on mRNA encoded by oncogenes or tumor suppressor genes, respectively. With the goal of defining the genes with major contributions to melanoma, several genome-wide expression level studies have identified a number of protein-coding [40] and microRNA (miRNA) genes as important players [32,41-43]. Several of these genes and their expression signatures exhibit distinct patterns among malignant metastatic melanomas and their benign forms, but their significance with respect to melanoma initiation and progression is poorly understood. For example, miR-221/222 were found to down-regulate p27Kip1/CDKN1B and the c-KIT receptor, which controls the progression of neoplasia leading to enhanced proliferation and reduced differentiation in melanoma cells [42]. Similarly, high miR-137 expression in melanoma cell lines down-regulates microphthalma associated transcription factor (MITF), a transcription factor important for melanocyte cell growth, maturation, apoptosis, and pigmentation [32]. The depletion of miR-182 reduces invasiveness and induces melanoma cell death by suppressing the expression of transcription factors FOXO3 and MITF [43], suggesting that its increased expression may be associated with certain aspects of melanoma biology.

With such a number of interrelated genetic causes of melanoma, and with the resulting wide array of individual phenotypes that may result from the various permutations, a clear need remains for improved methods of diagnostics of individual resistance to chemotherapeutic agents, as well as methods of treatment in patients exhibiting the same. Furthermore, one hallmark of melanoma is the ability to re-route major pathways of energy provision and consumption to support the energy demands associated with growth and survival; therefore, there remains a need for a more complete understanding of the mechanistic role of microRNAs in modulating target genes that affect protein, carbohydrate, and lipid metabolism, and, therefore, contribute to melanoma.

SUMMARY OF THE INVENTION

In some aspects, the present invention is based on the discovery of the correlation between miRNA-211 expression and regulation and human melanoma.

In a first aspect, the present invention provides a method for diagnosing melanoma in a subject suspected of having melanoma comprising: (i) assessing the expression level of KCNMA1 in a biological sample obtained from the subject; (ii) comparing the expression level of KCNMA1 in the sample to a reference expression level derived from the expression level of KCNMA1 in samples obtained from subjects diagnosed as not having melanoma; and (iii) identifying the subject as having melanoma when the expression level of KCNMA1 in the sample is greater than the reference expression level or identifying the subject as not having melanoma when the expression level of KCNMA1 in the sample is not greater than the reference expression level. In some embodiments, the biological sample may comprise skin, skin epidermis, or melanocytes.

In further embodiments, the expression level of KCNMA1 may be assessed by evaluating the amount of KCNMA1 mRNA in the biological sample. Such an evaluation of the amount of KCNMA1 mRNA may comprise reverse transcriptase PCR (RT-PCR), or, in further embodiments, may comprise array hybridization, wherein the array comprises an immobilized nucleic acid probe that specifically hybridizes KCNMA1 mRNA, KCNMA1 cDNA, or complements thereof. In still further embodiments, the expression level of KCNMA1 is assessed by evaluating the amount of KCNMA1 protein in the biological sample.

Another aspect of the present invention provides a method for determining the risk of a subject for developing melanoma comprising: (i) assessing the expression level of KCNMA1 in a biological sample obtained from the subject; (ii) comparing the expression level of KCNMA1 in the sample to the a reference expression level derived from the expression level of KCNMA1 in samples obtained from subjects diagnosed as not having melanoma; and (iii) identifying the subject as having increased risk of developing melanoma when the expression level of KCNMA1 in the sample is greater than the reference expression level or identifying the subject as not having an increased risk of melanoma when the expression level of KCNMA1 in the sample is not greater than the reference expression level. In some embodiments, the biological sample may comprise skin, skin epidermis, or melanocytes.

In further embodiments, the expression level of KCNMA1 may be assessed by evaluating the amount of KCNMA1 mRNA in the biological sample. Such an evaluation of the amount of KCNMA1 mRNA may comprise reverse transcriptase PCR (RT-PCR), or, in further embodiments, may comprise array hybridization, wherein the array comprises an immobilized nucleic acid probe that specifically hybridizes KCNMA1 mRNA, KCNMA1 cDNA, or complements thereof. In still further embodiments, the expression level of KCNMA1 is assessed by evaluating the amount of KCNMA1 protein in the biological sample.

In another aspect, the present invention provides a method for treating a patient diagnosed as having melanoma comprising administering to the patient an effective amount of a therapeutic agent that reduces KCNMA1 biological activity. The biological activity may, in some embodiments, be reduced in the melanoma cells by, in further embodiments, at least 10%, at least 50%, or at least 90%.

In some embodiments, the therapeutic agent may comprise a KCNMA1 siRNA, a KCNMA1 anti-sense nucleic acid, an anti-KCNMA1 antibody, or a nucleic acid encoding miR-211. Such a nucleic acid may also be encoded in a vector or a viral vector. Additionally, the therapeutic agent may be contained within a liposome in some embodiments. In some embodiments, it may reduce the expression of KCNMA1 mRNA or KCNMA1 protein, or inhibit the potassium conductance of the KCNMA1 protein.

In still another aspect, the present invention provides a method for determining the proliferation rate of melanoma in a subject comprising: (i) assessing the expression level of KCNMA1 in a melanoma sample obtained from the subject; and (ii) identifying the proliferation rate of the melanoma, wherein a higher expression level of KCNMA1 in the sample indicates a greater proliferation rate and a lower expression level of KCNMA1 in the sample indicates a lower proliferation rate.

In further embodiments, the expression level of KCNMA1 may be assessed by evaluating the amount of KCNMA1 mRNA in the melanoma sample. Such an evaluation of the amount of KCNMA1 mRNA may comprise reverse transcriptase PCR (RT-PCR), or, in further embodiments, may comprise array hybridization, wherein the array comprises an immobilized nucleic acid probe that specifically hybridizes KCNMA1 mRNA, KCNMA1 cDNA, or complements thereof. The expression level of KCNMA1 may also, in some embodiments, be assessed by evaluating the amount of KCNMA1 protein in the melanoma sample.

In yet another aspect of the present invention, a method is provided for determining the metastatic potential of melanoma in a subject comprising: (i) assessing the expression level of KCNMA1 in a melanoma sample obtained from the subject; and (ii) identifying the metastatic potential of the melanoma, wherein a higher expression level of KCNMA1 in the sample indicates a greater metastatic potential and a lower expression level of KCNMA1 in the sample indicates a lower metastatic potential.

In further embodiments, the expression level of KCNMA1 may be assessed by evaluating the amount of KCNMA1 mRNA in the melanoma sample. Such an evaluation of the amount of KCNMA1 mRNA may comprise reverse transcriptase PCR (RT-PCR), or, in further embodiments, may comprise array hybridization, wherein the array comprises an immobilized nucleic acid probe that specifically hybridizes KCNMA1 mRNA, KCNMA1 cDNA, or complements thereof. The expression level of KCNMA1 may also, in some embodiments, be assessed by evaluating the amount of KCNMA1 protein in the melanoma sample.

In another aspect, the present invention provides a method for diagnosing melanoma in a subject suspected of having melanoma comprising: (i) assessing the expression level of MITF in a biological sample obtained from the subject; (ii) comparing the expression level of MITF in the sample to the a reference expression level derived from the expression level of MITF in samples obtained from subjects diagnosed as not having melanoma; and (iii) identifying the subject as having melanoma when the expression level of MITF in the sample is less than the reference expression level or identifying the subject as not having melanoma when the expression level of MITF in the sample is not less than the reference expression level. In some embodiments, the biological sample may comprise skin, skin epidermis, or melanocytes.

In some embodiments, the expression level of MITF is assessed by evaluating the amount of MITF mRNA in the biological sample. Such evaluation may, in some embodiments, comprise reverse transcriptase PCR (RT-PCR). In further embodiments, such evaluation may comprise array hybridization, wherein the array comprises an immobilized nucleic acid probe that specifically hybridizes MITF mRNA, MITF cDNA, or complements thereof. expression level of MITF may additionally be assessed by evaluating the amount of MITF protein in the biological sample.

In still a further aspect of the present invention, a method is provided for determining the risk of a subject for developing melanoma comprising: (i) assessing the expression level of MITF in a biological sample obtained from the subject; (ii) comparing the expression level of MITF in the sample to the a reference expression level derived from the expression level of MITF in samples obtained from subjects diagnosed as not having melanoma; and (iii) identifying the subject as having increased risk of developing melanoma when the expression level of MITF in the sample is less than the reference expression level or identifying the subject as not having an increased risk of melanoma when the expression level of MITF in the sample is not less than the reference expression level. In some embodiments, the biological sample may comprise skin, skin epidermis, or melanocytes.

In some embodiments, the expression level of MITF is assessed by evaluating the amount of MITF mRNA in the biological sample. Such evaluation may, in some embodiments, comprise reverse transcriptase PCR (RT-PCR). In further embodiments, such evaluation may comprise array hybridization, wherein the array comprises an immobilized nucleic acid probe that specifically hybridizes MITF mRNA, MITF cDNA, or complements thereof. expression level of MITF may additionally be assessed by evaluating the amount of MITF protein in the biological sample.

In yet another aspect, the present invention provides a method for treating a patient diagnosed as having melanoma comprising administering to the patient an effective amount of a therapeutic agent that increases MITF biological activity. In some embodiments, the MITF biological activity is increased in the melanoma cells by, in further embodiments, at least 10%, at least 50%, or at least 100%.

In some embodiments, the therapeutic agent may comprise a nucleic acid encoding MITF. Such a nucleic acid may, in some embodiments, be encoded in a vector or a viral vector. The therapeutic agent may additionally be contained within a liposome. The administration of the therapeutic agent may, in further embodiments, result in an increase in the expression of miR-211 or TRPM1, or may result in a reduction in the expression of KCNMA1.

In another aspect, the present invention provides a method for determining the proliferation rate of melanoma in a subject comprising: (i) assessing the expression level of MITF in a melanoma sample obtained from the subject; and (ii) identifying the proliferation rate of the melanoma, wherein a lower expression level of MITF in the sample indicates a greater proliferation rate and a higher expression level of MITF in the sample indicates a lower proliferation rate.

In some embodiments, the expression level of MITF is assessed by evaluating the amount of MITF mRNA in the melanoma sample. Such an evaluation may, in further embodiments, comprise reverse transcriptase PCR (RT-PCR) or array hybridization, wherein the array comprises an immobilized nucleic acid probe that specifically hybridizes MITF mRNA, MITF cDNA, or complements thereof. The expression level of MITF may further be assessed by evaluating the amount of MITF protein in the biological sample.

Yet another aspect of the present invention provides a method for determining the metastatic potential of melanoma in a subject comprising: (i) assessing the expression level of MITF in a melanoma sample obtained from the subject; and (ii) identifying the metastatic potential of the melanoma, wherein a lower expression level of MITF in the sample indicates a greater metastatic potential and a higher expression level of MITF in the sample indicates a lower metastatic potential.

In some embodiments, the expression level of MITF is assessed by evaluating the amount of MITF mRNA in the melanoma sample. Such an evaluation may, in further embodiments, comprise reverse transcriptase PCR (RT-PCR) or array hybridization, wherein the array comprises an immobilized nucleic acid probe that specifically hybridizes MITF mRNA, MITF cDNA, or complements thereof. The expression level of MITF may further be assessed by evaluating the amount of MITF protein in the biological sample.

In still another aspect of the present invention, a method is provided for diagnosing melanoma in a subject suspected of having melanoma comprising: (i) assessing the expression level of TRPM1 in a biological sample obtained from the subject; (ii) comparing the expression level of TRPM1 in the sample to the a reference expression level derived from the expression level of TRPM1 in samples obtained from subjects diagnosed as not having melanoma; and (iii) identifying the subject as having melanoma when the expression level of TRPM1 in the sample is less than the reference expression level or identifying the subject as not having melanoma when the expression level of TRPM1 in the sample is not less than the reference expression level. In some embodiments, the biological sample may comprise skin, skin epidermis, or melanocytes.

In further embodiments, the expression level of TRPM1 is assessed by evaluating the amount of TRPM1 mRNA in the biological sample. Such an evaluation may, in some embodiments, comprise reverse transcriptase PCR (RT-PCR) or, in further embodiments, array hybridization, wherein the array comprises an immobilized nucleic acid probe that specifically hybridizes TRPM1 mRNA, TRPM1 cDNA, or complements thereof. The expression level of TRPM1 may be assessed in further embodiments by evaluating the amount of TRPM1 protein in the biological sample.

In yet another aspect of the present invention, a method is provided for determining the risk of a subject for developing melanoma comprising: (i) assessing the expression level of TRPM1 in a biological sample obtained from the subject; (ii) comparing the expression level of TRPM1 in the sample to the a reference expression level derived from the expression level of TRPM1 in samples obtained from subjects diagnosed as not having melanoma; and (iii) identifying the subject as having increased risk of developing melanoma when the expression level of TRPM1 in the sample is less than the reference expression level or identifying the subject as not having an increased risk of melanoma when the expression level of TRPM1 in the sample is not less than the reference expression level. In some embodiments, the biological sample may comprise skin, skin epidermis, or melanocytes.

In further embodiments, the expression level of TRPM1 is assessed by evaluating the amount of TRPM1 mRNA in the biological sample. Such an evaluation may, in some embodiments, comprise reverse transcriptase PCR (RT-PCR) or, in further embodiments, array hybridization, wherein the array comprises an immobilized nucleic acid probe that specifically hybridizes TRPM1 mRNA, TRPM1 cDNA, or complements thereof. The expression level of TRPM1 may be assessed in further embodiments by evaluating the amount of TRPM1 protein in the biological sample.

In another aspect, the present invention provides a method for treating a patient diagnosed as having melanoma comprising administering to the patient an effective amount of a therapeutic agent that increases TRPM1 biological activity. In some embodiments, the TRPM1 biological activity is increased in the melanoma cells by, in further embodiments, at least 10%, at least 50%, or at least 100%.

In further embodiments, the therapeutic agent may comprise a nucleic acid encoding TRPM1. The nucleic acid may be encoded in a vector or a viral vector, or may be contained within a liposome. The administration of the therapeutic agent may, in some embodiments, result in an increase in the expression of miR-211, or a reduction in the expression of KCNMA1.

In still another aspect of the present invention, a method is provided for determining the proliferation rate of melanoma in a subject comprising: (i) assessing the expression level of TRPM1 in a melanoma sample obtained from the subject; and (ii) identifying the proliferation rate of the melanoma, wherein a lower expression level of TRPM1 in the sample indicates a greater proliferation rate and a higher expression level of TRPM1 in the sample indicates a lower proliferation rate.

In some embodiments, the expression level of TRPM1 is assessed by evaluating the amount of TRPM1 mRNA in the melanoma sample. Such an evaluation may, in some embodiments, comprise reverse transcriptase PCR (RT-PCR) or, in further embodiments, array hybridization, wherein the array comprises an immobilized nucleic acid probe that specifically hybridizes TRPM1 mRNA, TRPM1 cDNA, or complements thereof. The expression level of TRPM1 may be assessed in further embodiments by evaluating the amount of TRPM1 protein in the melanoma sample.

Yet another aspect of the present invention provides a method for determining the metastatic potential of melanoma in a subject comprising: (i) assessing the expression level of TRPM1 in a melanoma sample obtained from the subject; and (ii) identifying the metastatic potential of the melanoma, wherein a lower expression level of TRPM1 in the sample indicates a greater metastatic potential and a higher expression level of TRPM1 in the sample indicates a lower metastatic potential.

In some embodiments, the expression level of TRPM1 is assessed by evaluating the amount of TRPM1 mRNA in the melanoma sample. Such an evaluation may, in some embodiments, comprise reverse transcriptase PCR (RT-PCR) or, in further embodiments, array hybridization, wherein the array comprises an immobilized nucleic acid probe that specifically hybridizes TRPM1 mRNA, TRPM1 cDNA, or complements thereof. The expression level of TRPM1 may be assessed in further embodiments by evaluating the amount of TRPM1 protein in the melanoma sample.

In still another aspect of the present invention, a method is provided for treating a patient diagnosed as having melanoma comprising administering to the patient an effective amount of a therapeutic agent that increases miR-211 biological activity. In some embodiments, the miR-211 biological activity is increased in the melanoma cells. Such an increase may be, in some embodiments, by at least 10%, at least 50%, or at least 100%.

In further embodiments, the therapeutic agent may comprise a nucleic acid encoding miR-211. The nucleic acid may be encoded in a vector or a viral vector, or may be contained within a liposome. The administration of the therapeutic agent may additionally, in some embodiments, result in a reduction in the expression of KCNMA1.

In yet another aspect, the present invention provides a method for determining the proliferation rate of melanoma in a subject comprising: (i) assessing the expression level of miR-211 in a melanoma sample obtained from the subject; and (ii) identifying the proliferation rate of the melanoma, wherein a lower expression level of miR-211 in the sample indicates a greater proliferation rate and a higher expression level of miR-211 in the sample indicates a lower proliferation rate.

In some embodiments, the expression level of miR-211 is assessed by evaluating the amount of miR-211 mRNA in the melanoma sample. Such an evaluation may, in some embodiments, comprise reverse transcriptase PCR (RT-PCR) or, in further embodiments, array hybridization, wherein the array comprises an immobilized nucleic acid probe that specifically hybridizes miR-211 mRNA, miR-211 cDNA, or complements thereof.

In still another aspect of the present invention, a method is provided for determining the metastatic potential of melanoma in a subject comprising: (i) assessing the expression level of miR-211 in a melanoma sample obtained from the subject; and (ii) identifying the metastatic potential of the melanoma, wherein a lower expression level of miR-211 in the sample indicates a greater metastatic potential and a higher expression level of miR-211 in the sample indicates a lower metastatic potential.

In some embodiments, the expression level of miR-211 is assessed by evaluating the amount of miR-211 mRNA in the melanoma sample. Such an evaluation may, in some embodiments, comprise reverse transcriptase PCR (RT-PCR) or, in further embodiments, array hybridization, wherein the array comprises an immobilized nucleic acid probe that specifically hybridizes miR-211 mRNA, miR-211 cDNA, or complements thereof.

In another aspect, a method is provided for diagnosing a human as having melanoma or having an increased likelihood of melanoma, said method comprising,
(i) determining, in a sample obtained from a human, the presence or absence of a TRPM1 gene promoter mutation that causes a reduction in the TRPM1 gene expression relative to the TRPM1 gene expression from a TRPM1 gene promoter lacking that mutation, and (ii) identifying the human has having melanoma or an increased likelihood of melanoma when a TRPM1 gene promoter mutation is identified, and identifying the human as not having melanoma or an increased likelihood of melanoma when the TRPM1 gene promoter mutation is absent. In some embodiments, the TRPM1 gene promoter mutation is selected from the group consisting of the T61C, C116T, A143G, A153G, G331A, G708A, and T724C mutations relative to SEQ ID NO: 36. In further embodiments, the sample may comprise skin.

In yet another aspect, the present invention provides a method for treating a patient diagnosed as having melanoma comprising administering to the patient an effective amount of a therapeutic agent that increases TP53 biological activity. In some embodiments, the TP53 biological activity is increased in the melanoma cells. In further embodiments, the TP53 biological activity is increased at least 2-fold, at least 3-fold, or at least 5-fold. In still further embodiments, the therapeutic agent may further act to increase miR-211 expression. The therapeutic agent may increase the expression of TP53 mRNA or TP53 protein.

In still another aspect, a method is provided for treating a patient diagnosed as having melanoma comprising administering to the patient an effective amount of a therapeutic agent that reduces IGFBP5 biological activity. In some embodiments, the IGFBP5 biological activity is reduced in the melanoma cells. The biological activity may be reduced by at least 10%, at least 50%, or at least 90%. In further embodiments, the therapeutic agent may comprise an IGFBP5 siNA. The therapeutic agent may, in some embodiments, comprise a nucleic acid encoding miR-211. The nucleic acid may, in some embodiments, be encoded in a vector or a viral vector, or may be contained within a liposome. In still further embodiments, the therapeutic agent may reduce the expression of IGFBP5 mRNA or IGFBP5 protein, or, in some embodiments, may also increase MITF, TP53, or TRPM1 expression.

In still another aspect, a method is provided for diagnosing melanoma in a subject suspected of having melanoma comprising: (i) assessing the expression level of miR-211 in a biological sample obtained from the subject; (ii) comparing the expression level of miR-211 in the sample to the a reference expression level derived from the expression level of miR-211 in samples obtained from subjects diagnosed as not having melanoma; and (iii) identifying the subject as having melanoma when the expression level of miR-211 in the sample is less than the reference expression level or identifying the subject as not having melanoma when the expression level of miR-211 in the sample is not less than the reference expression level. In some embodiments, the biological sample may comprise skin, or, in further embodiments, skin epidermis or melanocytes. In still further embodiments, the expression level of miR-211 is assessed by evaluating the amount of miR-211 mRNA in the biological sample. In further embodiments, the miR-211 mRNA comprises reverse transcriptase PCR (RT-PCR). In still further embodiments, evaluation of the miR-211 mRNA may comprise hybridization, wherein the array comprises an immobilized nucleic acid probe that specifically hybridizes miR-211 mRNA, miR-211 cDNA, or complements thereof.

In some aspects, the present invention is based on the discovery of the correlation between miR-211 expression and regulation and drug resistance, as well as the discovery that expression of miR-211 in melanoma cells modulates a signature pattern of metabolic changes associated with mitochondrial energy metabolism, including increased oxygen consumption, fatty acid synthesis, and destabilization of hypoxia inducible factor 1α (HIF-1α).

In one aspect a method is provided for diagnosing chemotherapeutic resistance against a BRAF inhibitor, in some embodiments vemurafenib resistance, in a subject suffering from melanoma comprising: (i) assessing the expression level of PGC1α or another gene involved in the regulation of miR-211 via MITF and TRPM1 in a biological sample obtained from the subject; (ii) comparing the expression level of the biomarker in the sample to the a reference expression level derived from the expression level of the biomarker in samples obtained from cells having vemurafenib-sensitivity; and (iii) identifying the subject as having a vemurafenib-resistant phenotype when the expression level of the biomarker in the sample is less than the reference expression level or identifying the subject having a vemurafenib-sensitive phenotype when the expression level of the biomarker in the sample is not less than the reference expression level.

In some embodiments, the biological sample comprises skin, skin epidermis, or, in further embodiments, melanocytes. In still further embodiments, the expression level of PGC1α may be assessed by evaluating the amount of PGC1α mRNA in the biological sample, which may, in yet further embodiments, comprise reverse transcriptase PCR (RT-PCR). Evaluating the PGC1α mRNA may, in some embodiments, comprise array hybridization, wherein the array comprises an immobilized nucleic acid probe that specifically hybridizes PGC1α mRNA, PGC1α cDNA, or complements thereof.

In another aspect, the present invention provides a method of treating melanoma characterized by mutated BRAF in a subject suffering from melanoma, said method comprising: administering to the subject a therapeutically effective amount of a pharmaceutical composition comprising at least one agent that acts to decrease the biological activity of PGC1α.

In some embodiments, the therapeutic agent may comprise a nucleic acid encoding PGC1α, or a PGC1α shRNA. The nucleic acid may, in further embodiments, be encoded in a vector, a viral vector, or, in still further embodiments, a liposome. The therapeutic agent may further act to increase the biological activity of miR-211. In some embodiments, the biological activity may be increased by 10% or greater, 50% or greater, or 100% or greater.

In another aspect, a method is provided for treating melanoma in a patient suffering from melanoma, said method comprising: administering to the subject a therapeutically effective amount of a pharmaceutical composition comprising at least one agent that acts to decrease the biological activity of IGFBP5. In some embodiments, the therapeutic agent may comprise a nucleic acid encoding an shIGFBP5 or siIGFBP5. The nucleic acid may, in further embodiments, be encoded in a vector, a viral vector, or, in still further embodiments, a liposome.

In another aspect, a method is provided for treating melanoma in a patient suffering from melanoma, said method comprising: administering to the subject a therapeutically effective amount of a pharmaceutical composition comprising at least one agent that acts to decrease the biological activity of PDK4. In some embodiments, the therapeutic agent may comprise a nucleic acid encoding an sh PDK4 or si PDK4. The nucleic acid may, in further embodiments, be encoded in a vector, a viral vector, or, in still further embodiments, a liposome.

As used herein, the term "nucleic acid molecule" or "nucleic acid" refer to an oligonucleotide, nucleotide or polynucleotide. A nucleic acid molecule may include deoxyribonucleotides, ribonucleotides, modified nucleotides or nucleotide analogs in any combination.

As used herein, the term "nucleotide" refers to a chemical moiety having a sugar (modified, unmodified, or an analog thereof), a nucleotide base (modified, unmodified, or an analog thereof), and a phosphate group (modified, unmodified, or an analog thereof). Nucleotides include deoxyribonucleotides, ribonucleotides, and modified nucleotide analogs including, for example, locked nucleic acids ("LNAs"), peptide nucleic acids ("PNAs"), L-nucleotides, ethylene-bridged nucleic acids ("ENAs"), arabinoside, and nucleotide analogs (including abasic nucleotides).

As used herein, the term "short interfering nucleic acid" or "siNA" refers to any nucleic acid molecule capable of down regulating (i.e., inhibiting) gene expression in a mammalian cells (preferably a human cell). siNA includes without limitation nucleic acid molecules that are capable of mediating sequence specific RNAi, for example short interfering RNA (siRNA), double-stranded RNA (dsRNA), micro-RNA (miRNA), and short hairpin RNA (shRNA).

As used herein, the term "KCNMA1 siRNA" refers to a short interfering nucleic acid as defined above that targets or preferentially binds to an mRNA encoded by KCNMA1.

As used herein, the term "PGC1α siRNA" refers to a short interfering nucleic acid as defined above that targets or preferentially binds to an mRNA encoded by PGC1α.

As used herein, the term "increase in biological activity" refers to any measurable increase of any biological effect caused by an increase in the expression of a nucleic acid or protein. An increase in biological activity may often be measured by increased amounts of RNA (e.g., mRNA) or protein, or may be measured functionally.

As used herein, the term "diagnosing" means determining a disease state or condition in a patient (e.g., melanoma) in such a way as to inform a health care provider as to the necessity or suitability of a treatment for the patient.

As used herein, the term "miR-211" refers to a small, non-coding nucleic acid molecule encoded in the sixth intron of the TRPM1 gene that targets mRNA encoded by PGC1α, KCNMA1, IGFBP5, and/or PDK4. miR-211 may refer to any type of nucleic acid molecule including ribonucleotides, deoxyribonucleotides, or modified nucleotides.

As used herein, the term "sense region" refers to a nucleotide sequence of a siNA molecule complementary (partially or fully) to an antisense region of the siNA molecule. Optionally, the sense strand of a siNA molecule may also include additional nucleotides not complementary to the antisense region of the siNA molecule.

As used herein, the term "antisense region" refers to a nucleotide sequence of a siNA molecule complementary (partially or fully) to a target nucleic acid sequence. Optionally, the antisense strand of a siNA molecule may include additional nucleotides not complementary to the sense region of the siNA molecule.

As used herein, the term "duplex region" refers to the region in two complementary or substantially complementary oligonucleotides that form base pairs with one another that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and/or 3' overhangs.

An "abasic nucleotide" conforms to the general requirements of a nucleotide in that it contains a ribose or deoxyribose sugar and a phosphate but, unlike a normal nucleotide, it lacks a base (i.e., lacks an adenine, guanine, thymine, cytosine, or uracil). Abasic deoxyribose moieties include, for example, abasic deoxyribose-3'-phosphate; 1,2-dideoxy-D-ribofuranose-3-phosphate; 1,4-anhydro-2-deoxy-D-ribitol-3-phosphate.

As used herein, the term "inhibit", "down-regulate", or "reduce," with respect to gene expression, means that the level of RNA molecules encoding one or more proteins or protein subunits (e.g., mRNA) is reduced below that observed in the absence of the inhibitor. Expression may be reduced by at least 90%, 80%, 70%, 60%, 50%, 40%, 30%, 20%, 10%, 5% or below the expression level observed in the absence of the inhibitor.

BRIEF DESCRIPTION OF THE FIGURES

FIGS. 13(A) and (B) are sequence alignments showing the upstream promoter of TRPM1 in melanocytes and the SKMEL-28, A375, and WM1152C melanoma cells lines. The promoter sequences are provided as SEQ ID NOs: 36-39, respectively. Point mutations in the TRPM1 promoters of the A375 and/or WM1152C cell lines are highlighted.

FIGS. 26(A) and (B) together provide the nucleic acid sequence of the 3'-UTR of the IGFBP5 cDNA.

FIG. 38 is a gel showing PDK4 protein expression is virtually undetectable in miR-211-expressing melanoma cells.

DETAILED DESCRIPTION

Figure 1:
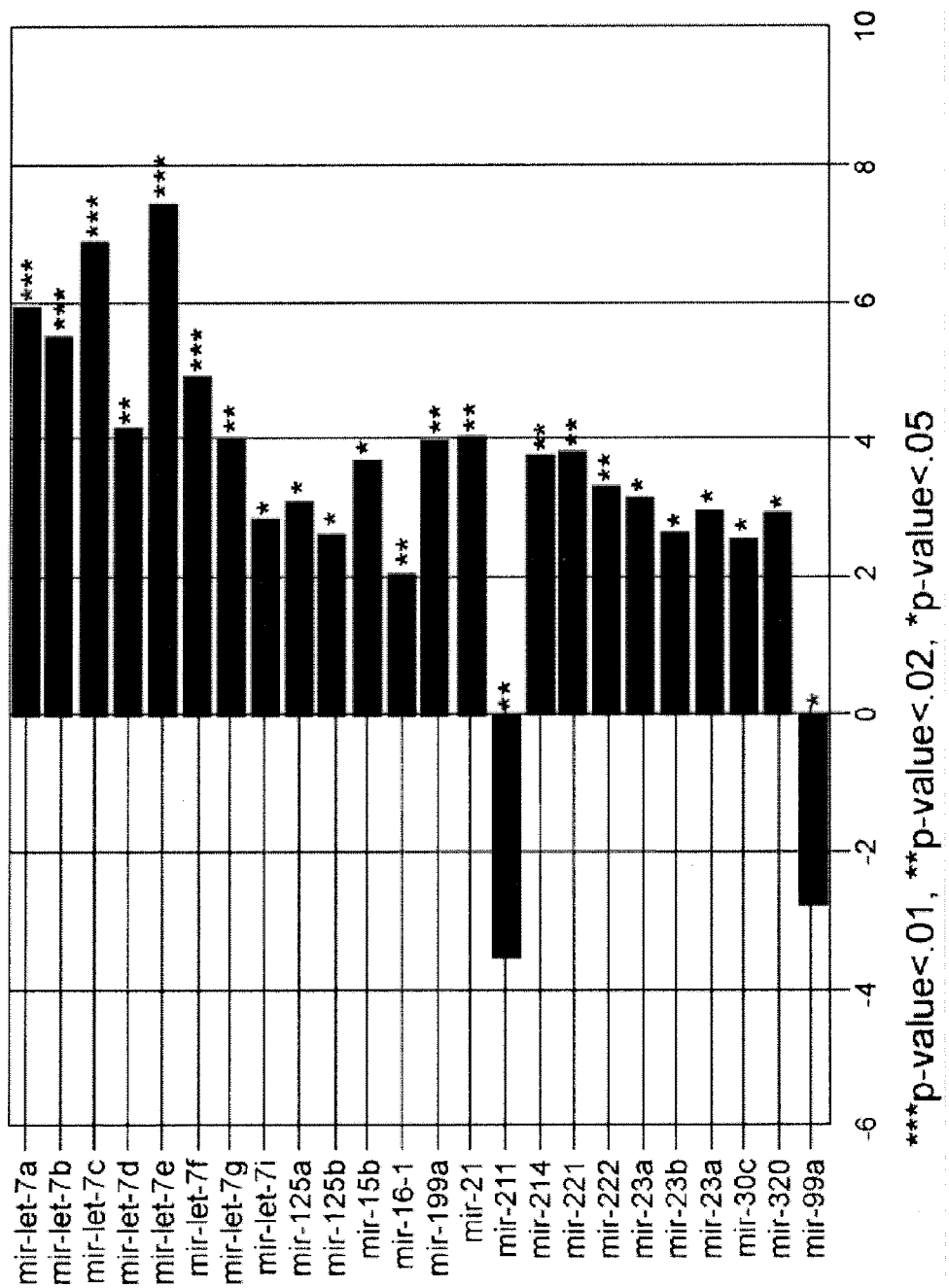
FIG. 1 is a histogram showing $\log_2$ of mean expression ratios of miRNA levels.

The immediate molecular mechanisms behind invasive melanoma are poorly understood. Recent studies implicate microRNAs (miRNAs) as important agents in melanoma and other cancers. To investigate the role of miRNAs in melanoma, human melanoma cell lines were subjected to miRNA expression profiling, and a range of variations in several miRNAs was reported. Specifically, compared with expression levels in melanocytes, levels of miR-211 were consistently reduced in all eight non-pigmented melanoma cell lines we examined; they were also reduced in 21 out of 30 distinct melanoma samples from patients, classified as primary in situ, regional metastatic, distant metastatic, and nodal metastatic. The levels of several predicted target mRNAs of miR-211 were reduced in melanoma cell lines that ectopically expressed miR-211.

In vivo target cleavage assays confirmed one such target mRNA encoded by KCNMA1. Mutating the miR-211 binding site seed sequences at the KCNMA1 3'-UTR abolished target cleavage. KCNMA1 mRNA and protein expression levels varied inversely with miR-211 levels. Two different melanoma cell lines ectopically expressing miR-211 exhibited significant growth inhibition and reduced invasiveness compared with the respective parental melanoma cell lines. An shRNA against KCNMA1 mRNA also demonstrated similar effects on melanoma cells.

miR-211 is encoded within the sixth intron of TRPM1, a candidate suppressor of melanoma metastasis. The transcription factor MITF, important for melanocyte development and function, is needed for high TRPM1 expression. MITF is also needed for miR-211 expression, suggesting that the tumor-suppressor activities of MITF and/or TRPM1 may at least partially be due to miR-211's negative post transcriptional effects on the KCNMA1 transcript. Given previous reports of high KCNMA1 levels in metastasizing melanoma, prostate cancer and glioma, the findings that miR-211 is a direct posttranscriptional regulator of KCNMA1 expression as well as the dependence of this miRNA's expression on MITF activity, establishes miR-211 as an important regulatory agent in human melanoma. Several target genes of miR-211 have been identified, including Runt-related transcription factor 2 (RUNX2), insulin-like growth factor 2 receptor (IGF2R), TGF-beta receptor 2 (TGFBR2), the POU domain-containing transcription factor BRN2, and nuclear factor of activated T cells 5 (NFAT5).

The transcription factor MITF has been shown to be regulated by PGC1α, which is a second mRNA, in addition to KCNMA1, that is targeted by miR-211. Furthermore, the expression of this regulator has been shown to vary in melanoma cells that exhibit resistance to chemotherapeutic agents such as vemurafenib. As is discussed in greater detail in Example 15, below, vemurafenib-resistant cells show significantly reduced expression of PGC1α when compared with vemurafenib-sensitive cells.

The reduced expression of miR-211 in these cell lines can be seen in clinical isolates of human melanomas. Further, there is evidence that a principal effect of the reduced expression of miR-211 is the increased expression of its target transcript KCNMA1. The expression of KCNMA1, encoding a calcium ion-regulated potassium channel protein, appears to at least partially account for the high cell proliferation rate and invasiveness of melanoma cell lines. MITF expression is also important for the coordinate expression of miR-211, and TRPM1. TRPM1 gene is a suppressor of melanoma metastasis, which encodes a transient receptor potential family member calcium channel protein, and encodes miR-211 in its sixth intron.

Current understanding of the molecular mechanisms of carcinogenesis is beginning to include not only the role of protein coding genes but also that of non-coding regulatory RNA, especially miRNAs. In the case of melanoma, the discovery of miRNAs whose expression levels are reduced in melanoma cells can lead to the identification of genes that are responsible for oncogenesis and invasiveness. Along that line, it is shown herein that miR-211 levels are consistently reduced in melanoma cells compared to its levels in melanocytes, and that the expression levels of several potential miR-211 target mRNAs are elevated in melanoma cells. The increased expression of one confirmed target transcript in particular, KCNMA1, is associated with high invasiveness and proliferation in melanoma cells in vitro.

It is likely that the down-regulation of miR-211 causes elevated levels of KCNMA1 protein in melanoma cells, which at least in part explains the invasiveness of malignant melanoma. Additionally, melanoma cell lines engineered to express high levels of miR-211 begin to lose expression shortly after removal from selection, indicating a strong bias against miR-211 expression during the growth of melanoma cell lines and suggests that the rapid proliferation of melanoma cells in culture is directly related to low miR-211 activity in these cells. However, without wishing to be bound by any theory, it is possible that as yet unidentified targets of miR-211 (besides KCNMA1) may have a positive feedback effect on KCNMA1 levels and are responsible for invasiveness. An alternative possibility is that miR-211 down-regulation in melanoma causes other transformational events unrelated to KCNMA1, leading to higher oncogenesis and invasiveness. Both of these more complex possibilities are consistent with some evidence, but not with the full set of data presented herein.

Figure 9:
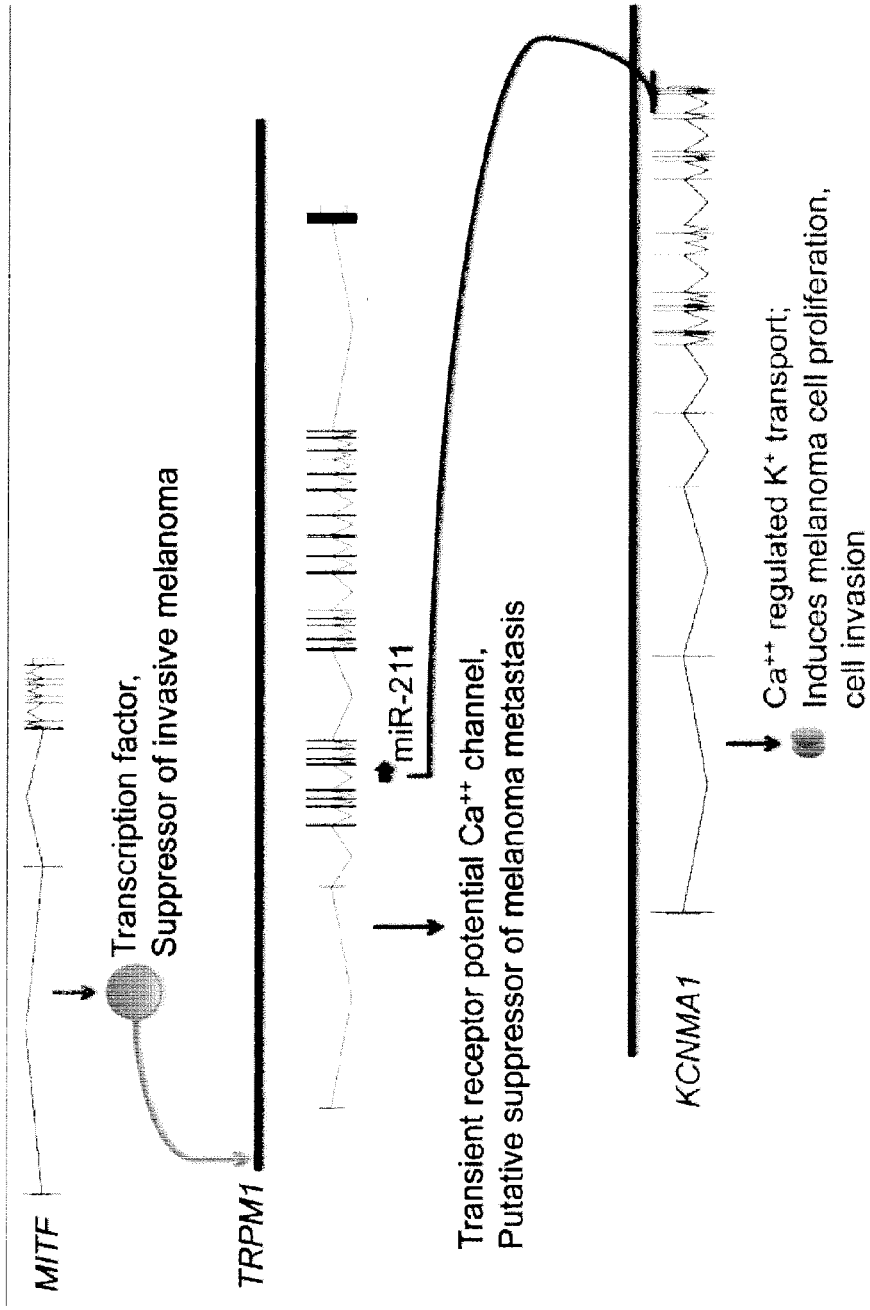
FIG. 9 is an illustration showing a model summarizing the regulation and role of miR-211 in melanoma.

The transcription factor MITF, which regulates the expression of TRPM1, is also needed for high-level expression of miR-211. Thus, the regulation by MITF of both TRPM1 and miR-211 genes can be speculated to have similar effects on melanoma invasiveness separately through their respective gene products: the former a $Ca^{++}$ channel protein (TRPM1), and the latter a miRNA targeted against the $Ca^{++}$ regulated $K^+$ channel protein KCNMA1. Thus, the invasiveness of melanoma cells could partly be the result of the breakdown of processes related to calcium-regulated ion homeostasis. The recent finding that salinomycin, an inhibitor of $K^+$ transport, is a selective inhibitor of cancer stem cell proliferation is consistent with our findings on the role of KCNMA1 in melanoma cells [63]. We cannot eliminate the formal possibility that the potential tumor suppressor activity of TRPM1 gene is, at least in part, due to the co-expression of miR-211 encoded from within its sixth intron. FIG. 9 provides a summary of a simple model of the putative mechanism of development of invasive melanoma, which highlights the role of miR-211.

In contrast to the downregulation of miR-211 levels in most melanoma cells and clinical samples shown herein, Gaur et al. [64] previously reported that miR-211 was over-expressed in 6 of 8 tested melanoma lines from the NCI-60 panel of cancer cells. However, a leave-one-out sensitivity analysis conducted by Gaur et al. [64] failed to show a significant effect on the confidence interval when miR-211 expression level was omitted, suggesting low specificity or sensitivity with respect to miR-211 in those experiments. Muller et al. [41] compared miRNA expression in melanoma cell lines with pooled normal human epidermal melanocytes; miR-211 was not down-regulated in their study. It is likely that the melanocyte cells (pooled epidermal melanocytes) used in the latter studies were physiologically and genetically different from the melanocyte lines used herein. Jukic et al., [44] reported that miR-211 was up-regulated in nevi and dramatically down-regulated in metastatic melanoma compared to nevi controls. These results correspond with the results shown herein and contradict the results published by Schultz, et al., [31].

Given that miR-211 is down-regulated in non-pigmented melanoma and its expression is regulated by the MITF gene, the down-regulation of miR-211 and the corresponding up-regulation of its target transcript KCNMA1 are therefore important molecular events for melanoma development and/or progression.

RNA Interference and siNA

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). Post-transcriptional gene silencing is believed to be an evolutionarily-conserved cellular mechanism for preventing expression of foreign genes that may be introduced into the host cell (Fire et al., 1999, Trends Genet., 15, 358). Post-transcriptional gene silencing may be an evolutionary response to the production of double-stranded RNAs (dsRNAs) resulting from viral infection or from the random integration of transposable elements (transposons) into a host genome. The presence of dsRNA in cells triggers the RNAi response that appears to be different from other known mechanisms involving double stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898,031; Clemens et al., 1997, J. Interferon & Cytokine Res., 17, 503-524; Adah et al., 2001, Curr. Med. Chem., 8, 1189).

The presence of long dsRNAs in cells stimulates the activity of dicer, a ribonuclease III enzyme (Bass, 2000, Cell, 101, 235; Zamore et al., 2000, Cell, 101, 25-33; Hammond et al., 2000, Nature, 404, 293). Dicer processes long dsRNA into double-stranded short interfering RNAs (siRNAs) which are typically about 21 to about 23 nucleotides in length and include about 19 base pair duplexes (Zamore et al., 2000, Cell, 101, 25-33; Bass, 2000, Cell, 101, 235; Elbashir et al., 2001, Genes Dev., 15, 188).

Single-stranded RNA, including the sense strand of siRNA, trigger an RNAi response mediated by an endonuclease complex known as an RNA-induced silencing complex (RISC). RISC mediates cleavage of this single-stranded RNA in the middle of the siRNA duplex region (i.e., the region complementary to the antisense strand of the siRNA duplex) (Elbashir et al., 2001, Genes Dev., 15, 188).

In certain embodiments, the siNAs may be a substrate for the cytoplasmic Dicer enzyme (i.e., a "Dicer substrate") which is characterized as a double stranded nucleic acid capable of being processed in vivo by Dicer to produce an active nucleic acid molecules. The activity of Dicer and requirements for Dicer substrates are described, for example, U.S. 2005/0244858. Briefly, it has been found that dsRNA, having about 25 to about 30 nucleotides, effective result in a down-regulation of gene expression. Without wishing to be bound by any theory, it is believed that Dicer cleaves the longer double stranded nucleic acid into shorter segments and facilitates the incorporation of the single-stranded cleavage products into the RNA-induced silencing complex (RISC complex). The active RISC complex, containing a single-stranded nucleic acid cleaves the cytoplasmic RNA having complementary sequences.

It is believed that Dicer substrates must conform to certain general requirements in order to be processed by Dicer. The Dicer substrates must of a sufficient length (about 25 to about 30 nucleotides) to produce an active nucleic acid molecule and may further include one or more of the following properties: (i) the dsRNA is asymmetric, e.g., has a 3' overhang on the first strand (antisense strand) and (ii) the dsRNA has a modified 3' end on the antisense strand (sense strand) to direct orientation of Dicer binding and processing of the dsRNA to an active siRNA. The Dicer substrates may be symmetric or asymmetric. For example, Dicer substrates may have a sense strand includes 22-28 nucleotides and the antisense strand may include 24-30 nucleotides, resulting in duplex regions of about 25 to about 30 nucleotides, optionally having 3'-overhangs of 1-3 nucleotides.

Dicer substrates may have any modifications to the nucleotide base, sugar or phosphate backbone as known in the art and/or as described herein for other nucleic acid molecules (such as siNA molecules).

The RNAi pathway may be induced in mammalian and other cells by the introduction of synthetic siRNAs that are 21 nucleotides in length (Elbashir et al., 2001, Nature, 411, 494 and Tuschl et al., WO 01/75164; incorporated by reference in their entirety). Other examples of the requirements necessary to induce the down-regulation of gene expression by RNAi are described in Zamore et al., 2000, Cell, 101, 25-33; Bass, 2001, Nature, 411, 428-429; Kreutzer et al., WO 00/44895; Zernicka-Goetz et al., WO 01/36646; Fire, WO 99/32619; Plaetinck et al., WO 00/01846; Mello and Fire, WO 01/29058; Deschamps-Depaillette, WO 99/07409; and Li et al., WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831; each of which is hereby incorporated by reference in its entirety.

Briefly, an siNA nucleic acid molecule can be assembled from two separate polynucleotide strands (a sense strand and an antisense strand) that are at least partially complementary and capable of forming stable duplexes. The length of the duplex region may vary from about 15 to about 49 nucleotides (e.g., about 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides). Typically, the antisense strand includes nucleotide sequence that is complementary to nucleotide sequence in a target nucleic acid molecule. The sense strand includes nucleotide sequence corresponding to the target nucleic acid sequence which is therefore at least substantially complementary to the antisense stand. Optionally, an siNA is "RISC length" and/or may be a substrate for the Dicer enzyme. Optionally, an siNA nucleic acid molecule may be assembled from a single polynucleotide, where the sense and antisense regions of the nucleic acid molecules are linked such that the antisense region and sense region fold to form a duplex region (i.e., forming a hairpin structure).

5' Ends, 3' Ends and Overhangs siNAs may be blunt-ended on both sides, have overhangs on both sides or a combination of blunt and overhang ends. Overhangs may occur on either the 5'- or 3'-end of the sense or antisense strand. Overhangs typically consist of 1-8 nucleotides (e.g., 1, 2, 3, 4, 5, 6, 7, or 8 nucleotides each) and are not necessarily the same length on the 5'- and 3'-end of the siNA duplex. The nucleotide(s) forming the overhang need not be of the same character as those of the duplex region and may include deoxyribonucleotide(s), ribonucleotide(s), natural and non-natural nucleobases or any nucleotide modified in the sugar, base or phosphate group such as disclosed herein.

The 5'- and/or 3'-end of one or both strands of the nucleic acid may include a free hydroxyl group or may contain a chemical modification to improve stability. Examples of end modifications (e.g., terminal caps) include, but are not limited to, abasic, deoxy abasic, inverted (deoxy) abasic, glyceryl, dinucleotide, acyclic nucleotide, amino, fluoro, chloro, bromo, CN, CF, methoxy, imidazole, carboxylate, thioate, C1 to C10 lower alkyl, substituted lower alkyl, alkaryl or aralkyl, OCF3, OCN, O-, S-, or N-alkyl; O-, S-, or N-alkenyl; SOCH3; SO2CH3; ONO2; NO2, N3; heterocycloalkyl; heterocycloalkaryl; aminoalkylamino; polyalkylamino or substituted silyl, as, among others, described in European patents EP 586,520 and EP 618,925.

Chemical Modifications siNA molecules optionally may contain one or more chemical modifications to one or more nucleotides. There is no requirement that chemical modifications are of the same type or in the same location on each of the siNA strands. Thus, each of the sense and antisense strands of an siNA may contain a mixture of modified and unmodified nucleotides. Modifications may be made for any suitable purpose including, for example, to increase RNAi activity, increase the in vivo stability of the molecules (e.g., when present in the blood), and/or to increase bioavailability.

Suitable modifications include, for example, internucleotide or internucleoside linkages, dideoxyribonucleotides, 2'-sugar modification including amino, fluoro, methoxy, alkoxy and alkyl modifications; 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, biotin group, and terminal glyceryl and/or inverted deoxy abasic residue incorporation, sterically hindered molecules, such as fluorescent molecules and the like. Other nucleotides modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidi-ne (d4T) and the monophosphate nucleotides of 3'-azido-3'-deoxythymidine (AZT), 2',3'-dideoxy-3'-thiacytidine (3TC) and 2',3'-didehydro-2',3'-dide-oxythymidine (d4T).

Other suitable modifications include, for example, locked nucleic acid (LNA) nucleotides (e.g., 2'-O, 4'-C-methylene-(D-ribofuranosyl) nucleotides); 2'-methoxyethoxy (MOE)

nucleotides; 2'-methyl-thio-ethyl, 2'-deoxy-2'-fluoro nucleotides, 2'-deoxy-2'-chloro nucleotides, 2'-azido nucleotides, and 2'-O-methyl nucleotides (WO 00/47599, WO 99/14226, WO 98/39352, and WO 2004/083430).

Chemical modifications also include terminal modifications on the 5' and/or 3' part of the oligonucleotides and are also known as capping moieties. Such terminal modifications are selected from a nucleotide, a modified nucleotide, a lipid, a peptide, and a sugar.

Chemical modifications also include L-nucleotides. Optionally, the L-nucleotides may further include at least one sugar or base modification and/or a backbone modification as described herein.

Delivery of Nucleic Acid-Containing Pharmaceutical Formulations

Nucleic acid molecules disclosed herein (including siNAs and Dicer substrates) may be administered with a carrier or diluent or with a delivery vehicle which facilitate entry to the cell. Suitable delivery vehicles include, for example, viral vectors, viral particles, liposome formulations, and lipofectin.

Methods for the delivery of nucleic acid molecules are described in Akhtar et al., Trends Cell Bio., 2: 139 (1992); Delivery Strategies for Antisense Oligonucleotide Therapeutics, ed. Akhtar, (1995), Maurer et al., Mol. Membr. Biol., 16: 129-140 (1999); Hofland and Huang, Handb. Exp. Pharmacol., 137: 165-192 (1999); and Lee et al., ACS Symp. Ser., 752: 184-192 (2000); U.S. Pat. Nos. 6,395,713; 6,235,310; 5,225,182; 5,169,383; 5,167,616; 4,959217; 4,925,678; 4,487,603; and 4,486,194; WO 94/02595; WO 00/03683; WO 02/08754; and U.S. 2003/077829.

Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see e.g., Gonzalez et al., Bioconjugate Chem., 10: 1068-1074 (1999); WO 03/47518; and WO 03/46185), poly (lactic-co-glycolic)acid (PLGA) and PLCA microspheres (see for example U.S. Pat. No. 6,447,796 and U.S. 2002/130430), biodegradable nanocapsules, and bioadhesive microspheres, or by proteinaceous vectors (WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., Clin. Cancer Res., 5: 2330-2337 (1999) and WO 99/31262. The molecules of the instant invention can be used as pharmaceutical agents.

Nucleic acid molecules may be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers. Delivery systems include surface-modified liposomes containing poly (ethylene glycol) lipids (PEG-modified, or long-circulating liposomes or stealth liposomes).

Nucleic acid molecules may be formulated or complexed with polyethylenimine (e.g., linear or branched PEI) and/or polyethylenimine derivatives, including for example poly-ethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives, grafted PEIs such as galactose PEI, cholesterol PEI, antibody derivatized PEI, and polyethylene glycol PEI (PEG-PEI) derivatives thereof (see, for example Ogris et al., 2001, AAPA PharmSci, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999, PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; U.S. Pat. No. 6,586,524 and U.S. 2003/0077829).

Delivery systems may include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in this invention include the following: (1) CellFectin, 1:1.5 (M/M) liposome formulation of the cationic lipid N,NI,NII, NIII-tetramethyl-N,NI,NII,NIII-tetrapalmit-y-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniumm-ethylsulfate) (Boehringer Manheim); and (4) Lipofectamine, 3:1 (M/M) liposome formulation of the polycationic lipid DOSPA, the neutral lipid DOPE (GIBCO BRL) and Di-Alkylated Amino Acid (DiLA2).

Therapeutic nucleic acid molecules may be expressed from transcription units inserted into DNA or RNA vectors. Recombinant vectors can be DNA plasmids or viral vectors. Nucleic acid molecule expressing viral vectors can be constructed based on, but not limited to, adeno-associated virus, retrovirus, adenovirus, or alphavirus. The recombinant vectors are capable of expressing the nucleic acid molecules either permanently or transiently in target cells. Delivery of nucleic acid molecule expressing vectors can be systemic, such as by intravenous, subcutaneous, or intramuscular administration.

Expression vectors may include a nucleic acid sequence encoding at least one nucleic acid molecule disclosed herein, in a manner which allows expression of the nucleic acid molecule. For example, the vector may contain sequence(s) encoding both strands of a nucleic acid molecule that include a duplex. The vector can also contain sequence(s) encoding a single nucleic acid molecule that is self-complementary and thus forms a nucleic acid molecule. Non-limiting examples of such expression vectors are described in Paul et al., 2002, Nature Biotechnology, 19, 505; Miyagi-shi and Taira, 2002, Nature Biotechnology, 19, 497; Lee et al., 2002, Nature Biotechnology, 19, 500; and Novina et al., 2002, Nature Medicine. An expression vector may encode one or both strands of a nucleic acid duplex, or a single self-complementary strand that self hybridizes into a nucleic acid duplex. The nucleic acid sequences encoding nucleic acid molecules can be operably linked to a transcriptional regulatory element that results expression of the nucleic acid molecule in the target cell. Transcriptional regulatory elements may include one or more transcription initiation regions (e.g., eukaryotic pol I, II or III initiation region) and/or transcription termination regions (e.g., eukaryotic pol I, II or III termination region). The vector can optionally include an open reading frame (ORF) for a protein operably linked on the 5' side or the 3'-side of the sequence encoding the nucleic acid molecule; and/or an intron (intervening sequences).

The nucleic acid molecules or the vector construct can be introduced into the cell using suitable formulations. One preferable formulation is with a lipid formulation such as in Lipofectamine™ 2000 (Invitrogen, CA, USA), vitamin A coupled liposomes (Sato et al. Nat Biotechnol 2008; 26:431-442, PCT Patent Publication No. WO 2006/068232). Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate dsRNA in a buffer or saline solution and directly inject the formulated dsRNA into cells, as in studies with oocytes. The direct injection of dsRNA duplexes may also be done. Suitable methods of introducing dsRNA are provided, for example, in U.S. 2004/0203145 and U.S. 20070265220.

Polymeric nanocapsules or microcapsules facilitate transport and release of the encapsulated or bound dsRNA into the cell. They include polymeric and monomeric materials, especially including polybutylcyanoacrylate. The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Nucleic acid moles may be formulated as a microemulsion. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system. Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

EXAMPLES

The present methods, thus generally described, will be understood more readily by reference to the following examples, which are provided by way of illustration and are not intended to be limiting of the present methods and kits.

Example 1: miR-211 is Expressed at a Low Level in Non-Pigmented Melanoma Cell Lines The human epidermal melanocyte cell line HEM-1 (ScienCell™, Catalog #2200) and primary epidermal melancyctes-neonatal (ATCC-PCS-200-012) were grown in MelM media containing MelGS growth supplements, 0.5% FBS, and pen/strep solution. The melanoma cell lines examined included: A375 (stage 4, ATCC® Number: CRL-1619), G361 (stage 4, ATCC), LOX-IMV1 (stage 4, ATCC), HT-144 (stage 4, ATCC® Number: HTB-63), RPMI-7951 (stage 4, ATCC® Number: HTB-66), SK-MEL2 (stage 4, ATCC), SK-MEL28 (stage 3, ATCC), WM793B (stage 1, ATCC® Number: CRL-2806), and WM1552C (stage 3, ATCC® Number: CRL-2808). All melanoma cell lines were grown in Complete Tu Media containing a 4:1 mixture of MCDB-153 medium with 1.5 g/L sodium bicarbonate and Leibovitz's L-15 medium with 2 mM L-glutamine, 2% FBS, and 1.68 mM $CaCl_2$.

Information regarding all clinical samples, derived from frozen samples, is described in Table 1.

TABLE 1

| Clinical Sample # | Tumor Type |
| --- | --- |
| 1 | Nodal Metastasis |
| 2 | Nodal Metastasis |
| 3 | Regional Metastasis |
| 4 | Nodal Metastasis |
| 5 | Nodal Metastasis |
| 6 | Regional Metastasis |
| 7 | Nodal Metastasis |
| 8 | Nodal Metastasis |
| 9 | Distant Metastasis |
| 10 | Primary Melanoma |
| 11 | Nodal Metastasis |
| 12 | Nodal Metastasis |
| 13 | Distant Metastasis |
| 14 | Primary Melanoma |
| 15 | Nodal Metastasis |
| 16 | Nodal Metastasis |
| 17 | Distant Metastasis |
| 18 | Distant Metastasis |
| 19 | Nodal Metastasis |
| 20 | Nodal Metastasis |
| 21 | Primary Melanoma |
| 22 | Primary Melanoma |
| 23 | Primary Melanoma |
| 24 | Primary Melanoma |
| 25 | Distant Metastasis |
| 26 | Distant Metastasis |
| 27 | Regional Metastasis |
| 28 | Regional Metastasis |
| 29 | Regional Metastasis |
| 30 | Regional Metastasis | miRNA NCode™ version 2 array (Invitrogen) containing 553 human and 427 mouse miRNAs, and the TILDA array (ABI) were used for miRNA expression profiling. The miRNA samples were labelled with AlexaFluor® conjugated dendrimers using the direct labelling kit (Genisphere). Hybridization conditions were routinely assessed by discriminating between 2 nt variants at internal sites, and most probes can distinguish between 1 nt variants. The arrays were scanned with Axon B-4000 (Agilent).

Expression levels of all statistically significant and differentially expressed mRNAs and miRNAs were confirmed by qRT-PCR using TaqMan® expression kits (Applied Biosystems) [65] using multiple technical and biological replicates. GAPDH was used as the internal reference probe for normalization of expression values of mRNA, and RNU48 was used for normalization of miRNA. RNA analysis by Northern blots used 20 μg of total RNA concentrated from each sample (melanoma cell lines and melanocytes), separated on 15% urea denaturing polyacrylamide gels by electrophoresis. Gels were electroblotted to nylon membranes, cross-linked by UV, prehybridized in ULTRAhyb®-Oligo (Ambion) for 30 minutes at 42° C., and hybridized with 5'-biotinylated anti-miRNA DNA oligonucleotides (100 nM each) at 42° C. overnight, washed, and detected by chemiluminescence (Brightstar® detection kit, Ambion). Anti-U6 probes were used as a reference control (at 10 pM).

Figure 2:
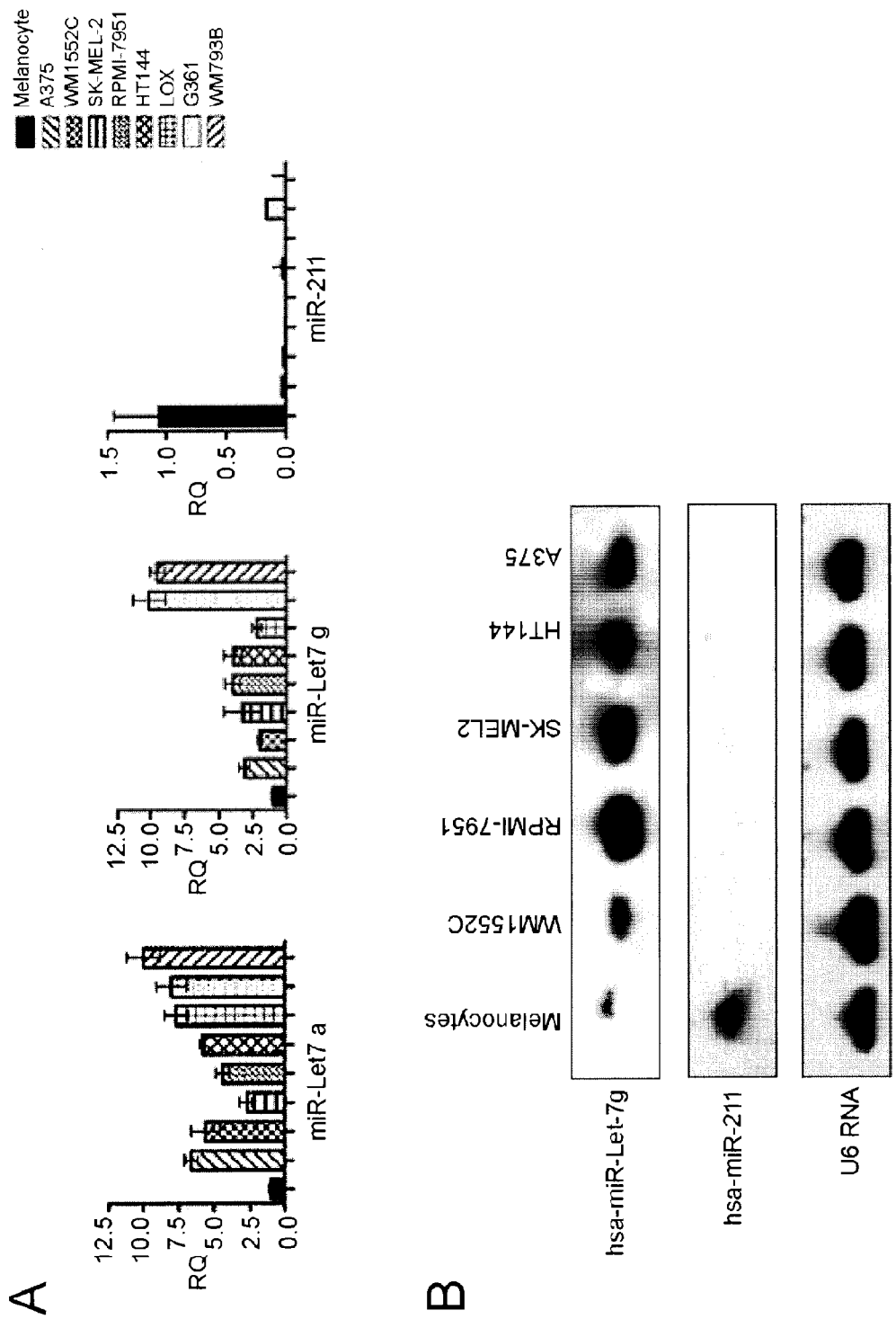
FIG. 2(A) is a series of bar graphs showing levels of individual miRNAs as measured by qRT-PCR in eight different melanoma cell lines, and (B) is a photograph of the northern blot analysis of miR-211 and miR-let-7g in five melanoma cell lines and melanocytes.

As the first step in identifying down-regulated miRNAs in human melanoma, significantly differentially expressed miRNA species were identified in the melanoma cell line WM1552C (originally established from a stage 3 skin melanoma of a 72-year-old patient) compared to those in the normal melanocyte cell line HEM-1 by hybridization of total RNA samples to miRNA probe arrays (see Methods). FIG. 1 lists 24 statistically significant differentially expressed miRNAs, classified into three groups according to their significance levels (P<0.01, 0.02, and 0.05, respectively) (see also Table 2). To address whether the differential miRNA expression levels observed with WM1552C varied among other established melanoma cell lines, we performed quantitative reverse transcriptase mediated polymerase chain reaction (qRT-PCR) analysis on RNA isolated from WM1552C and seven additional non-pigmented melanoma cell lines (FIG. 2A), addressing the expression levels of three separate microRNAs: miR-let7a, miR-let7g, which were over-expressed, and miR-211 was down-regulated. Northern blot analysis further confirmed these results (FIG. 2B). This consistency provided the opportunity to address the significance of the reduced level of miR-211 in melanoma. Next, the role of their target genes that are thus up-regulated in melanoma was determined. miR-211 showed the most robust and consistent changes in expression levels between melanocytes and non-pigmented melanoma cell lines. Results reported in FIGS. 1-2 implicate several additional miRNAs in melanoma that will not be discussed herein.

TABLE 2

| | | |
|---|---|---|
| SEQ ID NO: 1 | miR-let-7a | UGAGGUAGUAGGUUGUAUAGUU |
| SEQ ID NO: 2 | miR-let-7b | UGAGGUAGUAGGUUGUGUGGUU |
| SEQ ID NO: 3 | miR-let-7c | UGAGGUAGUAGGUUGUAUGGUU |
| SEQ ID NO: 4 | miR-let 7d | AGAGGUAGUAGGUUGCAUAGUU |
| SEQ ID NO: 5 | miR-let-7e | UGAGGUAGGAGGUUGUAUAGUU |
| SEQ ID NO: 6 | miR-let-7f | UGAGGUAGUAGAUUGUAUAGUU |
| SEQ ID NO: 7 | miR-let-7g | UGAGGUAGUAGUUUGUACAGUU |
| SEQ ID NO: 8 | miR-let-7i | UGAGGUAGUAGUUUGUGCUGUU |
| SEQ ID NO: 9 | miR-125a | UCCCUGAGACCCUUUAACCUGUGA |
| SEQ ID NO: 10 | miR-125b | UCCCUGAGACCCUAACUUGUGA |
| SEQ ID NO: 11 | miR-15b | UAGCAGCACAUCAUGGUUUACA |
| SEQ ID NO: 12 | miR-16-1 | UAGCAGCACGUAAAUAUUGGCG |
| SEQ ID NO: 13 | miR-199a | CCCAGUGUUCAGACUACCUGUUC |

TABLE 2-continued

| | | |
|---|---|---|
| SEQ ID NO: 14 | miR-21 | UAGCUUAUCAGACUGAUGUUGA |
| SEQ ID NO: 15 | miR-211 | UUCCCUUUGUCAUCCUUCGCCU |
| SEQ ID NO: 16 | miR-214 | ACAGCAGGCACAGACAGGCAGU |
| SEQ ID NO: 17 | miR-221 | AGCUACAUUGUCUGCUGGGUUUC |
| SEQ ID NO: 18 | miR-222 | AGCUACAUCUGGCUACUGGGU |
| SEQ ID NO: 19 | miR-23a | AUCACAUUGCCAGGGAUUUCC |
| SEQ ID NO: 20 | miR-23b | AUCACAUUGCCAGGGAUUACC |
| SEQ ID NO: 21 | miR-26a | CCUAUUCUUGGUUACUUGCACG |
| SEQ ID NO: 22 | miR-30c | UGUAAACAUCCUACACUCUCAGC |
| SEQ ID NO: 23 | miR-320 | AAAAGCUGGGUUGAGAGGGCGA |
| SEQ ID NO: 24 | miR-99a | AACCCGUAGAUCCGAUCUUGUG |

Figure 3:
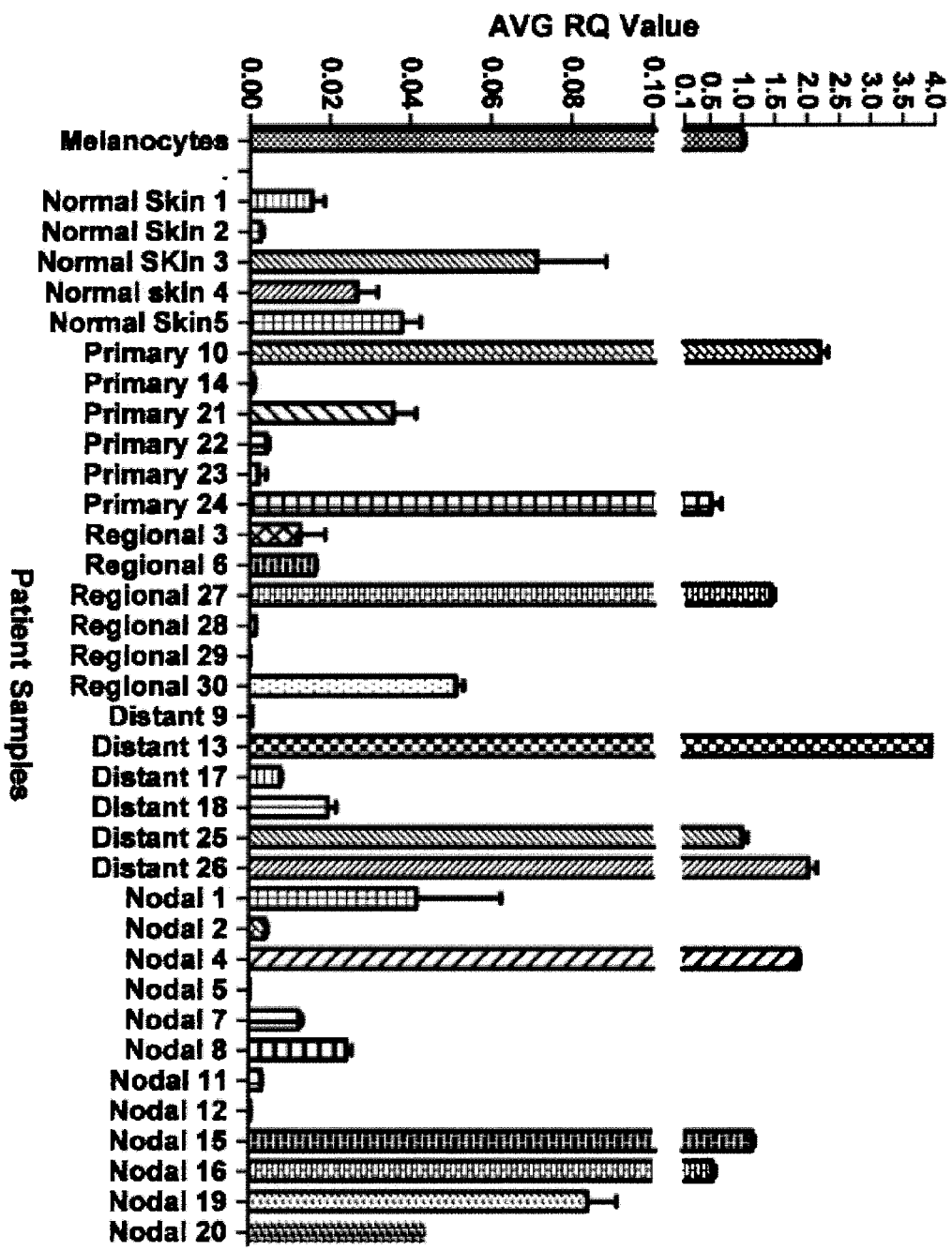
FIG. 3 is a bar graph showing normalized ratios of miR-211 levels in clinical samples relative to its level in a melanocyte cell line as measured by qRT-PCR.

Example 2: miR-211 Levels in Clinical Melanoma Samples miR-211 transcript levels were assayed by qRT-PCR in 30 clinical melanoma samples (six primary, six regional, 12 nodal and six distal metastatic, respectively; described in Table S1). miR-211 expression levels were reduced in 21 of these clinical samples compared to that observed in melanocytes (FIG. 3, Table 3). In the remaining nine melanomas, six (one primary, one regional, two distant, and two nodal metastatic melanomas) showed statistically significant increases in miR-211 expression, whereas expression was not significantly different in the remaining samples. These samples were obtained from different patients; therefore, the observed differences may reflect different processes in melanoma development and progression, individual genetic differences, different proportions of non-melanoma (including non-pigmented) cells in the tumor samples, or a combination of these factors. miR-211 levels were low in the majority (21/30) of the tested melanoma clinical samples, a statistically significant trend (P=0.029, for random distribution by Fisher's exact test) that is consistent with the uniformly low expression levels in all eight melanoma-derived cell lines we studied. Note that miR-211 expression levels were also observed to be low in normal skin samples, which is expected given that melanocytes constitute a minor fraction of skin cells. Additional miRNAs that were over-expressed in melanoma cell lines relative to those in melanocytes were also over-expressed in the clinical melanoma samples but not in the normal skin samples (data not shown), confirming that normal skin samples are not the ideal background controls.

TABLE 3

| miR-211 | | |
|---|---|---|
| Sample | Avg RQ | RQ St Dev |
| Melanocyte | 1.00063 | 0.04371 |
| Primary Melanoma 10 | 2.2066'S | 0.12293 |
| Primary Melanoma 14 | 0.00093 | 0.00041 |
| Primary Melanoma 21 | 0.03565 | 0.00577 |
| Primary Melanoma 22 | 0.00419 | 0.00086 |
| Primary Melanoma 23 | 0.00226 | 0.00189 |
| Primary Melanoma 24 | 0.52232 | 0.15612 |
| Mean Primary Melanoma | 0.02669 | 0.00647 |

TABLE 3-continued miR-211

| Sample | Avg RQ | RQ St Dev |
|---|---|---|
| Regional Metastasis 3 | 0.01264 | 0.00628 |
| Regional Metastasis 6 | 0.0164 | 0.00033 |
| Regional Metastasis 27 | 1.44156 | 0.06496 |
| Regional Metastasis 28 | 0.00155 | 0.00016 |
| Regional Metastasis 29 | 0.00021 | 0.00006 |
| Regional Metastasis 30 | 0.05138 | 0.00201 |
| Mean Regional Metastases | 0.01309 | 0.00116 |
| Distant Metastasis 9 | 0.00095 | 0.00011 |
| Distant Metastasis 13 | 3.93166 | 0.07708 |
| Distant Metastasis 17 | 0.00774 | 0.00049 |
| Distant Metastasis 18 | 0.01958 | 0.00208 |
| Distant Metastasis 25 | 1.00047 | 0.09279 |
| Distant Metastasis 26 | 2.02149 | 0.13435 |
| Mean Distant Metastases | 0.10219 | 0.00692 |
| Nodal Metastasis 1 | 0.04167 | 0.02092 |
| Nodal Metastasis 2 | 0.0042 | 0.00047 |
| Nodal Metastasis 4 | 1.86626 | 0.0325 |
| Nodal Metastasis 5 | 0.00037 | 0.00008 |
| Nodal Metastasis 7 | 0.01243 | 0.00095 |
| Nodal Metastasis 8 | 0.02438 | 0.00144 |
| Nodal Metastasis 11 | 0.00318 | 0.00034 |
| Nodal Metastasis 12 | 0.00061 | 0.00012 |
| Nodal Metastasis 15 | 1.15988 | 0.04215 |
| Nodal Metastasis 16 | 0.55816 | 0.0367 |
| Nodal Metastasis 19 | 0.08403 | 0.00731 |
| Nodal Metastasis 20 | 0.04442 | 0.00172 |
| Mean Nodal Metastases | 0.02729 | 0.00233 |
| Normal Skin 1 | 0.01538 | 0.0033 |
| Normal Skin 2 | 0.00272 | 0.00067 |
| Normal Skin 3 | 0.07133 | 0.01717 |
| Normal Skin 4 | 0.02671 | 0.00515 |
| Normal Skin 5 | 0.03778 | 0.00469 |
| Mean Normal Skin | 0.01976 | 0.00391 |

Figure 10:
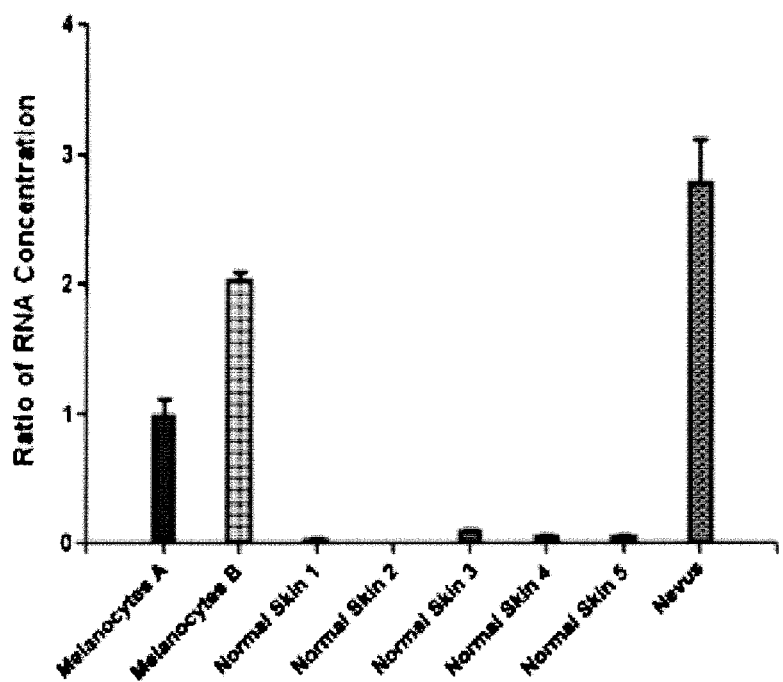
FIG. 10 is a depiction of the higher expression of miR-211 in melanocytes and nevus sample compared to normal skin.

Although there is no perfect "normal" counterpart tissue for melanoma in clinical skin samples, miR-211 expression levels in additional melanocyte cell lines and in five independent isolates of normal skin samples were tested for comparison. Results show that miR-211 is elevated in both melanocyte cell lines compared to normal human skin (FIG. 10). miR-211 expression levels in pooled samples of nevi also agree with previously published results, supporting the observation that miR-211 is highly expressed in nevi compared to melanoma [44]. These observations are consistent with the understanding that nevi are composed of melanocytes. Together, these results suggest that the development of most melanomas is specifically associated with the depletion of miR-211 transcript levels. An alternative formal interpretation, which is unlikely considering the absence of supporting literature, is that the low miR-211 level in melanoma reflects a cellular origin of melanoma which is distinct from that of melanocytes.

Example 3: Stable Ectopic Expression of miR-211 in Melanoma Cell Lines Depletes Select Target Transcripts For the initial transformation of miRNA array data, the GenePixPro 6.0 global normalization method was employed in which images and results are normalized together. Statistical significance tests were Welsh t-test, nonparametric ANOVA, (e.g., to select genes that have significantly less within sample variance compared to between sample variance), and correlation analysis with Pearson's product moment r and Spearman's r. Analysis was controlled for false discovery rate using q-values, with a priori cut off point of 10 percent [66,67]. For mRNA expression array data, commencing with GeneChip R Human Exon 1.0 ST Array (Affymetrix, Inc.) four probes per exon and roughly 40 probes per gene, 7 total arrays were analysed (three arrays for melanocyte RNA, and four arrays for melanoma RNA). Cell files were loaded into Partek® Genomics Suite™ (Partek, Inc. St. Louis, Mo., USA) under the following algorithm constraints: interrogating probes selection, RMA background correction, adjusted for GC content, quintile normalization, log probes using base 2, with probe set summarization of median polish. Quality control assessment indicated clear separation based on the cell type. Gene level analysis use an ANOVA model; $y_j = \mu + T_j + €$, where $\mu$ is the mean expression of the gene, $T_j$ is the tissue type, and $€$ is the error term. The ANOVA model generated a significance level for each probe set, along with the fold change, and imputed gene annotations. miR-211 target set of genes were obtained from public databases [miRanda, miRbase, miR-NAmap, Tarbase, PicTar, Target ScanS, and DIANA MicroTest] and the results from ANOVA were matched to obtain the final target gene list of genes. This target list was imported into Ingenuity Pathway Analysis Version 6.0-1202 (Ingenuity Systems®). A core analysis was run employing direct relationships only, the Ingenuity knowledge base genes as the reference set, and with down-regulators as the defined expression value parameter. All microarray data have been deposited into GEO, and accession number is pending.

Oligonucleotides complementary to the miR-211 genomic sequences (miR-211 pre For-ttccctttgtcatccttcgcct (SEQ ID NO.: 27) and miR-211 pre Rev-aggcgaaggat-gacaaagggaa (SEQ ID NO.: 28), containing HindIII and BamHI sites on their respective 5' and 3' ends) were used to amplify the 110 bp pre-miR-211 sequence from human melanocyte genomic DNA (Amplitaq Gold®, Applied Biosystems) and TOPO®-cloned into the pCR®4-TOPO® vector (Invitrogen). The construct was sequenced, and the pre-hsa-miR-211 fragment was sub-cloned into pcDNA4/myc-HisA (Invitrogen) to create pcDNA4/miR-211. The KCNMA1 siRNA sequence was derived from Silencer® siRNA (Ambion, siRNA ID: 112882) and constructed as long complementary oligos (KCNMA1si For-cgtacttcaat-gacaatatttcaagagaatattgtcattgaagtacgtcttttt (SEQ ID NO.: 29) and KCNMA1si Rev-aaaaaagacgtacttcaatgacaatattctctt-gaaatattgtcattgaagtacg (SEQ ID NO.: 30), containing HindIII and BamHI sites on their respective 5' and 3' ends). The oligos were mixed at 100 μM, heated, and amplified through one round of PCR (Amplitaq Gold®, Applied Biosystems) and then TOPO®-cloned into the pCR®4-TOPO® vector (Invitrogen). Inserts were sequenced and then sub-cloned into pcDNA4/myc-HisA (Invitrogen) to create pcDNA4/shKCNMA1.

$2.5 \times 10^5$ WM1552C or A375 melanoma cells were seeded into a single well of a 6-well plate and transfected overnight with 5 μg pcDNA4/miR-211, pcDNA4/shKCNMA1, or pcDNA4/myc-HisA ("vector only" negative control) using Fugene® 6 (Roche). The transfected cells were selected at 400 or 800 μg/mL Zeocin™ for 15 days, and the presence of the transgene copy in stable Zeocin™-resistant foci was confirmed by PCR (Amplitaq® Gold, Applied Biosystems). Cell lines were named WM1552C/211(400) or A375/211 (400) when selection was at 400 μg/ml Zeocin™, and WM1552C/211(800) when selection was at 800 μg/ml Zeocin™, respectively. The "vector only" control cells were selected at 800 μg/ml Zeocin™. WM1552C/KC KO were selected at 400 μg/ml Zeocin™.

Figure 4:
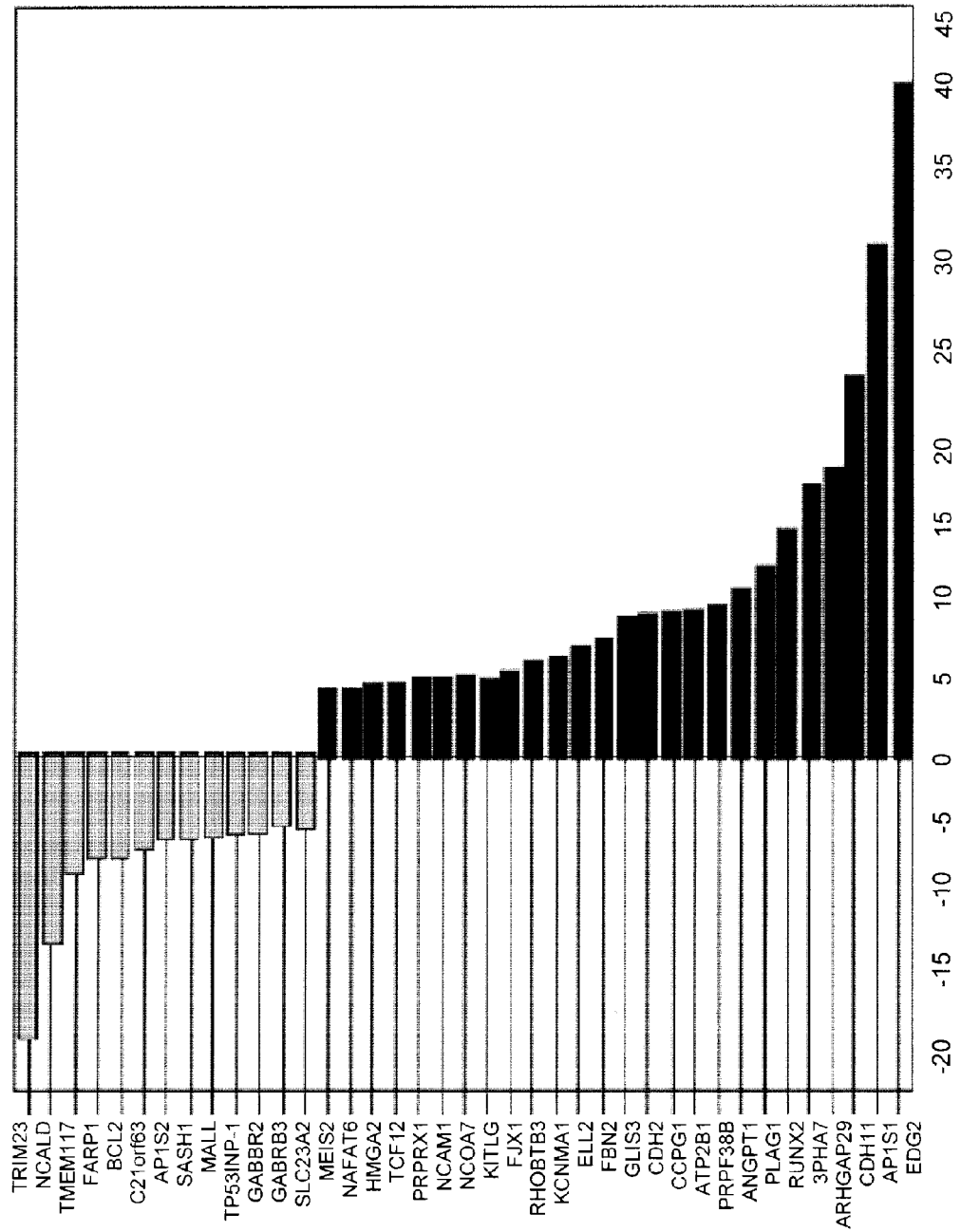
FIG. 4 is a histogram of $\log_2$ transformed expression ratios showing the fold change of mRNAs in WM1552C to those in a melanocyte cell line.

To demonstrate that depleted miRNA in melanoma is biologically relevant, (i.e., mechanistically related to melanoma development as opposed to coincidental) melanoma cells were assessed for enrichment in their target transcripts levels relative to their corresponding levels in melanocytes. As the first step to identify such mRNA transcripts, cDNAs made from total RNA isolated from the melanoma cell line WM1552C and the melanocyte line HEM-1 were hybridized to Affymetrix expression arrays. The hybridization intensity data was then filtered for differential expression of computationally predicted target transcripts of miR-211 (FIG. 4). These experiments revealed 26 putative target transcripts whose expression levels were elevated relative to those in HEM-1.

Figure 5:
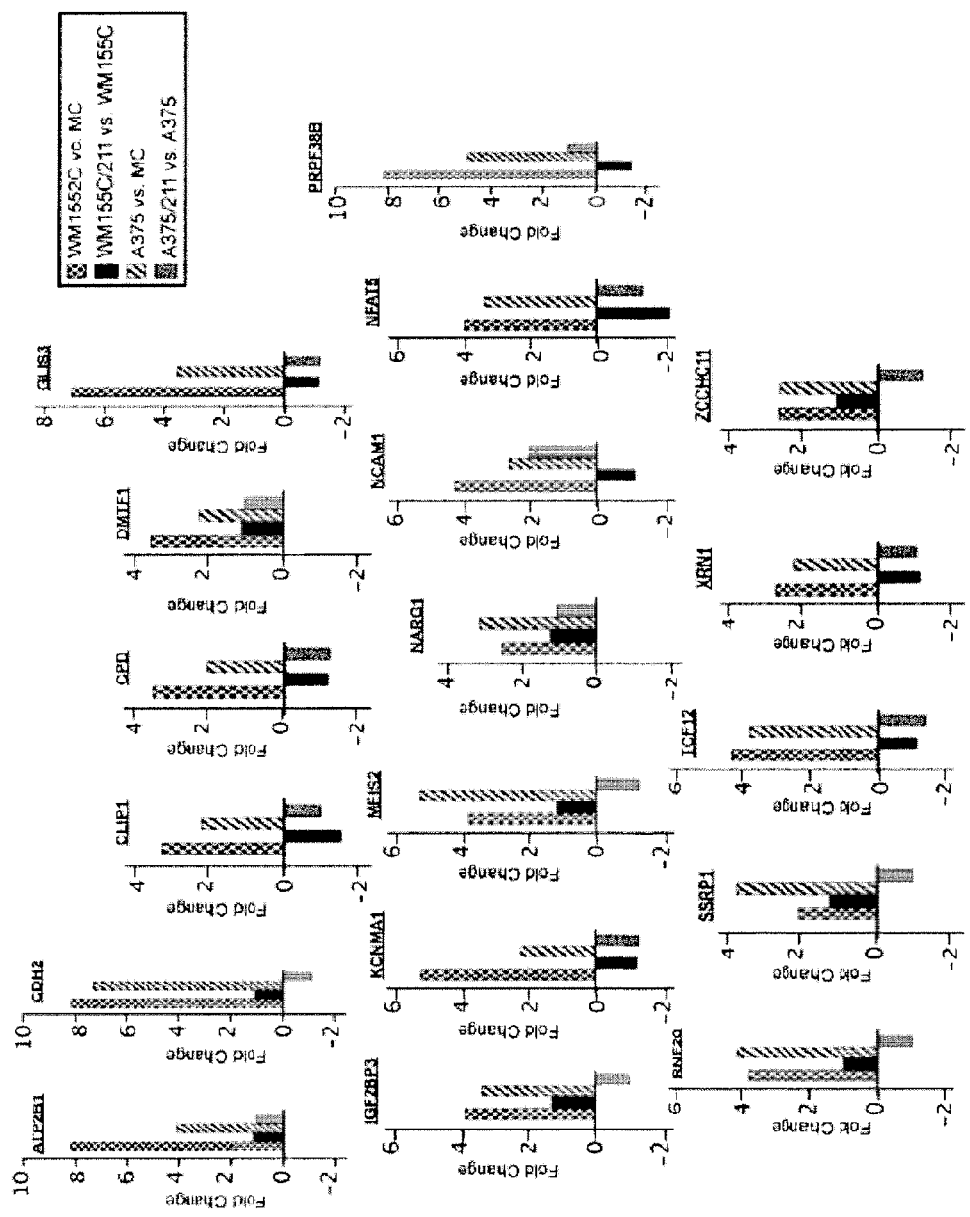
FIG. 5 is a series of bar graphs showing the effects of miR-211 overexpression on KCNMA1 gene expression.

If the set of 26 genes contains valid targets of miR-211, the levels should be depleted if miR-211 levels increase in any melanoma cell line. To directly examine this possibility, three independent melanoma cell lines were constructed that stably express miR-211. For that purpose, the pre-miR-211 sequence (plasmid pcDNA4/miR-211) was transfected into WM1552C and A375 cells, followed by selection for stable expression of miR-211 and confirmation of expression by qRT-PCR analysis. The melanoma cell line clones that ectopically expressed miR-211 were named: WM1552C/211 (400), WM1552C/211(800) and A375/211. Global mRNA levels in WM1552C/211(400) and A375/211 cells were measured on Affymetrix arrays and these levels were compared with the corresponding levels measured in the same experiment in untransfected parental cell lines WM1552C and A375, respectively. This analysis revealed a list of 18 putative target transcripts for miR-211, which were down-regulated by the artificial expression of miR-211 in both melanoma cell lines (FIG. 5). When cross-referenced with results reported in FIG. 4, nine of these putative target transcripts were found to be up-regulated in both melanoma cell lines compared to those in melanocytes and down-regulated in both melanoma cell lines when miR-211 was stably expressed. These candidate targets of miR-211 are: ATP2B1, CDH2, GLIS3, KCNMA1, MEIS2, NCAM-1, NF-AT5, PRPF38B, and TCF12. The expression of KCNMA1, which encodes a component of a K$^+$ exporting channel whose function is modulated by Ca$^+$, has been linked to tumor cell proliferation in prostate cancer [49], cell migration in glioma [56] and antineoplastic drug resistance in melanoma cells [57]. The 3'-UTR of the KCNMA1 transcript also contains one of the strongest predicted target sites of miR-211. Therefore this transcript was the focus of further investigation.

Example 4: KCNMA1 Protein and Transcript Levels Correlate Inversely with that of miR-211

Figure 6:
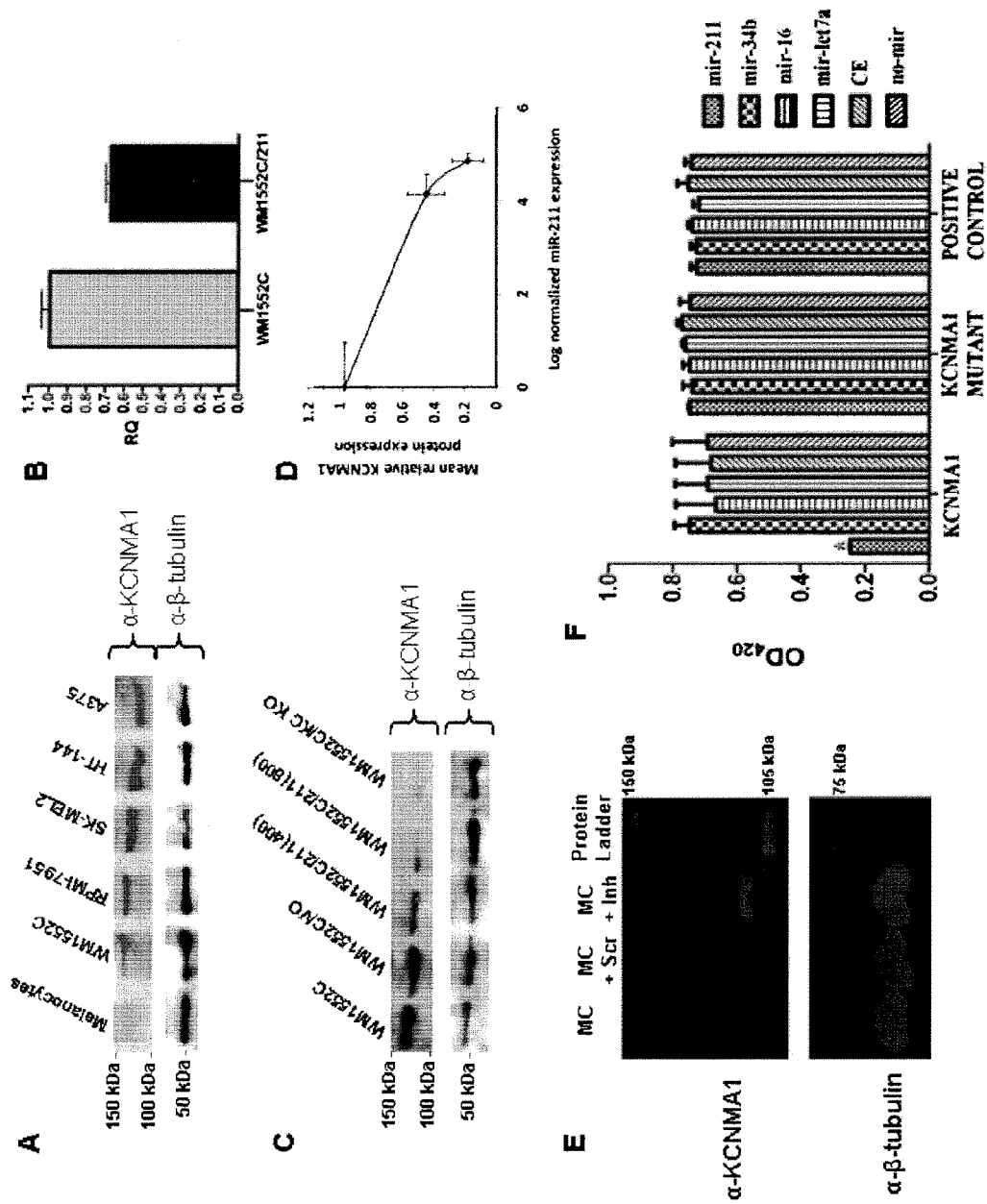
FIG. 6(A) is a photograph of a Western blot analysis of KCNMA1 protein expression in melanocytes and melanoma cells; (B) is a bar graph showing the relative expression of KCNMA1 in mRNA in cells expressing and not expressing miR-211; (C) is a photograph of a Western blot analysis of KCNMA1 protein expression in WM1552C cell lines; (D) is a line graph of the inverse correlation between miR-211 and KCNMA1 protein levels; (E) is two photographs showing the inhibitory effect of miR-211 on KCNMA protein levels; and (F) is a bar graph showing the inhibitory effect of miR-211 on mRNA containing KCNMA1 3'-UTR sequences.
Figure 11:
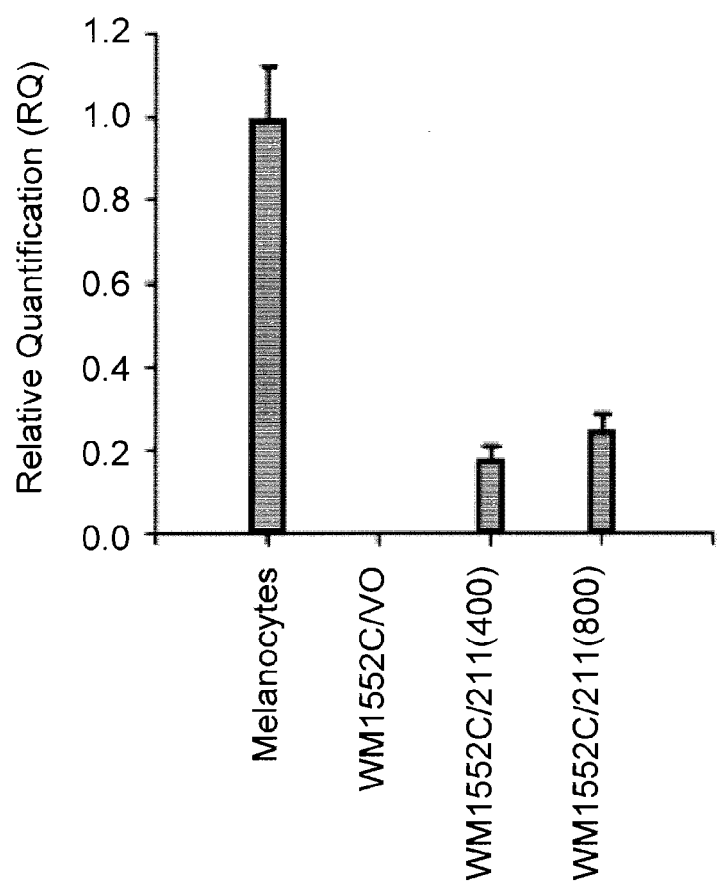
FIG. 11 is a histogram showing miR-211 expression in stable melanoma cell lines compared to melanocytes.

If miR-211 targets the KCNMA1 transcript, KCNMA1 protein expression levels should inversely correlate with that of miR-211 expression levels. A western blot analysis of KCNMA1 expression was performed, utilizing the same cell lines previously examined by northern blot (FIG. 2B) for KCNMA1 transcript expression. KCNMA1 protein expression was very low in normal melanocytes, but high in all melanoma cell lines (FIG. 6A), indicating an inverse correlation of expression between KCNMA1 protein and miR-211.

qRT-PCR analyses were then run to determine whether the induced expression of miR-211 in melanoma cells could reduce KCNMA1 transcript levels. KCNMA1 expression in wild type WM1552C was compared with that in WM1552C/211(400), revealing that the introduction of miR-211 down-regulates the KCNMA1 transcript (FIG. 6B). To further address whether KCNMA1 mRNA levels reflected KCNMA1 protein expression, a western blot analysis was performed looking for KCNMA1 in cell extracts obtained from: 1) WM1552C, 2) WM1552C/VO (WM1552C cells with a stably-incorporated empty expression vector), 3) WM1552C/211(400), 4) WM1552C/211(800), and 5) WM1552C/KC KO (WM1552C cells with a stably-expressing shRNA against the KCNMA1 mRNA) (FIG. 6C). It was found that KCNMA1 protein levels were significantly reduced in both melanoma cell lines expressing miR-211 [even more so in WM1552C/211(800)] compared to those in WM1552C/VO or untransfected WM1552C cells. KCNMA1 was virtually undetectable in the WM1552C/KC KO cell line. These results are consistent with the idea that miR-211 is able to target the KCNMA1 mRNA, thereby decreasing the amount of KCNMA1 protein in the cell. miR-211 expression was measured in engineered melanoma cell lines by qRT-PCR, and it did not exceed the levels observed in, melanocytes (FIG. 11). To further confirm our observations, we measured the correlation between miR-211 expression and KCNMA1 protein levels (FIG. 6D). The results revealed an inverted correlation between miR-211 expression and KCNMA1 protein levels. To confirm that this expression correlation occurred in non-transformed cells in addition to cancerous cell lines, the effect of miR-211 inhibition on the expression of KCNMA1 in melanocytes was examined. Melanocytes were transfected with anti-miR-211 inhibitors (Exiqon) and the protein expression of KCNMA1 was measured. The results indicated that derepression of KCNMA1 protein expression could be achieved by inhibition of miR-211 (FIG. 6E).

Example 5: miR-211 Directly Targets the KCNMA1 Transcript

Figure 12:
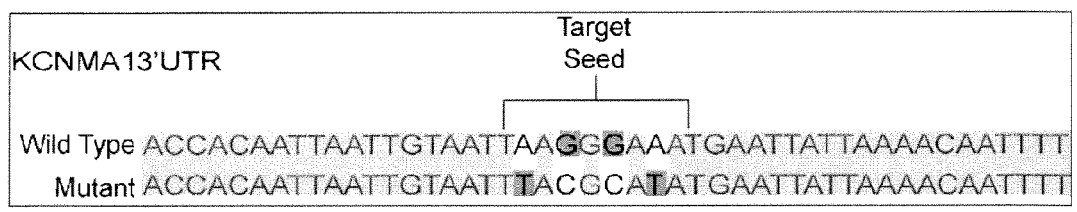
FIG. 12 is a diagram showing mutagenesis of miR-211 target seed sequence in the 3'-UTR of KCNMA1. The wildtype 3'UTR is provided as SEQ ID NO: 25 and the mutant 3'UTR is provided as SEQ ID NO: 26.

The 3' UTR seed sequences of putative target genes were amplified by PCR (Phusion™ PCR kit, Finnzymes) from human melanocyte genomic DNA (Primers: KCNMA1 For-tgcggccgccttccctatatctaaacaatgcaaaatc (SEQ ID NO.: 31), KCNMA1 Rev-aaccggtcacccatccaggcgaggagc (SEQ ID NO.: 32), the primer set contained 5' NotI or 3' AgeI sites). The PCR product was cloned into pCR®4-TOPO® (Invitrogen), confirmed by sequencing, then sub-cloned into the 3' UTR of the LacZ gene in pcDNA6/V5-His/LacZ (Invitrogen) using the 5' NotI and 3' AgeI restriction sites and reconfirmed by sequencing (pcDNA6/LacZ/KCNMA1). The cloned 3'UTR of KCNMA1 was mutated using the primers: KC Mut For-TACGCATATGAATTAT-TAAAACAATTTT (SEQ ID NO.: 33) and KC Mut Rev-TATGCGTAAATTACAATTAATTGTGCT (SEQ ID NO.: 34), and used to PCR amplify pcDNA6/LacZ/KCNMA1 using Quickchange (Stratagene). The plasmid product was then recovered and confirmed by sequencing (pcDNA6/LacZ/KCNMA1-MUT, see FIG. 12 for mutagenesis). A375 melanoma cell lines were then transfected in triplicate (Fugene® 6, Roche) with 5 μg plasmid DNA of: A) pcDNA6/LacZ/KCNMA1, B) pcDNA6/V5-His/KCNMA1-MUT or C) pcDNA6/V5-His/LacZ (positive control), and co-transfected (siPORT™, Ambion) at 100 nM with miRIDIAN microRNA Mimics (Dharmacon) for A) miR-16-1, B) miR-211, C) miR-34b, D) miR-let-7a-1, E) miRIDIAN cel-miR-67 (negative control; cel-miR-67 has been confirmed to have minimal sequence identity with miRNAs in human, mouse, and rat), or F) no mimic miRNA. After overnight incubation, cells were washed in PBS and reincubated in fresh media. After 48 hours, cells were harvested by trypsinization, examined for viability, and samples were prepared for the β-galactosidase assay using the β-Gal Assay kit (Invitrogen). Samples were incubated overnight at 37°

C., then assayed for β-galactosidase activity in a 96-well plate format using a FlexStation3 (Molecular Devices).

To determine whether the computationally predicted target site of miR-211 in the 3'-UTR of the KCNMA1 transcript confers sensitivity to miR-211, a target cleavage assay was performed with a construct containing the 3'-UTR of KCNMA1 cDNA fused downstream of the reporter gene β-galactosidase. The construct, pcDNA6/LacZ/KCNMA1, as well as a derivative, pcDNA6/LacZ/KCNMA1-MUT (containing a mutated target cleavage site at the seed sequence; see Figure S3), and the control vector pcDNA6/LacZ, were separately transfected into A375 cells along with one of the following miRNA mimics: miR-211, miR-16-1, miR-34b, miR-let-7a-1, cel-miR-67, or no mimic (FIG. 6E). The results revealed a statistically significant drop of nearly 60% in β-galactosidase activity when the cells were transfected with pcDNA6/LacZ/KCNMA1 together with miR-211 mimics, but not with any other combination. Importantly, this drop was not detectable in cells co-transfected with pcDNA6/LacZ/KCNMA1-MUT and the miR-211 mimic, demonstrating that miR-211 was capable of specifically targeting the wild type seed sequence in the 3'-UTR of the KCNMA1 transcript.

Example 6: MITF Coordinately Regulates miR-211 and TRPM1

Figure 7:
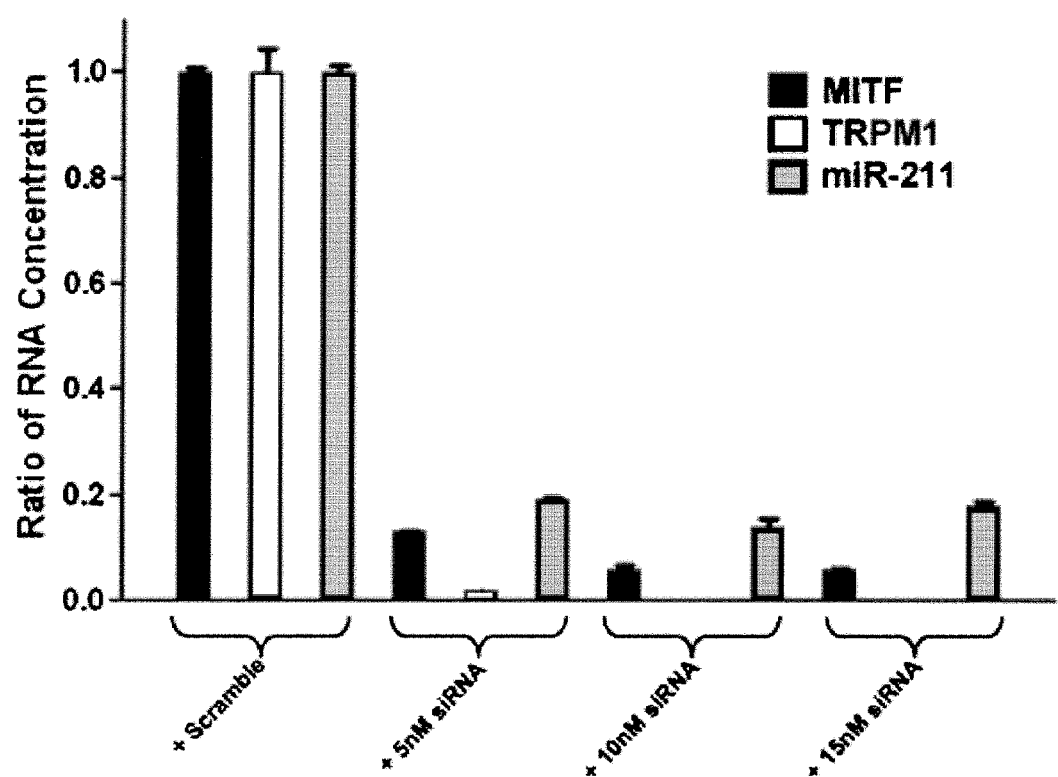
FIG. 7 is a bar graph showing the effect of MITF knock-down on TRPM1 and miR-211 expression in melanoma cells.

The gene encoding miR-211 is located within the sixth intron of the TRPM1 gene, which encodes multiple polypeptide isoforms including melastatin-1, a transient receptor potential (TRP) protein family member thought to be a potential suppressor of melanoma metastasis [58]. However, the molecular basis of the tumor suppressor activity of TRPM1 gene is not understood. The transcription factor MITF regulates the expression of TRPM1 gene, where the MITF-binding motif (GCTCACATGT) (SEQ ID NO.: 35) is located in the TRPM1 promoter [58]. In order to determine whether MITF also might transcriptionally regulate miR-211 expression via the TRPM1 promoter, it was determined that both TRPM1 and miR-211 transcripts are expressed in pigmented but not in the non-pigmented melanoma cells. To determine whether MITF expression modulates miR-211 expression, MITF expression was knocked down by siRNA in the pigmented melanoma cell line SK-MEL28. Three different doses of siRNA (5 nM, 10 nM and 15 nM) were used, and the knock-down efficiency was measured by qRT-PCR. As expected, the extent of reduction in MITF transcript levels directly correlated with the reduction in TRPM1 and miR-211 transcript levels (FIG. 7). These results suggest that MITF co-ordinately regulates TRPM1 and miR-211 expression. It also suggests that one of the ways MITF might also suppress melanoma metastasis is through its transcriptional activation of miR-211 via the TRPM1 promoter, and the consequent negative post-transcriptional effects of miR-211 on KCNMA1 mRNA.

Example 7: The Effect of miR-211 on Cell Proliferation and Invasion

Proliferation

Figure 8A:
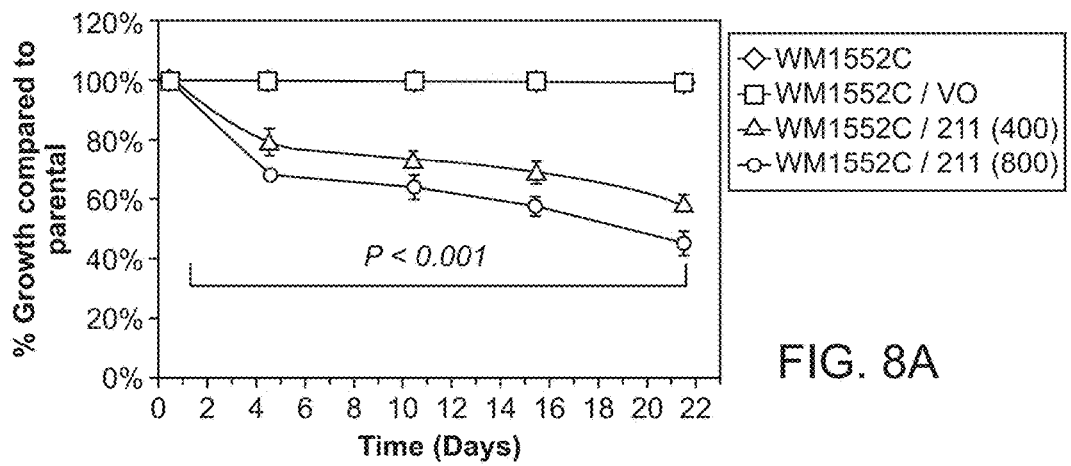
FIGS. 8(A) and (B) are line graphs of relative mean cell titers; (C) is a series of photographs of cell invasion assays; (D) is a bar graph showing the results of cell invasion assays; and (E) is a bar graph and photograph showing the effect on melanoma cell invasiveness by KCNMA1 protein expression.
Figure 8B:
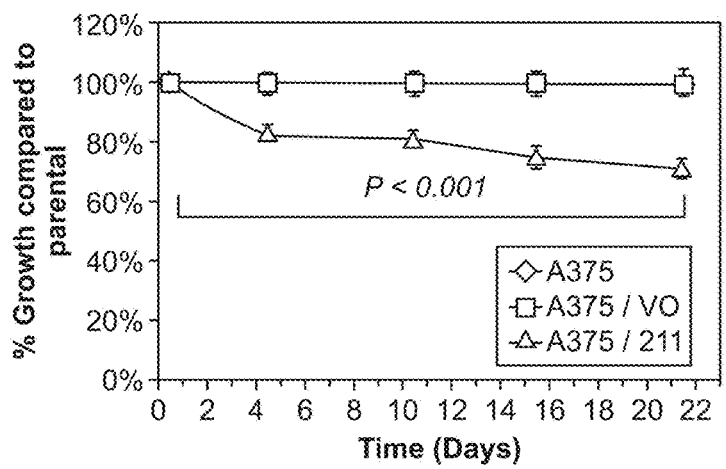

The over-expression of KCNMA1 is often associated with both cell proliferation and cell migration/invasion in various cancers [49-51]. Therefore, the effects of depletion of miR-211 and associated over-expression of KCNMA1 on these process in melanoma cells were determined. Proliferation rates of melanoma cell lines stably transfected with the miR-211 expression cassette were compared with those of untransfected melanoma cells and cell lines transfected with the empty expression vector (FIG. 8A), respectively. All miR-211-expressing cultures of WM1552C/211 showed reduced cell counts compared to those of WM1552C beginning at even the first time point (day 4), and the titer continued to fall behind as time progressed. After a 21-day period, WM1552C/211(400) had greater than 30% decrease in cell counts compared to those of WM1552C, while WM1552C/211(800) cultures showed an even greater decrease in cell proliferation. WM1552C/VO cells showed no significant difference in cell proliferation compared to WM1552C. Comparable results were obtained for cell proliferation of A375/211 cell lines, which grew more slowly than untransfected A375 or A375/VO (FIG. 8B). These results are consistent with the hypothesis that an important growth stimulatory event in the melanoma cell lines WM1552C and A375 involves the depletion of miR-211 levels—the latter possibly leading to the targeted up-regulation of at least KCNMA1 expression among its target genes.

Invasion

Total lysates of $5 \times 10^5$ cells of each cell line were boiled under denaturing conditions and proteins separated on 6% Tris-Glycine denaturing polyacrylamide gels by electrophoresis. Proteins transferred to nitrocellulose membranes were probed with the following primary antibodies: anti-Slo1 (NeuroMab, UC Davis) at $\frac{1}{500}$ and anti-β-tubulin (BD Pharmingen) at $\frac{1}{2000}$ according to standard methods. Blots were probed with horseradish peroxidase-conjugated secondary antibodies and visualized with ECL chemiluminescence (Pierce) or Alexa 680-conjugated secondary antibodies (Molecular Probes) and visualized on the Licor Odyssesy (Licor).

Assays were performed using WM1552C, WM1552C/VO, WM1552C/211(400), WM1552C/211(800), A375, A375/VO, and A375/211 cell lines. Cells were grown in log phase, trypsinized, counted using an automated cell counter (Cellometer®, Nexcelom Bioscience), and then seeded into 75 cm² flasks at $5 \times 10^5$ cells per flask (in triplicate). Media was changed after 6 hours, and cells were further fed every 48 hours (Complete Tu Media). At days 4, 10, 15, and 21, cells were trypsinized, counted (Cellometer®, Nexcelom Bioscience), and then reseeded. Each assay was performed in duplicate for all cell lines.

BD BioCoat™ growth factor reduced insert plates (Matrigel™ Invasion Chamber 12 well plates) were prepared by rehydrating the BD Matrigel™ matrix coating in the inserts with 0.5 mls of serum-free Complete Tu media for two hours at 37° C. The rehydration solution was carefully removed from the inserts, 0.5 ml Complete Tu (2% FBS) was added to the lower wells of the plate, and $2.5 \times 10^4$ cells suspended in 0.5 ml of serum-free Complete Tu media were added to each insert well. WM1552C/211(800) cells were additionally transfected with the Anti-miR miRNA Inhibitor for hsa-miR-211 as well as Negative Control #1 (Ambion) (miR-Scramble) at a concentration of 100 nM using siPORT NeoFX (Ambion). Invasion assay plates were incubated for 48 hours at 37° C. Following incubation, the non-invading cells were removed by scrubbing the upper surface of the insert. The cells on the lower surface of the insert were stained with crystal violet, and each trans-well membrane was mounted on a microscope slide for visualization and analysis. The slides were scanned using the Aperio Scanscope XT and visualized using the Aperio Imagescope v10 software. The number of migrating tumor cells was counted from each of five images per cell line (including miR Inhibitor transfected cells) in the central area of the filter. Cell lines were tested in triplicate, and the assays were performed twice. Data are expressed as the percent invasion through the membrane relative to the migration of WM1552C (Wild Type) through the membrane.

$5 \times 10^5$ HEM-1 cells were seeded into wells of a 6-well plate. The cells were then transfected with Fugene® 6 (Roche) and either 100 nM of anti-miR-211 Inhibitors (Exiqon), 100 nM of anti-miR Inhibiter Negative Control #1 ("miR-Scramble"), or transfection agent only. After 48 hours, the cells were harvested by trypsinization and counted using an automated cell counter (Cellometer®, Nexcelom Bioscience). $2.5 \times 10^5$ cells were then prepared for western blotting (as above).

Figure 8C:
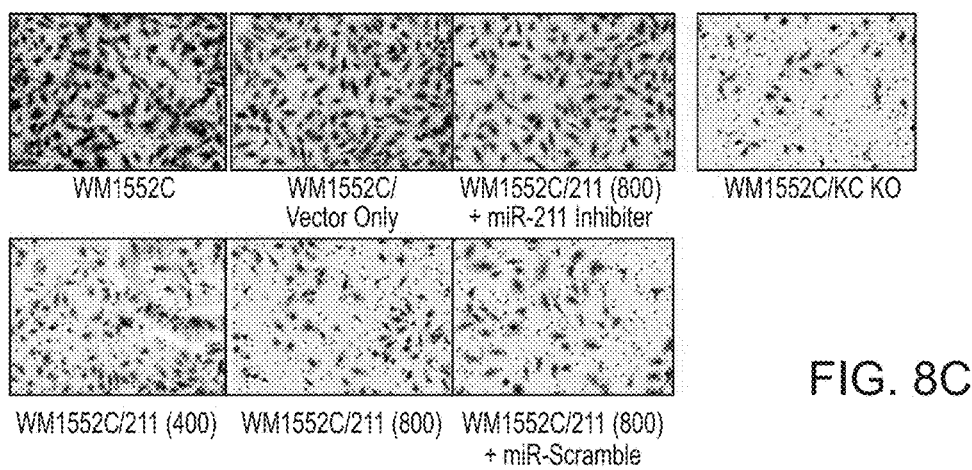
Figure 8D:
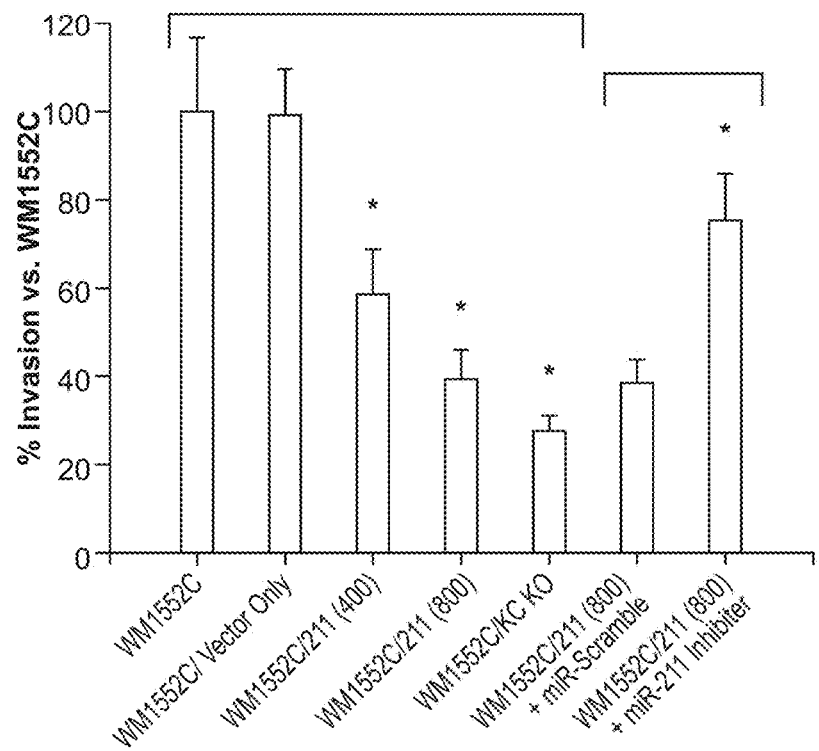

The impact of miR-211 expression on the invasive properties of WM1552C. WM1552C/211(400) and WM1552C/211(800) cells, along with WM1552C/VO, WM1552C/KC KO, and untransfected WM1552C was determined. Cells were seeded separately into invasion chambers, and the cells were allowed to migrate as described above. Results indicated that WM1552C/211(400) and WM1552C/211(800) cells migrated significantly less (~40% and 60% less, respectively) than WM1552C (FIGS. 8C and 8D), whereas WM1552C/VO cells showed almost no variation compared to parental cells. The frequency of cells with invasion defects significantly exceeded the decrease in the proliferation rates of these cells (an ~8-10% decrease in growth over the 48 hours of the invasion assay period), suggesting that the two effects on miR-211 expression are independent of each other. The most significant effect on invasion was observed in the WM1552C/KC KO cells. While a sequence-scrambled oligonucleotide (miR-Scramble) did not show an effect on cell invasion, cells treated with a miR-211 inhibitor restored the invasion phenotype by as much as 40% (FIG. 8D). Given that previously published evidence directly links KCNMA1 gene dosage and/or expression with increased motility/invasion in several cancers [49-51], these results suggest that at least part of the invasion defect caused by miR-211 in melanoma cell lines is due to targeted down-regulation of the KCNMA1 transcript.

Effect of KCNMA1 on Proliferative and Invasive Functions $2.5 \times 10^5$ cells WM1552C/211(800) cells were seeded into wells of a 6-well plate. 1 well was transfected with 5 µg of KCNMA1-expressing plasmid (Origene catalog #SC122078) using Fugene® 6 (Roche) and a second well was treated with transfection reagent only. After 48 hours, the cells were harvested by trypsinization and counted using an automated cell counter (Cellometer®, Nexcelom Bioscience). $2.5 \times 10^4$ cells were then utilized for invasion assays (in triplicate) and $2.5 \times 10^5$ cells were prepared for western blotting (as above).

Figure 8E:
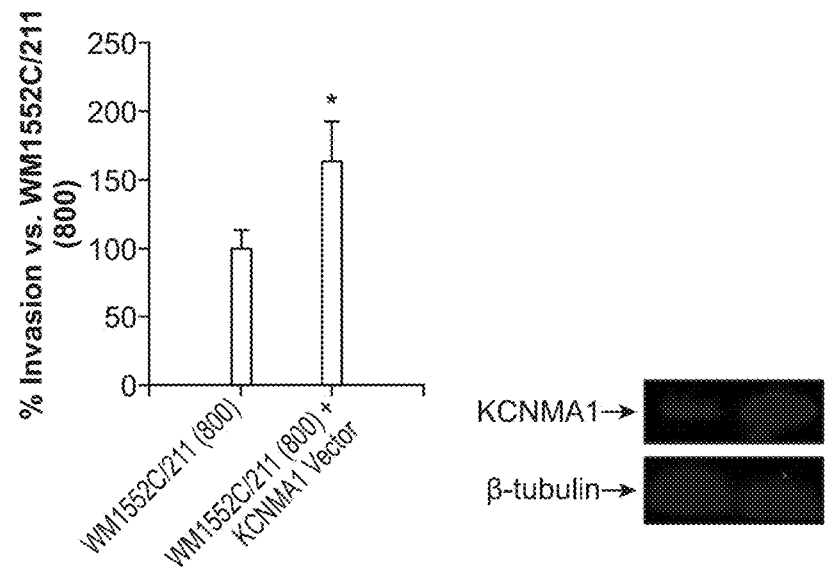

To fully demonstrate that KCNMA1 is a key contributor to miR-211 effects, we examined whether concomitant overexpression of KCNMA1 might also rescue the miR-211 anti-invasive effects. A KCNMA1 constitutively-expressing plasmid was transiently transfected into WM1552C/211 (800) cells. This plasmid (Origene clone NM_002247.2) contains a KCNMA1 ORF without its native 3'UTR (making it resistant to regulation by miR-211). KCNMA1 protein expression levels were then detected by KCNMA1 antibody. Western blot results revealed that KCNMA1 protein levels were elevated in transfected cells ["WM1552C/211(800)+ KCNMA1 vector" relative to control cells] (FIG. 8E, bottom). Results from an invasion assay (FIG. 8E, top) illustrate that the same batch of melanoma cells that exhibit high KCNMA1 protein expression [WM1552C/211(800)+KCNMA1 vector" cells] also show high cell invasiveness, higher by at least 60% compared to the control cell cultures.

Example 8: Mutation in TRPM1 Promoter Down-Regulates Expression of miR-211

Sequencing of Upstream TRPM1 Promoter

In order to determine whether the differences in miR-211 expression between melanocytes and invasive melanoma result from differences in the expression of the TRPM1 gene, the TRPM1 gene promoter analyzed. Sequencing alignment and comparison was performed for the upstream TRPM1 promoter region of melanocytes and three cell lines: SKMEL-28, A375, and WM1552C. The promoter sequences from each cell type are shown in FIG. 13. The alignment revealed that the upstream TRPM1 promoter region of TRPM1 is identical between melanocytes and SKMEL-28 cells. However, point mutations were detected in both the A375 and WM1552C cell lines, three of which are identical between the two cell lines. The data demonstrates that SKMEL-28 cells express miR-211 because the TRPM1 gene is under the control of a wild-type in promoter; whereas both A375 and WM1552C cells, which do not express miR-211, have multiple point mutations in their TRPM1 promoters.

Luciferase Reporter Expression Assay

Figure 14:
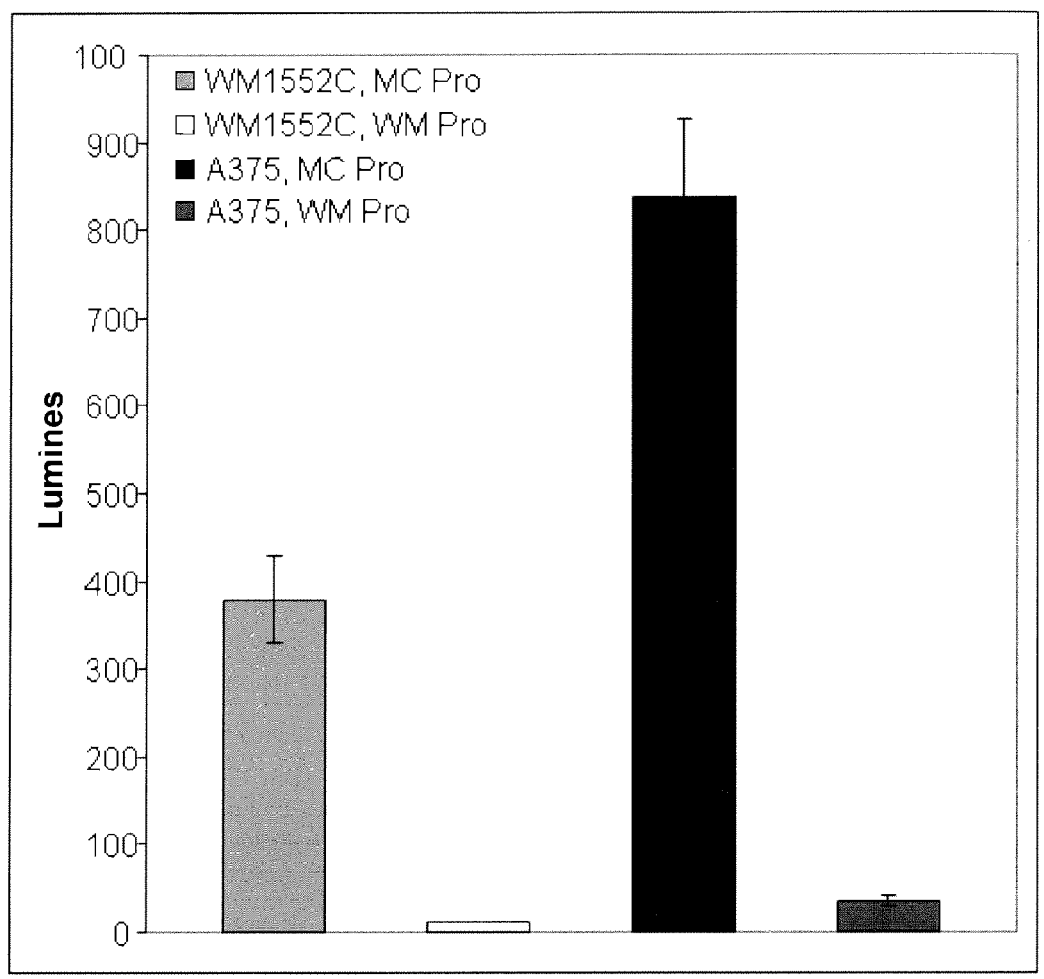
FIG. 14 is a bar graph showing the results of a luciferase reporter assay comparing two melanoma cell lines with both melanocyte and WM1552C TRPM1 reporters.

In order to investigate whether the mutations in the TRPM1 gene promoter of A375 and WM1552C cells affects (downregulates) the expression of the TRPM1 gene and miR-211, the luciferase reporter gene placed under operational control of either the melanocyte TRPM1 promoter (wildtype; "MC Pro") or the WM1552C TRPM1 promoter (mutated promoter; "WM Pro"). Each of these constructs was transfected into WM1552C and A375 cells and luciferase luminescence was measured. In both cell lines, the melanocyte TRPM1 promoter is significantly more functional than the WM1552C TRPM1 promoter (FIG. 14). The results demonstrate that the point mutations present in the WM1552C TRPM1 promoter reduce the expression of TRPM1 and miR-211 regardless of cell type background.

Example 9: Effects of Treatment of SKMEL-28 Cells with MITF siRNAs

Down-Regulation of MITF

Figure 15A:
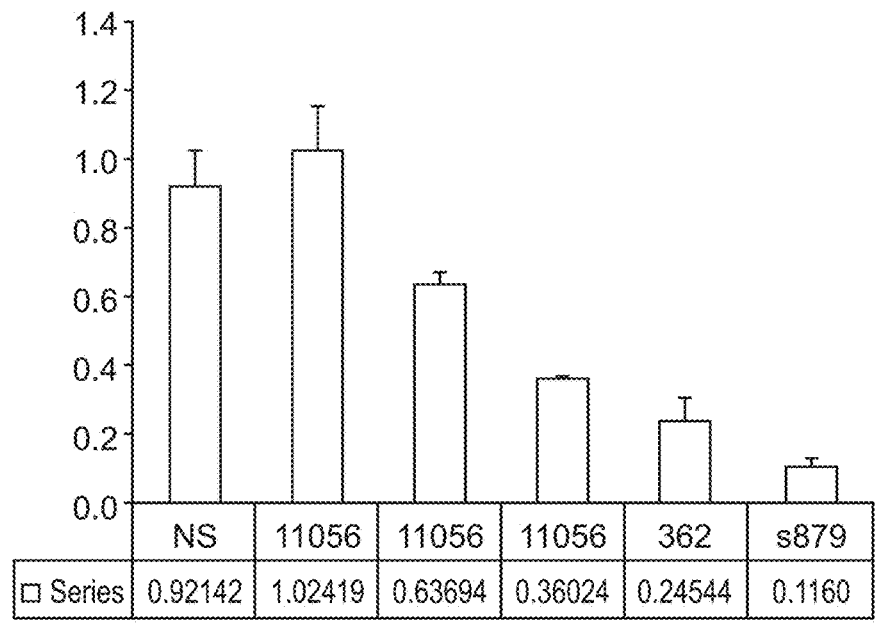
FIG. 15 is a series of bar graphs showing the results of a qPCR assay to determine expression of MITF (A), TRPM1 (B), IGFBP5 (C), and RUNX2 (D) after treatment with MITF siRNAs.

The effect of MITF down regulation on TRPM1 gene expression and downstream targets of miR-211 was assessed. SKMEL-28 cells were treated with either a nonsense miRNA or one of five different siRNAs specific to MITF: 110566, 110564, 110565, 3629, and s8791. Each of the five MITF siRNAs is a product ID of a Silencer® Select siRNA (Ambion, Applied Biosystems) for a validated siRNA. The sequences are proprietary, but map approximately to the 10th, 10th, 9th, 3rd, and 6th exons, respectively. The nonspecific (NS) control siRNA is a mix of 48 different non-specific siRNAs (Ambion) pooled together. Expression of MITF was determined for each group using qPCR detection methodology. The results, which are shown in FIG. 15A, demonstrate that four of the siRNAs (110564, 110565, 3629, and s8791) significantly down-regulated MITF (35%, 64%, 75%, and 90%, respectively).

Down-Regulation of TRPM1

Figure 15B:
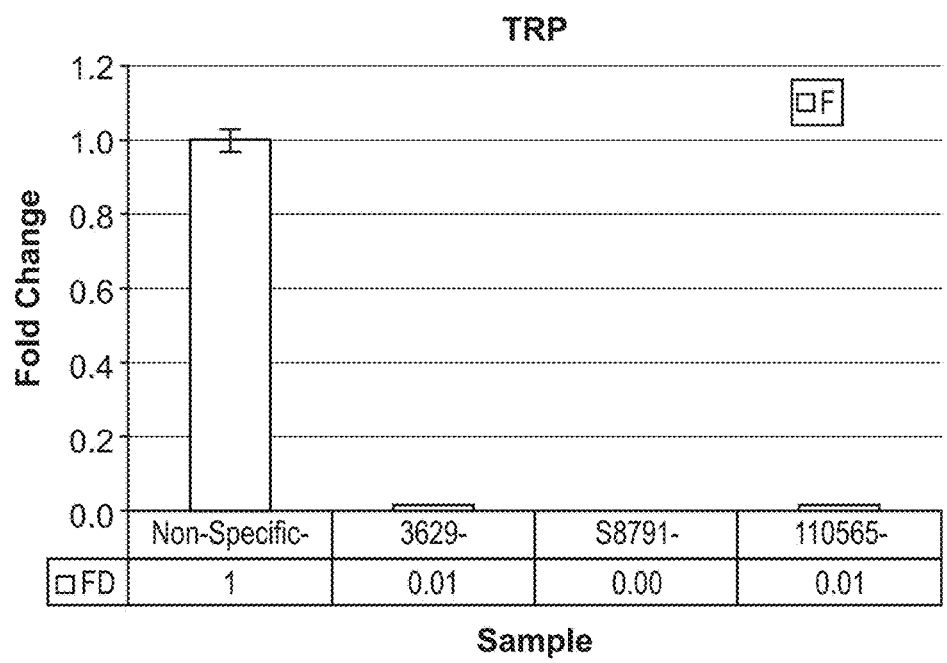

Expression of TRPM1 was determined via qPCR for SKMEL-28 cells treated with the three top-performing siRNAs as determined by the MITF down-regulation study described above. The results shown in FIG. 15B demonstrate that the three siRNAs tested (110565, 3629, and s8791) significantly down-regulated TRPM1. This confirms that MITF acts as a transcription factor to positively-up-regulate TRPM1, since a knock-down of MITF by the three siRNAs resulted in significant down-regulation of TRPM1, and, in the case of s8791, a complete silencing of TRPM1. As discussed above, it is expected that down-regulation of TRPM1 results in a down-regulation of miR-211 expression.

Up-Regulation of IGFBP5

Figure 15C:
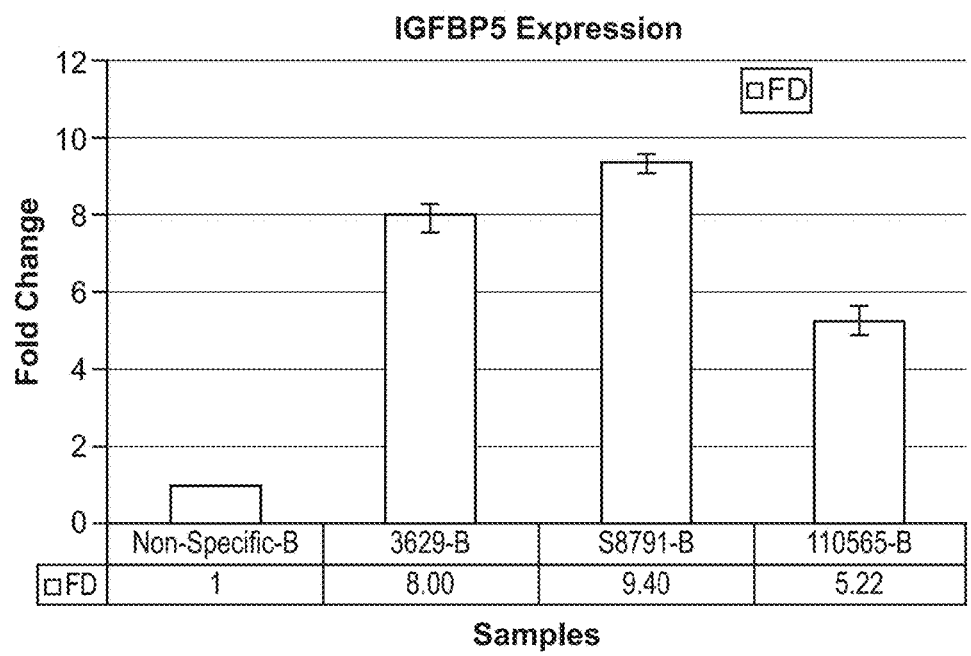

Expression of IGFBP5, a target of miR-211, was assessed using qPCR for SKMEL-28 cells treated with the three best-performing siRNAs as determined by the MITF down-regulation study. With the lack of TRPM1 expression due to MITF knock-down, IGFBP5 is up-regulated 8-fold for siRNA 3629, 9.4-fold for s8791, and 5.22-fold for 110565 (FIG. 15C).

Down-Regulation of RUNX2

Figure 15D:
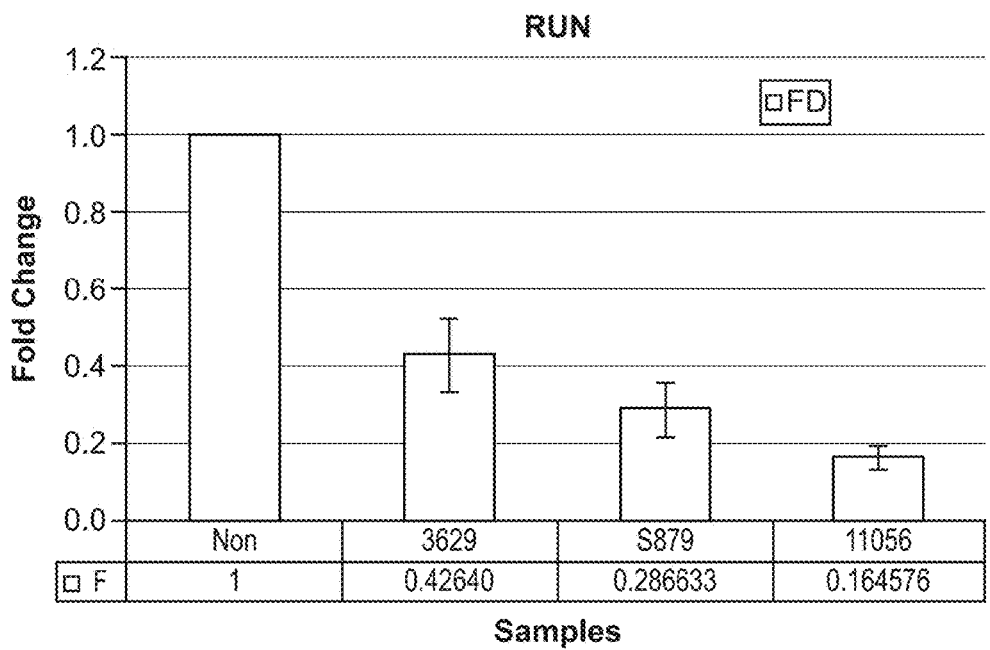

RUNX2 is a putative target of miR-211 and therefore would be expected to be up-regulated following MITF knock-down. However, as shown in FIG. 15D, RUNX2 is consistently down-regulated in response to MITF knock-down. This finding suggests that RUNX2 is positively dependant upon MITF expression and therefore is unlikely to be a miR-211 target.

Example 10: IGFBP5 mRNA is Down-Regulated by miR-211 Expression

Figure 16:
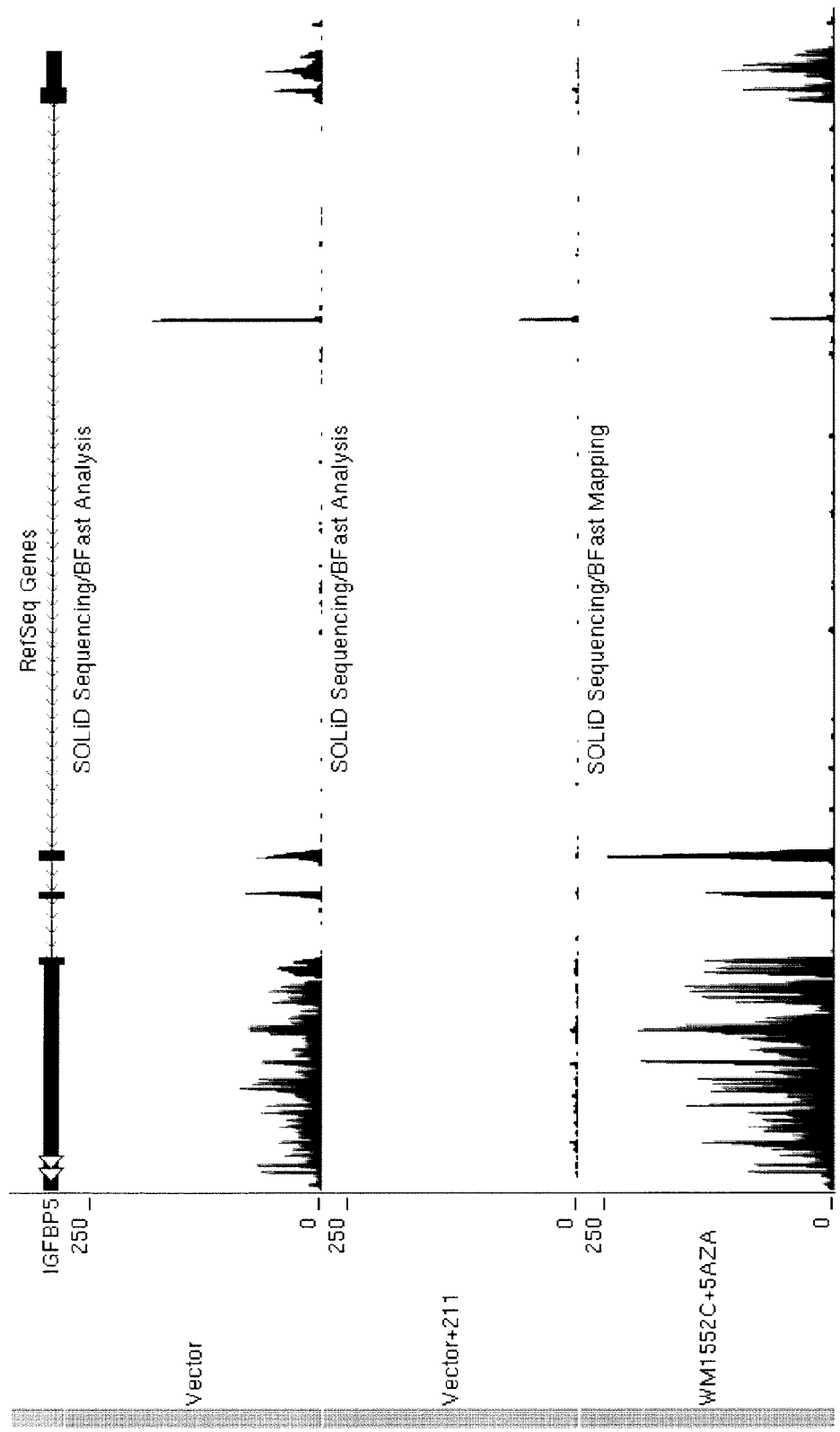
FIG. 16 is a chart showing Next Gen sequencing results of the IGFBP5 locus in WM1552C and WM1552C/211 cells.

To extend the findings of the MITF knock-down study and to further establish IGFBP5 as a miR-211 target, the effect of miR-211 expression on IGFBP5 mRNA was determined. WM1552C cells were transfected with either an empty vector or the vector encoding and expressing miR-211. Additionally, untransfected WM1552C cells were treated with 5-Aza-2'deoxycytidine ("5-Aza") to investigate whether miR-211 down-regulates IGFBP5 mRNA production through a genomic methylation mechanism. The sequencing results shown in FIG. 16 demonstrate that IGFBP5 mRNA is expressed in the IGPBP5 locus in WM1552C cells. However, over-expression of miR-211 reduces IGFBP5 mRNA expression to almost to undetectably levels, thereby validating IGFBP5 as a target of miR-211. 5-Aza treatment had no effect on the expression of IGFBP5 mRNA, suggesting that DNA methylation is not a means by which IGFPB5 is down-regulated by miR-211.

Figure 17:
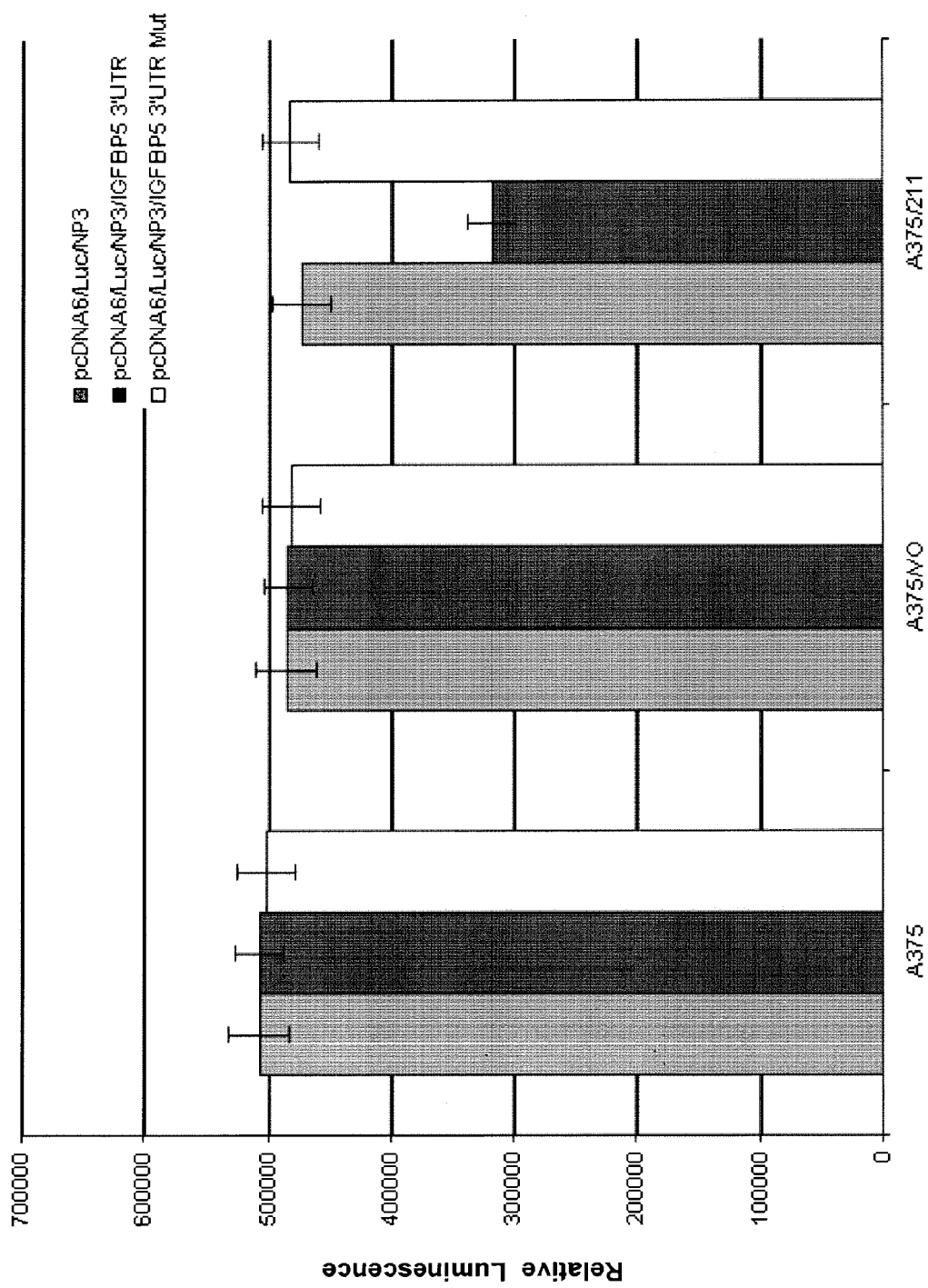
FIG. 17 is a bar graph showing the results of a luciferase reporter assay conducted to determine the relative luminescence of a melanoma cell line, vector only, or miR-211 expressing cells transfected with either native or mutant 3'UTR reporter constructs.

Example 11: Target Inhibition Assay of IGFBP5 3'UTR by miR-211 Using Luciferase Reporter Assay A putative miR-211 binding site with the sequence 5'-aaagggaa-3' (SEQ ID NO:40) is present in the 3'-UTR of the IGFBP5 mRNA (SEQ ID NO:41; FIG. 26). In order to investigate the specificity and mechanism of miR-211 inhibition of IGFBP5, three luciferase reporter constructs were created, each having a different 3'-UTR on the luciferase gene. The constructs were as follows: (i) luciferase coding sequence with the luciferase 3'-UTR ("pcDNA6/Luc/NP3"), (ii) luciferase coding sequence with the IGFBP5 3'-UTR ("pcDNA6/Luc/NP3/IGFBP5 3'UTR"), and (iii) luciferase coding sequence with the IGFBP5 3'-UTR having a mutation in the miR-211 binding site ("pcDNA6/Luc/NP3/IGFBP5 3'UTR Mut"). The mutant miR-211 binding site is represented by SEQ ID NO:42 (5'-taagccta-3'). Vectors encoding these constructs were transfected into native A375 cells, A375 cells containing the miR-211-expressing vector ("A375/211"), or A375 cells having an empty vector ("A375/VO"). As shown in FIG. 17, expression of luciferase is strong in native A375 cells regardless of the 3'UTR present in the reporter plasmid (either native luciferase, wildtype IGFBP5 3'UTR, or mutated IGFBP5 3'UTR). Expression of luciferase was also indistinguishable in the A375/VO (vector only) cells which do not express significant levels of miR-211. In the miR-211-expressing A375 cells, luciferase expression was unaffected for the constructs containing the native luciferase 3'UTR and the IGFBP5 3'UTR in which the miR-211 binding site had been altered. However, the luciferase activity was reduced by nearly 40% when the native IGFBP5 3'UTR was expressed. These results confirm that IGFBP5 is a target of miR-211 and that miR-211 reduces IGFBP5 expression by its action at the 3'UTR.

Example 12: Effects of TP53 siRNAs on MITF, TRPM1, and IGFBP5

Figure 18A:
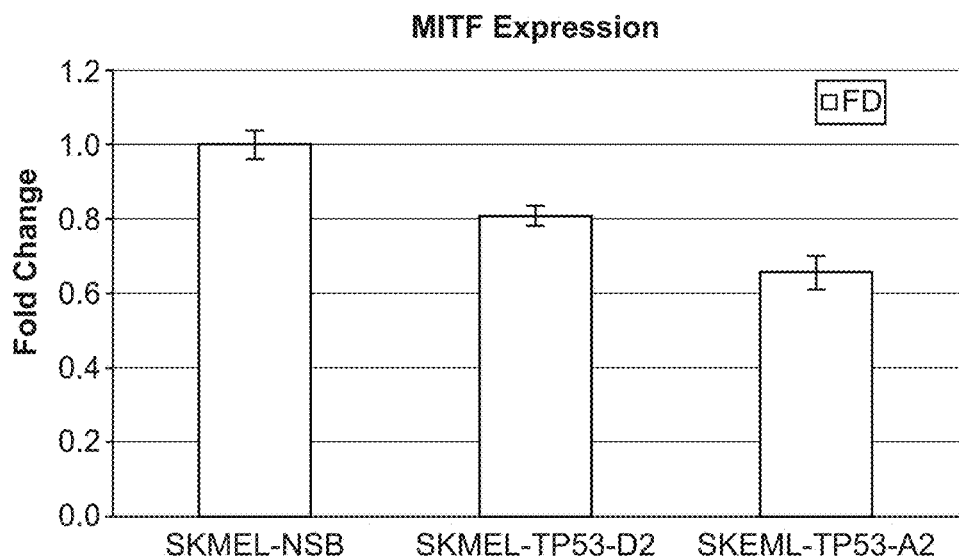
FIG. 18 is a series of bar graphs showing the expression of MITF (A), TRPM1 (B), and IGFBP5 (C) after treatment with TP53 siRNAs.
Figure 18B:
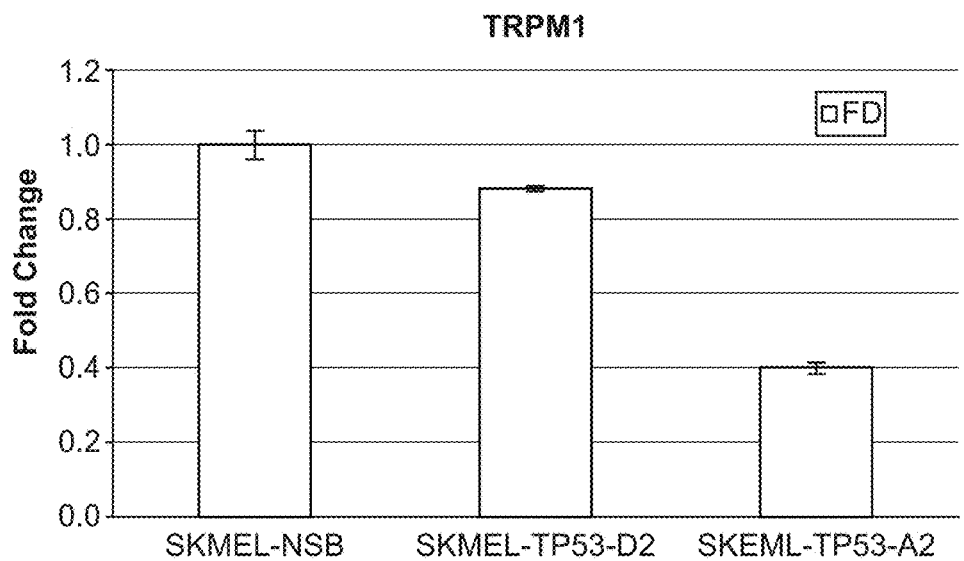
Figure 18C:
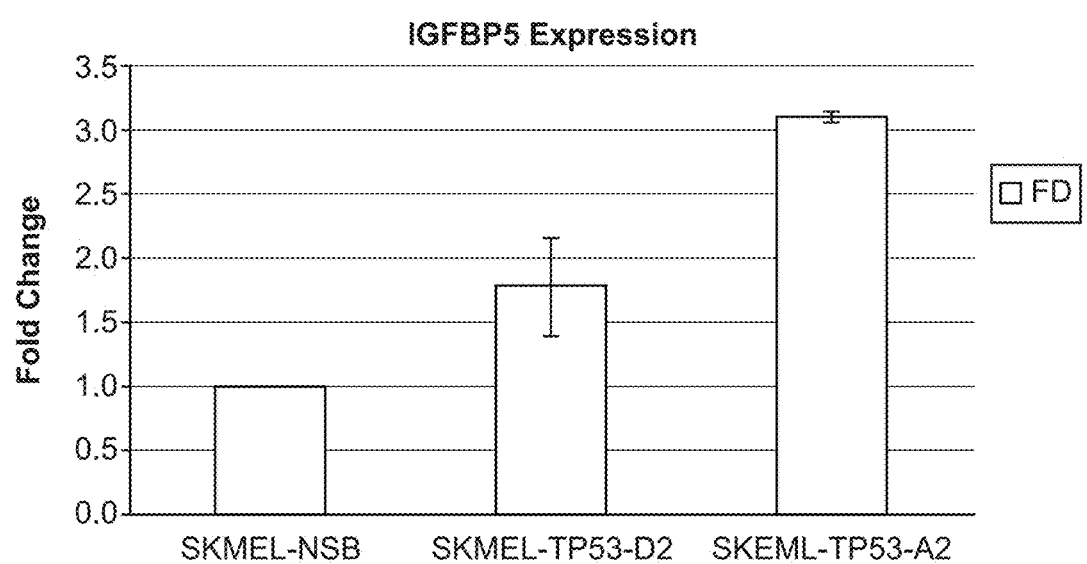

The role of TP53 (a putative upstream effector of MITF) was investigated. Four different TP53 siRNAs were transfected into SKMEL-28 cells for 48 hours. RNA was purified, and qRT-PCR was performed, normalized to GAPDH. Two siRNAs (TP53-A2 and TP53-D2, proprietary Silencer® siRNAs with Ambion/Applied Biosystems product IDs 106141 and 2533, respectively, and which map approximately to the 11th and 6th exons, respectively, of TP53) induced a down-regulation of TP53 by greater than 90%. These siRNAs were then tested for downstream effects on MITF, TRPM1, and IGFBP5 expression. RNA samples were acquired, and qPCR was performed using Taqman probes. FIG. 18A-C, demonstrate that TP53 knockdown resulted in significant reductions in the expression of MITF, TRPM1 mRNA. Consistent with the MITF/TRPM1/IGFBP5 pathway established in the previous experiments, IGFBP5 expression was markedly increased. The TP53-A2 siRNA was consistently more effective than the TP53-D2 siRNA.

Example 13: Effects of Hypoxic Conditions (Simulated and Actual) on Cell Lines with and without miR-211 Expression A375 and WM1552C Cells A375 cells and WM1552C, both wild-type and miR-211-expressing, were subjected to treatment with 0, 250 nM, or 400 nM defroxamine (DFO) to simulate hypoxic conditions in order to determine whether miR-211 expression is capable of being regulated by changes in $O_2$ concentrations. Cell counts were performed for each treatment group.

Figure 19:
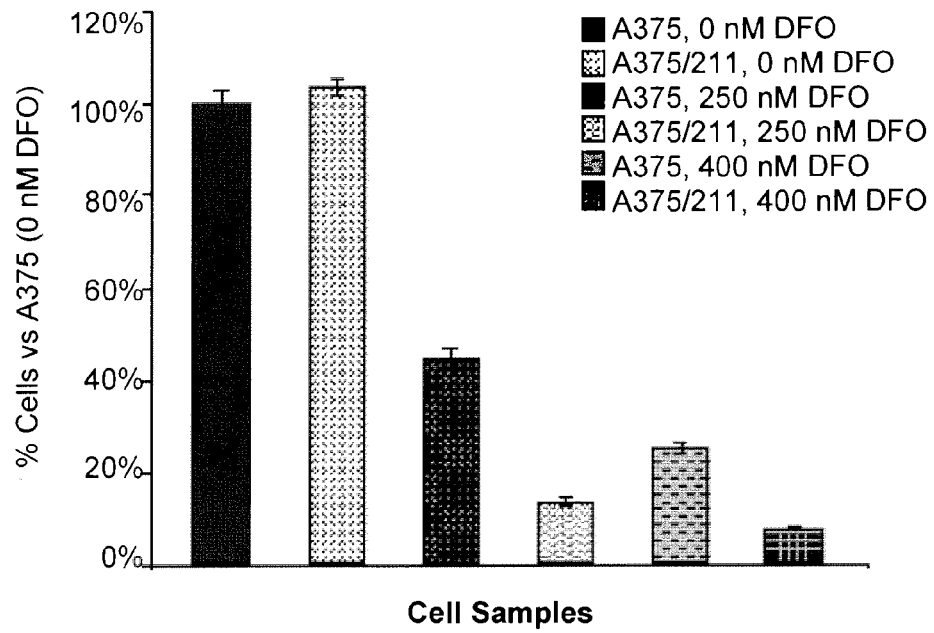
FIG. 19 is a bar graph showing the results of a cell count of A375 and A375/211 cells after treatment with 0 nM DFO, 250 nM DFO, or 400 nM DFO.
Figure 21:
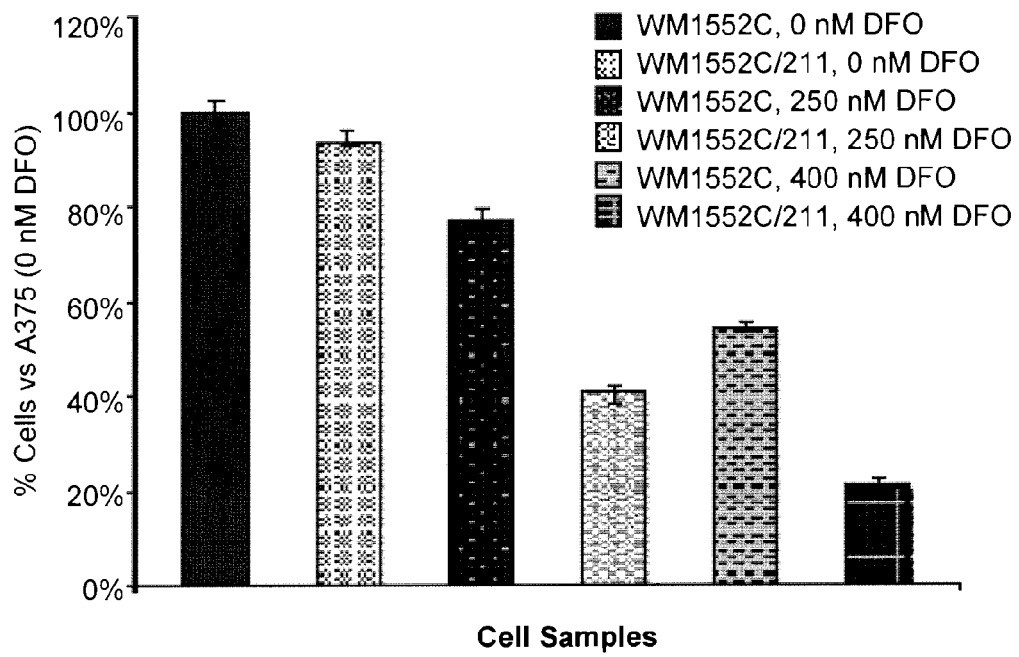
FIG. 21 is a bar graph showing the results of a cell count of WM1552C and WM1552C/211 cells after treatment with 0 nM DFO, 250 nM DFO, or 400 nM DFO.

FIG. 19 shows the cell counts following DFO treatment in A375 cells. Relative to untreated cells, survival was about 45% following 250 nM DFO and about 25% following 400 nM DFO. The presence of miR-211 in these cells caused this effect to be greatly exacerbated, reducing survival to about 13% at 250 nM DFO and about 8% at 400 nM DFO. Similarly, for WM1552C cells, survival was about 77% at 250 nM DFO and about 55% at 400 nM DFO, compared to untreated cells (FIG. 21). The presence of miR-211 in WM1552C cells also resulted in increased cell loss with survival being about 40% at 250 nM DFO and about 21% at 400 nM DFO.

Figure 20:
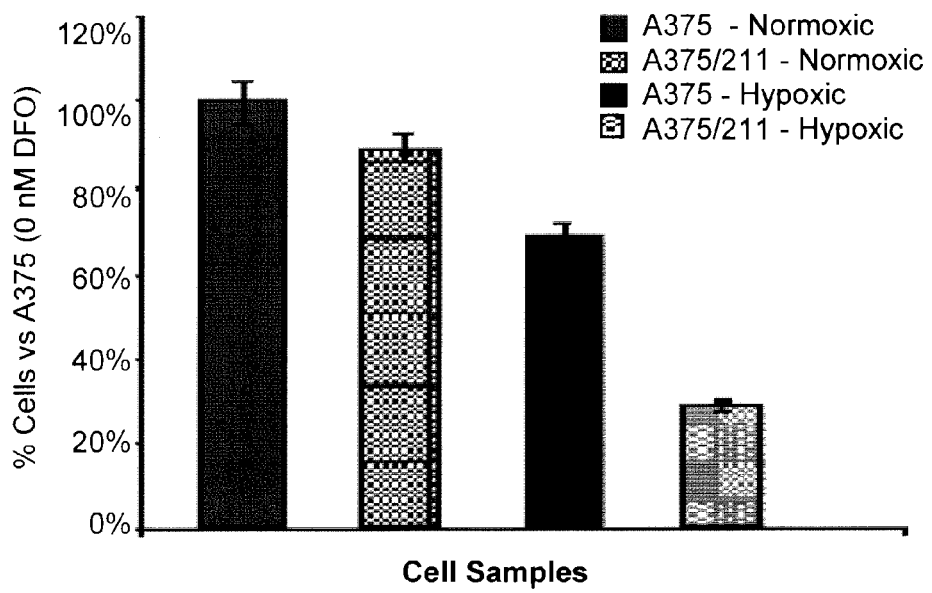
FIG. 20 is a bar graph showing the results of a cell count of A375 and A375/211 cells in hypoxic and normoxic conditions.
Figure 22:
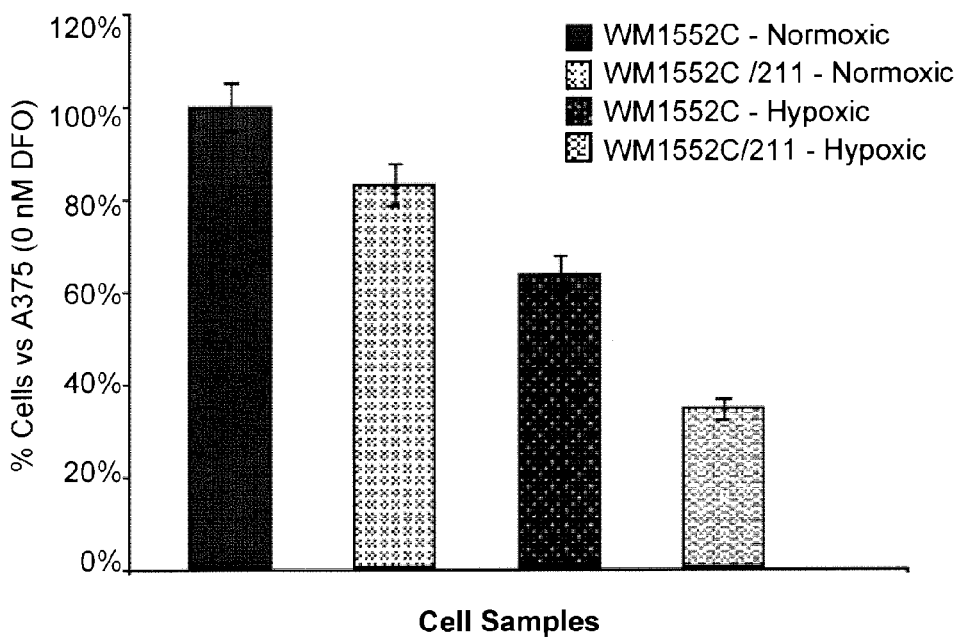
FIG. 22 is a bar graph showing the results of a cell count of WM1552C and WM1552C/211 cells in hypoxic and normoxic conditions.
Figure 23:
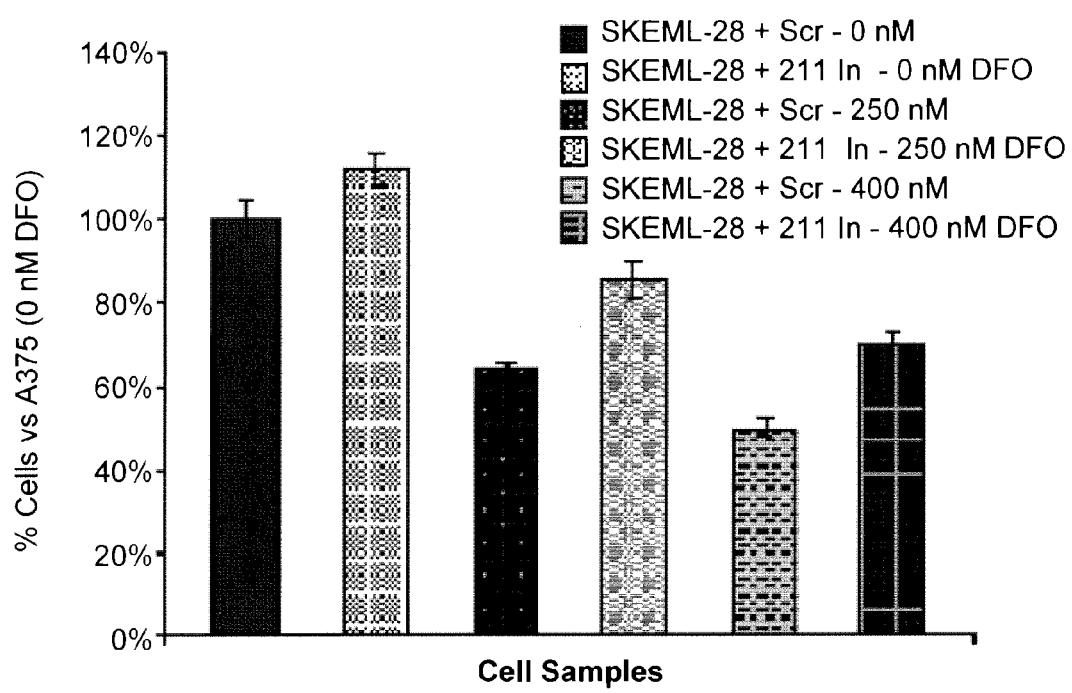
FIG. 23 is a bar graph showing the results of a cell count of SKEML-28 and SKEML-28/211 cells after treatment with 0 nM DFO, 250 nM DFO, or 400 nM DFO.

To test under actual hypoxic conditions, both cell lines were placed into a hypoxic chamber containing 2% $O_2$ prior to determination of cell counts. When compared to normoxic conditions for both A375 and A375/211 groups, the cell counts demonstrate that survival of A375 cells was about 68% of normoxic condition cells (FIG. 20). As in the DFO-simulated hypoxic condition assay, the presence of miR-211 caused the effect to be greatly exacerbated, reducing survival to about 29%. Likewise, hypoxic conditions for WM1552C cells resulted in about 64% survival which was reduced to 34% survival in cells expressing miR-211 (FIG. 22).

SKMEL-28 Cells

SKMEL-28 cells, were subjected to the same DFO or hypoxic conditions as described above either in the presence or absence of an miR-211 inhibitor (has-miR-211 Anti-miR™ miRNA Inhibitor, Ambion, catalog numberAM17000, ID AM10168). DFO treatment resulted in a loss of SKMEL-28 cells, but not to the same extent as observed for the A375 and WM1552C cell lines. The survival of SKMEL-28 cells was about 64% at 250 nM DFO and about 50% 400 nM DFO, compared to untreated cells. Simultaneous treatment with the miR-211 inhibitor caused this deleterious effect to be somewhat rescued. The survival of the SKMEL-28 cells treated with the miR-211 inhibitor was about 85% at 250 nM DFO and about 70% at 400 nM DFO. Since SKMEL-28 cells express miR-211 highly, this indicates that the presence of miR-211 in wild-type cells is actually a hindrance to cell growth under hypoxic conditions.

Figure 24:
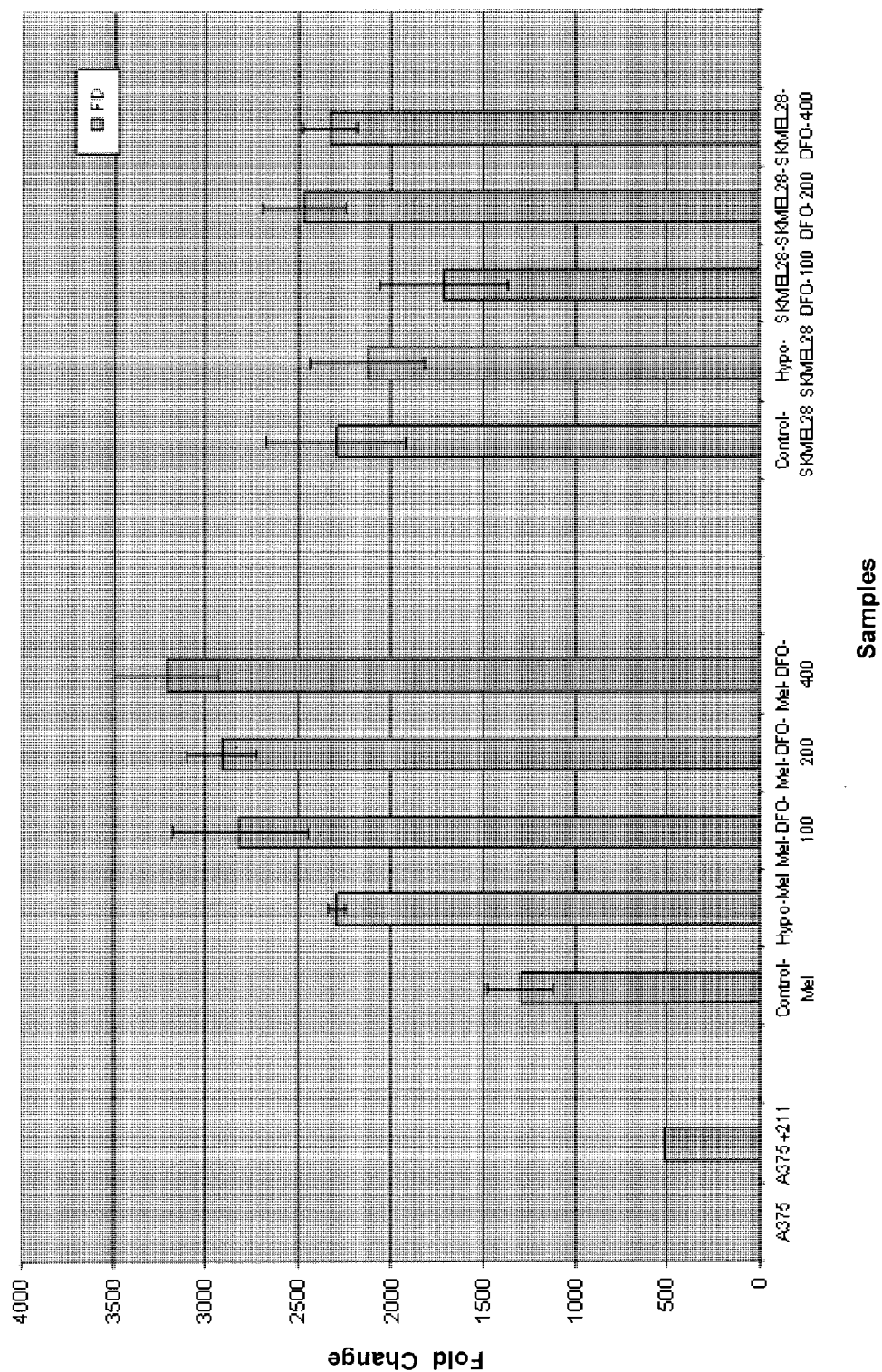
FIG. 24 is a bar graph showing the results of a qRT-PCR assay of melanocytes and SKMEL-28 cells under hypoxic or simulated hypoxic conditions.

The effect of hypoxia on miR-211 expression was investigated under simulated (DFO) and actual hypoxic conditions in both melanocytes and SKMEL-28 cells. miRNA-211 expression was determined by qPCR. The results in FIG. 24 demonstrate that the expression of miR-211 is high in melanocytes and virtually undetectable in A375 cells. Melanocyte miR-211 expression is also significantly greater that miR-211 expression in the A375/211 cells. When hypoxia is induced in melanocytes, either by actual hypoxia (2% $O_2$) or using DFO, miR-211 expression is markedly increased. For DFO, miR-211 expression increases in a dose-dependent manner. However, neither simulated nor actual hypoxic conditions had a significant effect on miR-211 expression in SKMEL-28 cells, suggesting that miR-211 expression is not capable of being regulated by changes in $O_2$ concentrations in these melanoma cells.

Figure 25:
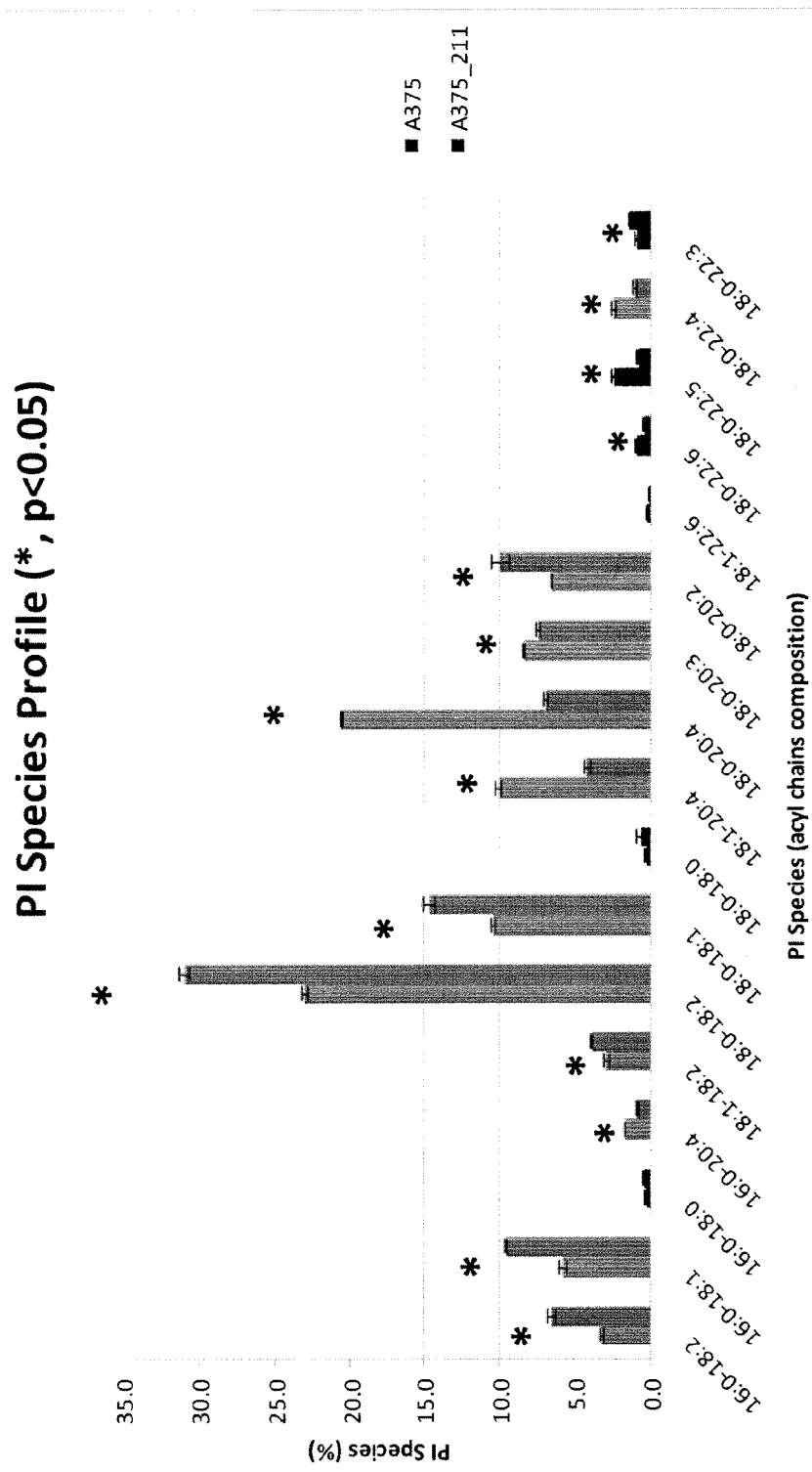
FIG. 25 is a bar graph comparing the PI species (acyl chains composition) of A375 cells to A375/211 cells.

Example 14: Effect of miR-211 Expression in A375 Cells on the Production of Lipid Species To determine the effect of miR-211 expression in A375 cells on the production of lipid species, as an indicator of metabolic change, fatty acids were isolated and quantitated in A375 cells and A375/211 by mass spectrometry. The results, which are shown in a bar graph in FIG. 25, demonstrate that the presence of miR-211 is capable of altering the profile of lipid species produced in these melanoma cells. The most notable is the large increase in 18:0-18:2 acyl chains and the large decrease in content of 18:0-20:4 acyl chains in the A375/211 cells. This confirms that miR-211 is capable of altering the metabolic profile of these metabolic cells.

Example 15: Expression of PGC1α in A375 Cells Vemurafenib-Resistant Cells

Figure 27:
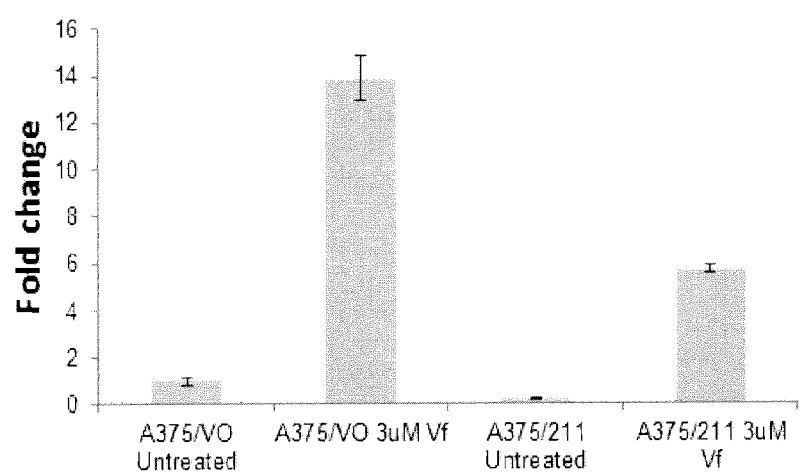
FIG. 27 is a bar graph showing expression of PGC1α in melanoma cells treated with the BRAF inhibitor vemurafenib.

To demonstrate that PGC1α and its targets and regulators may be used as pharmacodynamic markers of acquired vemurafenib resistance, the variance in PGC1α expression in A375 cells was first determined between cells treated with vemurafenib and untreated cells. A375 vector only cells, as well as A375/211 cells, were treated with 3 uM vemurafenib for 47 hours at 37° C. (untreated samples were also tested as controls). PGC1α levels of each sample were determined by qRT-PCR using the methods described above in Example 1. The results, which are shown in a bar graph in FIG. 27, demonstrate that PGC1α is upregulated by vemurafenib in parental melanoma cells, but the increase is attenuated in cells expressing miR-211.

Figure 28:
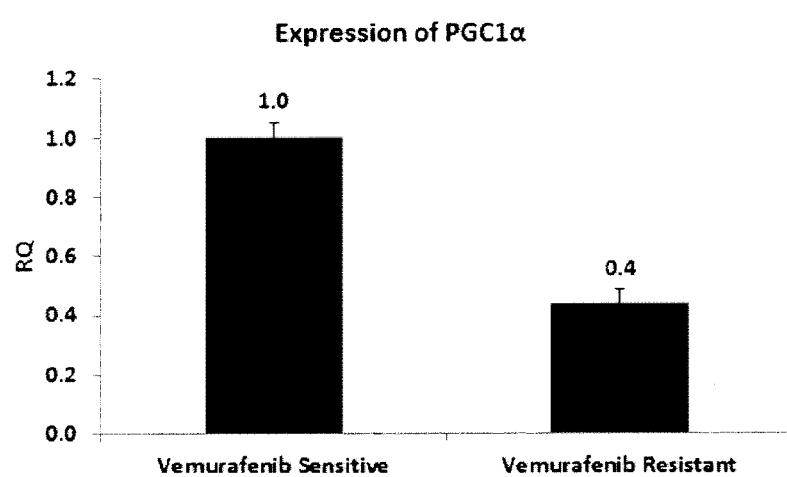
FIG. 28 is a bar graph showing expression of PGC1α in vemurafenib-resistant and vemurafenib-sensitive melanoma cells.
Figure 29:
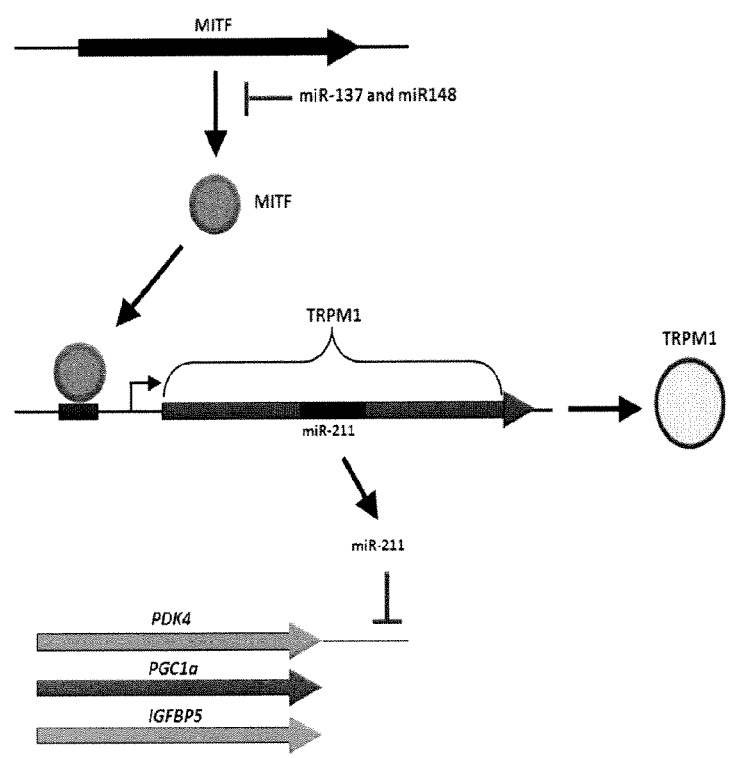
FIG. 29 is a schematic drawing showing the regulatory pathway of miR-211 and its related genes.

Next, to demonstrate the expression differential of PGC1α between vemurafenib-resistant and vemurafenib-sensitive A375/211 cells. PGC1α levels of both the vemurafenib-sensitive and vemurafenib-resistant samples were determined by qRT-PCR using the methods described above in Example 1. The results, which are shown in a bar graph in FIG. 28, demonstrate that vemurafenib-resistant cells show reduced expression of PGC1α (<60%) as compared with vemurafenib-sensitive cells. Therefore, PGC1α and genes involved in its regulatory pathway may be used as pharmacodynamic markers of acquired vemurafenib resistance.

Example 16: miR-211 Functional Network of Target Genes Altering Melanoma Metabolism and Melanocyte Transformation In order to determine how a reduction in miR-211 expression affects the cellular metabolome of melanoma cells, large scale, unbiased metabolite profiling was applied to identify individual metabolites and metabolic pathways in melanoma cells A375 (stage IV) and WM1552C (stage III) expressing miR-211 or empty vector parental cells. Using state-of-the-art LC/MS instrumentation (available at Sanford-Burnham La Jolla and Lake Nona), thousands of unique small molecule metabolites were profiled in the two cell types. Importantly, both known (metabolites identified from library matches) and unknown (unidentified) metabolites were profiled, allowing identification of novel metabolites as well as known metabolic pathways linked to miR-211. The metabolite profiles were analyzed using XCMS and significantly increased or decreased metabolites were identified. These were generally considered to be metabolites that showed at least a three-fold change in abundance with a p-value<0.01, although these parameters may be customized for each system for measuring metabolites. Known metabolites (from the tricarboxylic acid [TCA] cycle, pentose phosphate pathway, and glycolysis) were further analyzed using bioinformatic tools to identify metabolic pathways that are enriched for the altered metabolites.

Figure 30:
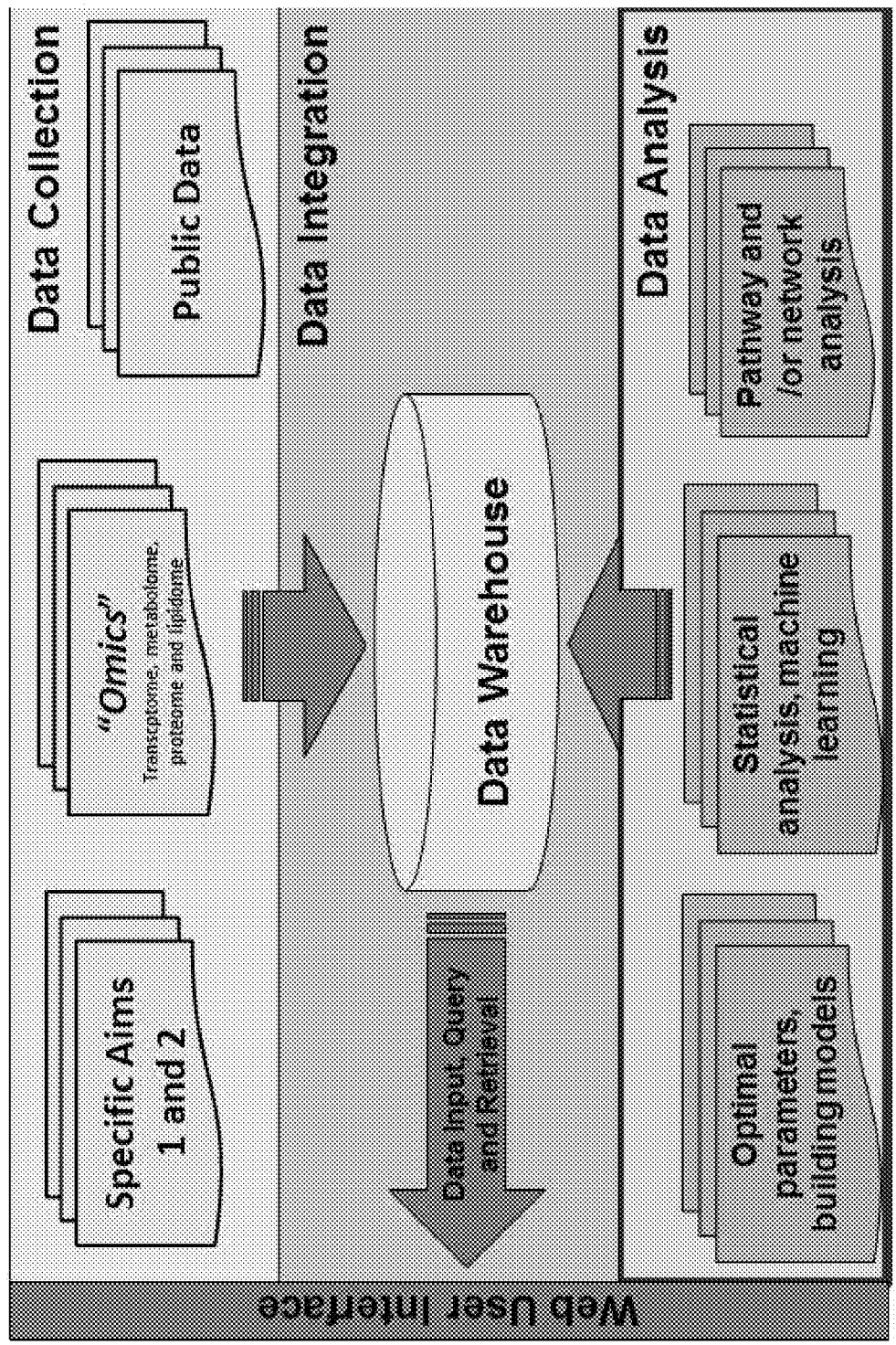
FIG. 30 is a flow chart showing a summary of the contemplated data integration system in which multidimensional "omics" data will be analyzed and integrated by using advanced computational algorithms.

Using the techniques shown in the schematic in FIG. 30, functional networks will be built from data obtained from global metabolomics, lipidomics, transcriptomics, and proteomics, in order to identify the changes in global coding and noncoding genes in miR-211-expressing and parental cells, and to build systems level molecular "interactome" models to identify the molecular mechanisms that underpin melanoma metabolism and development. The preliminary high-throughput data has been generated, and the data integration process is underway. Traditional approaches for biological research often involve studying a single level of cellular components, while in reality, most genes, proteins and other components carry out their functions within an intricate network represented by complex interconnections and interdependencies. Multiple integrative methods will be used to help researchers to obtain comprehensive interpretations of high-throughput datasets involving genomics, metabolomics, and lipidomics output.

To develop functional pathways and networks, the network-based analysis will be applied to the transcriptomics, metabolomics, and lipidomics data to identify regulated pathways and networks affected by miR-211 expression. The rationale for developing an integrated pathway is to identify genes, proteins, metabolites, and lipids that are connected to the expression of miR-211 in human melanomas. In addition to the Ingenuity IPA and Gene Set Enrichment Analysis (GSEA) approach for standard functional enrichment analysis, the Bayesian network approach will be applied to reconstruct gene-regulatory pathways/networks. A series of unsupervised methods (such as hierarchical clustering, principal component analysis (PCA), and self-organizing maps (SOM)) and supervised methods (such as discriminant function analysis (DFA) and partial least squares (PLS)) will be applied as multivariate analyses for metabolomics data. Furthermore, metabolite set enrichment analysis (MSEA) and metabolite pathway enrichment analysis (MPEA) will be used to identify and interpret patterns of metabolite concentration changes in a biologically meaningful context. Since metabolomics and lipidomics data have unique analysis requirements compared with transcriptomics data, they will require extensive data pre-processing and advanced analysis. At Sanford-Burnham, we have unique capabilities for such analyses, and Dr. Qi has published extensively in this area. Finally, publicly available metabolomics databases such as Metlin, CheBI, and HMDB will also be used. To evaluate associations between pathways/networks and changes observed in cell biology assays, the significant over-represented pathways/networks (p-value<0.05) for each experiment will be selected and tested by a Global Test program. This program tests groups of covariates (genes) for association with a response variable of interest. Significant correlated pathways/networks with p-value<0.05 will be identified for further enrichment.

Figure 31:
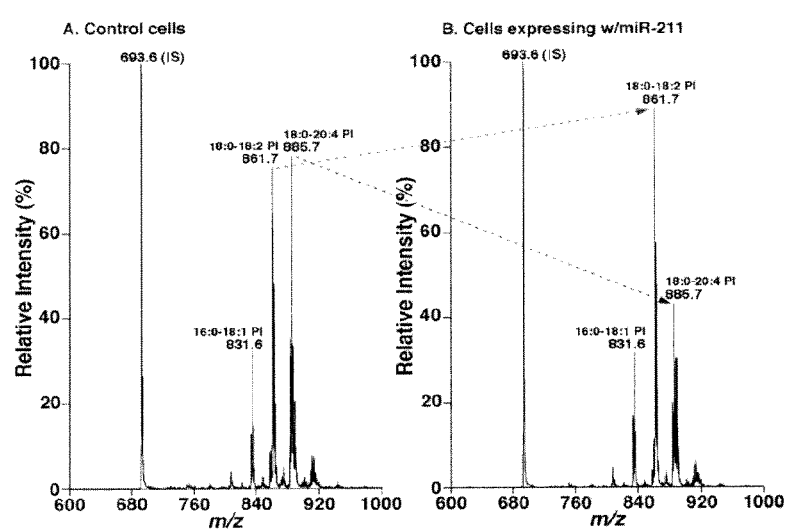
FIG. 31 is a mass spectrometric analysis of miR-211-expressing A375 cells. Representative mass spectrometric traces of phosphatidylinositol (PI) species present in human melanoma cells A375 transfected with empty vector (Panel A-control cells) or with miR-211 (Panel B). The mass spectra were displayed after normalization to the internal standard (IS) peak at m/z 693.6.

Changes in lipid metabolism can affect numerous cellular processes, including cell growth, proliferation, differentiation, and motility. To analyze cellular lipid species, lipidomes from melanoma cells expressing miR-211 or empty vector were determined by using multidimensional mass spectrometry-based shotgun lipidomics. Lipid classes and individual lipid molecular species induced after expression of miR-211 were identified, and in a preliminary study, substantial changes in phosphatidylinositol (PI) species levels were shown (FIG. 31).

Figure 32:
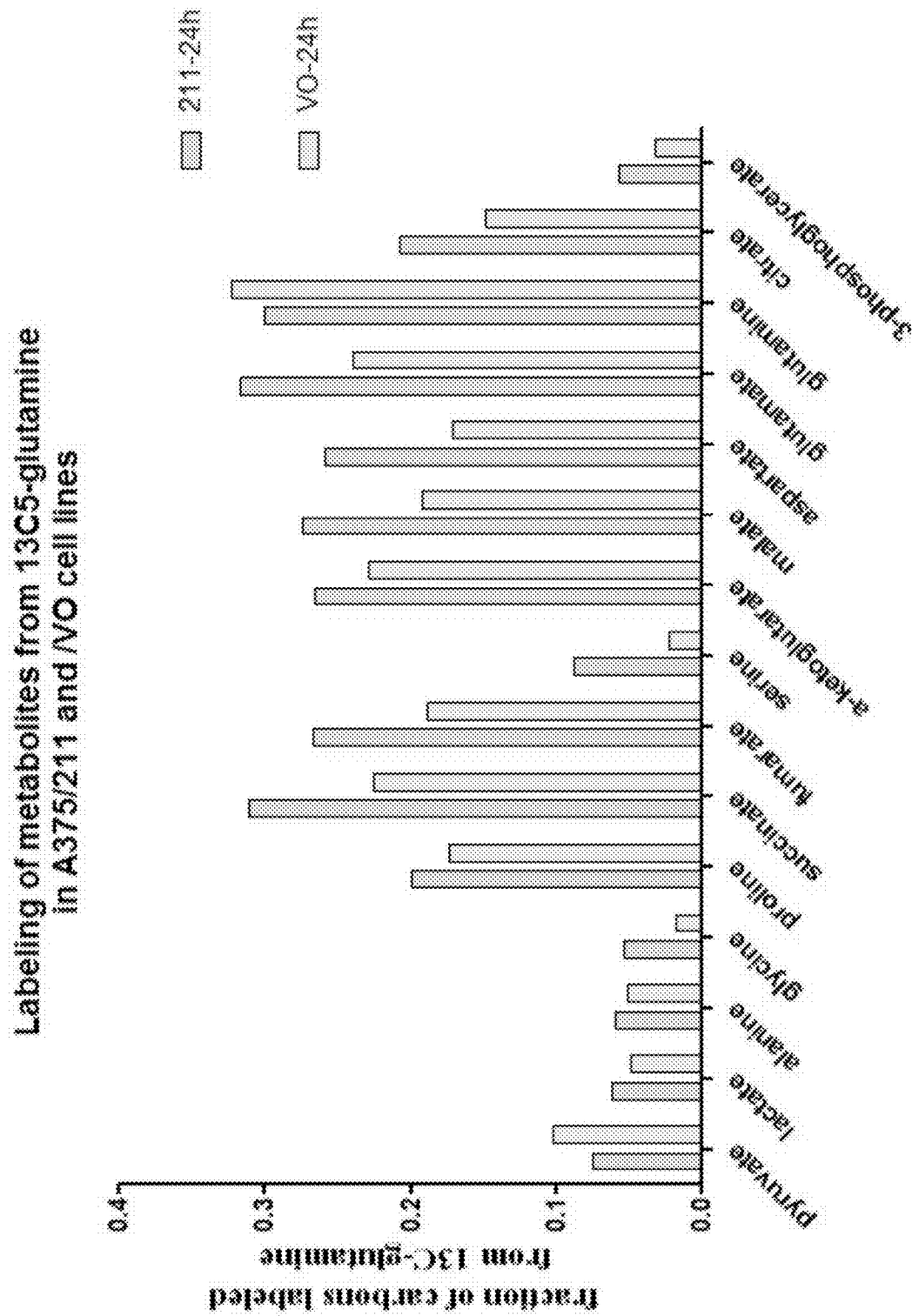
FIG. 32 is a bar graph showing that miR-211 expression accelerates glutamine metabolism in A375 melanoma cells. Control or miR-211-transfected cells were labeled with 13C-glutamine, and 13C-labeled metabolites were measured via mass spectrometry.
Figure 33:
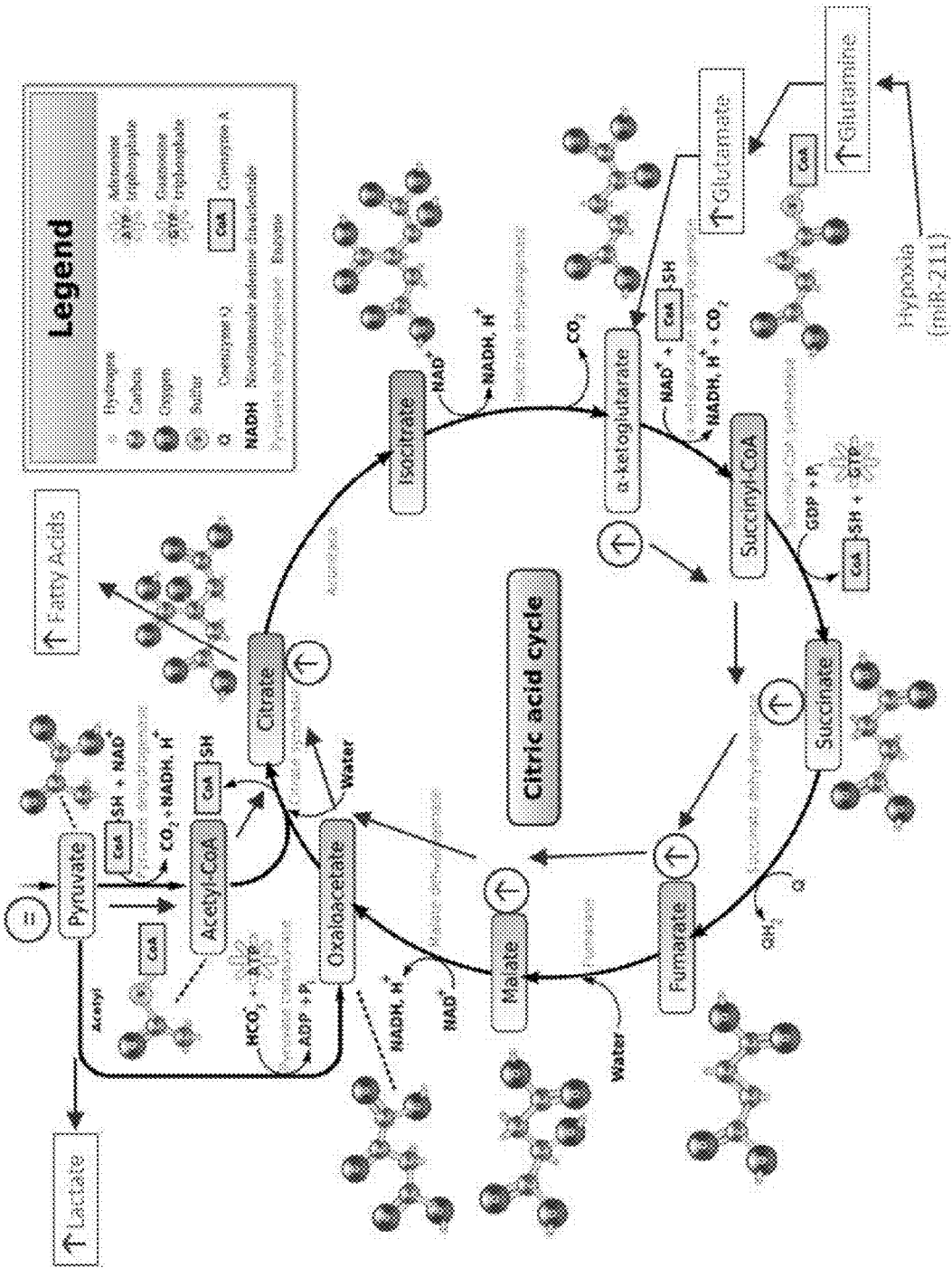
FIG. 33 is a schematic diagram of the citric acid cycle showing the changes in metabolites induced by expression of miR-211 in melanoma cells. Upregulation (indicated by vertical arrows) is an indication of active energy metabolism in miR-211-expressing cells.

To analyze the role of miR-211 in glucose and glutamine utilization, melanoma cells expressing miR-211 or empty vector were labeled with 13C-5-glutamine for 24 hours. Cells were then harvested and 13C-labeled metabolites were isolated and analyzed by mass spectrometry. Most of the 13C label recovered after 24 hr was in metabolites of the TCA cycle, demonstrating that glutamine metabolism contributes to oxidative ATP generation in these cells, as is the case with most actively proliferating cells in culture (FIG. 32). These results confirm that miR-211 has a direct effect on metabolite production in the TCA cycle. Further experiments will be performed at 48 and 72 hr to track 13C flux. The points at which miR-211 exhibits control over glycolysis and glutaminolysis will be determined using a dual strategy of stable isotope labeling. First, U-13C-glucose and use U-13C-glutamine will be used to create a broad map of metabolic activity, capturing information on glycolysis and lactate production, amino acid biosynthesis, TCA cycle flux, and fatty acid biosynthesis. Other 13C-glucose tracers will be used as needed to observe the metabolic flux of specific pathways. For example, using 1,2-13C-glucose the relative contribution of glycolysis and the pentose phosphate pathway (PPP) to the generation of ribose-5-phosphate and pyruvate will be determined. During the detection of the 13C isotopomer species, the metabolite pool sizes of ~20-40 metabolites will also be captured. By modeling the combination of 13C and pool size information for both the intracellular and extracellular (media) metabolomes the production or consumption rates of a number of metabolites will be determined. FIG. 33 provides an overview of the miR-211-induced changes in the TCA cycle.

In order to connect the metabolism to the bioenergentic status of melanoma cells, a number of metabolic parameters in melanoma cells expressing miR-211 or empty vector will be determined. The bioenergetic and redox status of the cells will be measured. Specifically, the glycolytic and respiration rates will be measured using a Seahorse XF analyzer, and ATP/ADP ratios will be determined using standard procedures. In addition a fluorescent assay will be used to determine the redox status of each cell line, as reflected in the NAD+/NADH ratio. These assays will allow a correlation of the bioenergetic and redox status of the cells to a particular metabolome and metabolic program.

Finally to confirm miR-211-influenced metabolic pathways through RNAi approaches, the functional significance of miR-211-stimulated metabolic pathways will be determined using two approaches. First, a targeted RNAi approach will be used to suppress key enzymes in metabolic pathways specifically activated in defined miR-211 genotypes. Care will be taken to identify all isoforms of each gene that may be active in human cells, and enzymes with redundant functions will be concurrently targeted. Knockdown will be confirmed by qPCR and western blot, and by secondary activity-based assays, as necessary. The effect of metabolic disruption on melanoma proliferation and survival will be determined using standard assays.

Example 17: Identification of Novel miR-211 Target and Regulatory Genes

Figure 34:
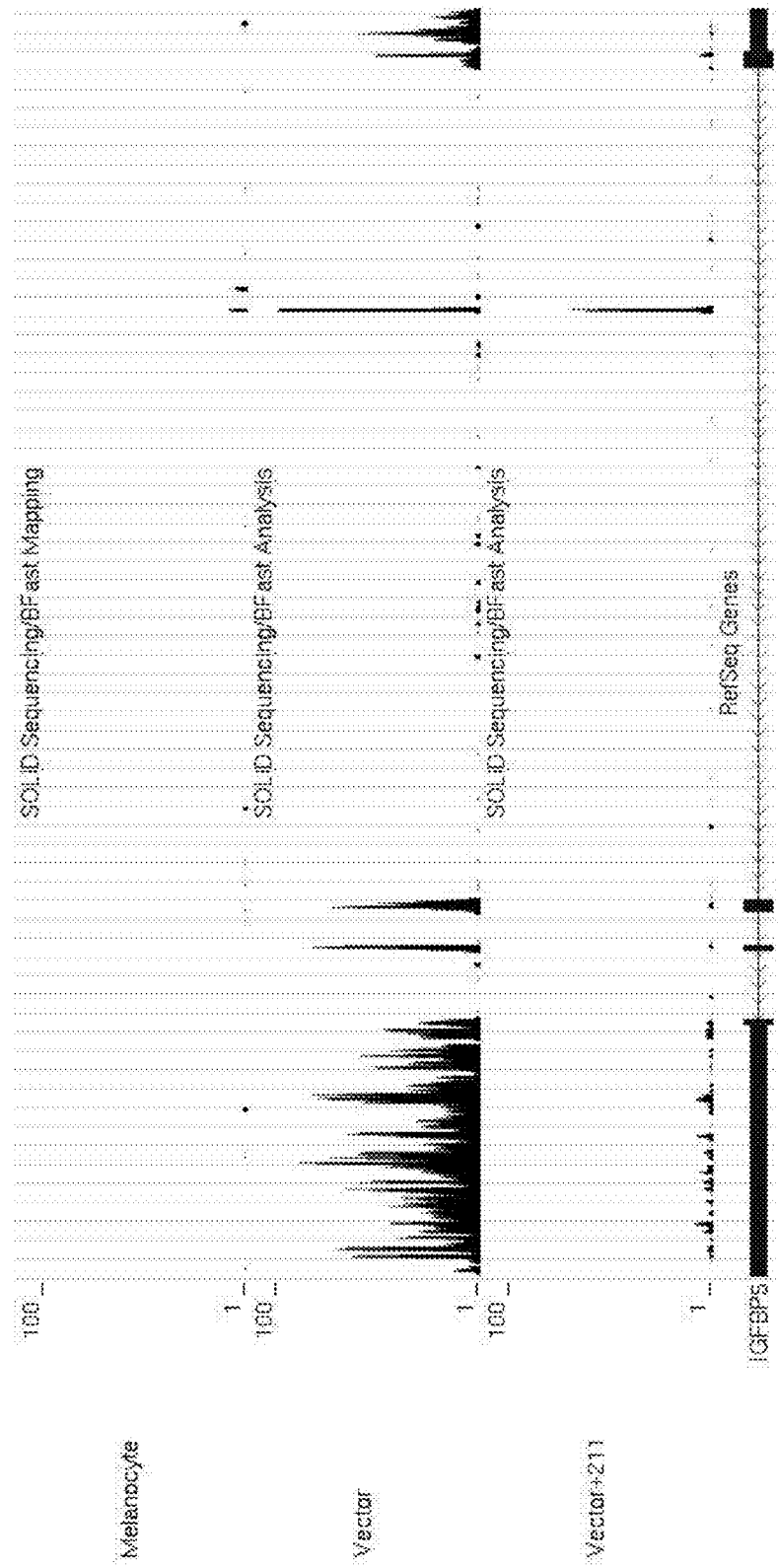
FIG. 34 is a graph showing the deep-sequencing results for melanocytes A375 transfected with empty vector (labelend Vector on the Y-axis) and A375 cells transfected with miR-211 (Vector+211). miR-211-expressing cells show reduced IGFBP5 expression compared with the vector-only cell line, demonstrating that IGFBP5 is a miR-211 target gene.

To identify global miR-211-induced changes in gene and protein expression, total RNA and total protein extracts were analyzed from parental and miR-211-expressing A375 and WM1552C cells by deep sequencing (RNA_seq) and Velos Orbitrap mass spectrometry, respectively. The initial data analysis will be done using the SOLiD 4.0 analyzer system for image acquisition, bead processing, quality assessment, and base calling. The reads will be aligned against the genome data using the Bowtie aligner with the criteria of allowing up to 3 mismatches within the 28 base seed. Only uniquely aligned reads will be collected and used for downstream data analyses. To obtain the differentially expressed genes, the read counts will be translated into gene-level expression. Since it was reported that the standard approach of scaling by global read count (such as RPKM) could bias estimates of differential expression, a general quantile-based approach will be applied for normalization in this study. To interpret the biological functions of the identified targets, the Ingenuity Pathway analysis (IPA) program will be applied for functional enrichment and network analyses. This tool will allow an in-depth and comprehensive pathway/network analysis for a list of interrelated biological data. Biological concept enrichment analysis will also be performed on the significant targets. University of California Santa Cruz (UCSC) genome browsers will be used for data visualization. All statistical analyses will be performed using the R/Bioconductor statistical environment. Finally, the results of this experiment will confirm association of miR-211 and its target genes to cell invasion, proliferation, and development in melanomas. An example of an identification of miR-211 target gene (IGFBP5) by RNA-seq results is depicted in FIG. 34 and target gene PDK4 is illustrated in FIG. 38.

Figure 35:
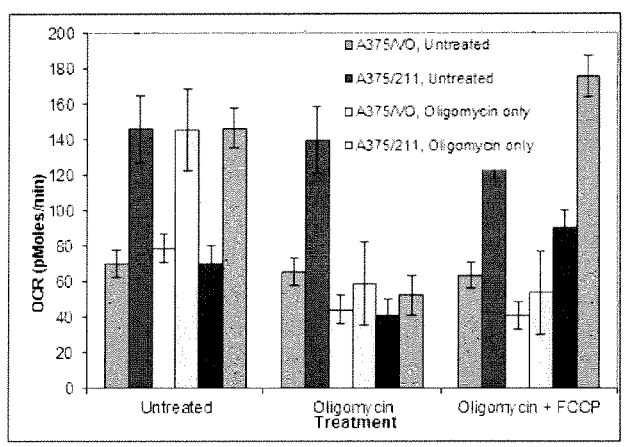
FIG. 35 is a bar graph showing oxygen consumption in A375 cells expressing miR-211 or empty vector. Oxygen consumption was measured using the Seahorse XF96 analyzer. A375 cells were untreated, treated with oligomycin to block consumption, or treated with oligomycin in the presence of FCCP, which releases the block in consumption.
Figure 36:
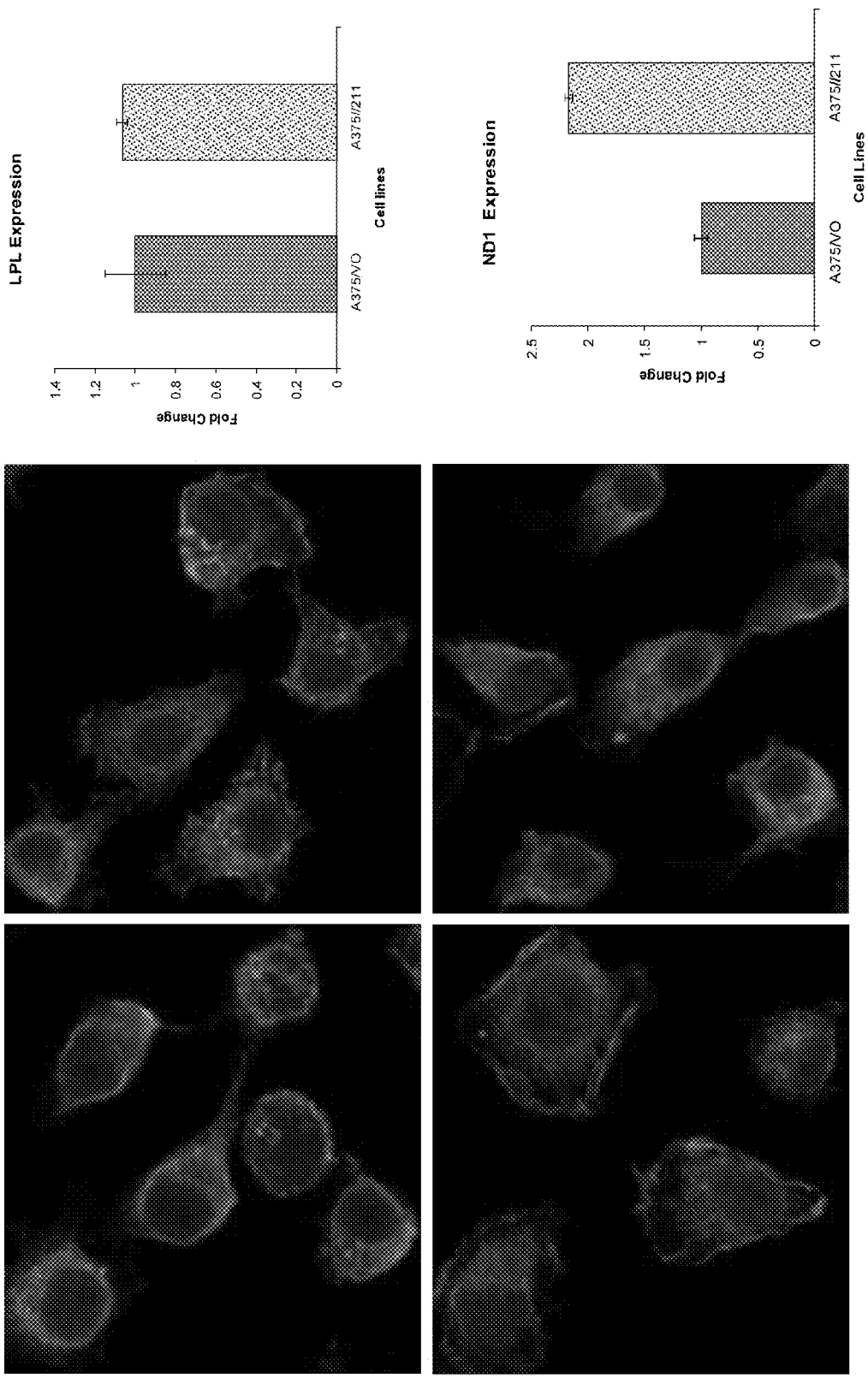
FIG. 36 is a set of photomicrographs and two bar graphs showing miR-211 expression as associated with increased numbers of mitochondria in A375 cells. Cells were transfected with miR-211 (bottom panels) or empty vector (top panels) and then stained with fluorescent markers to visualize mitochondria, cell wall, or nuclear DNA. Bar graphs show PCR of genomic DNA indicating that miR-211-transfected and control-transfected cells express an equivalent amount of LPL (upper graph), but miR-211-expressing cells express higher levels of the mitochondria-specific gene ND 1.
Figure 37:
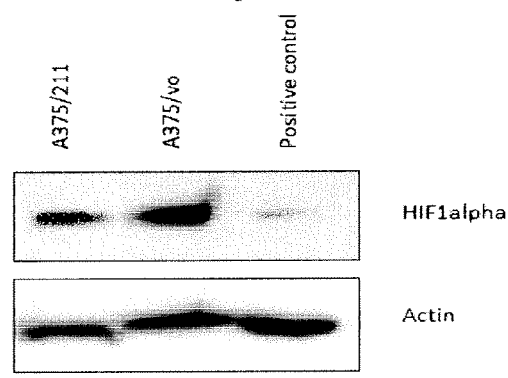
FIG. 37 is a gel showing reduced expression of HIF-1α in miR-211-expressing A375 cells.

Deep-sequencing (RNA-seq) and proteomics (mass spectrometry) data from two melanoma cell lines A375 and WM1552C, each expressing miR-211 or the empty vector, were generated. Several miR-211 target genes that are down-regulated and related to cellular metabolism were identified: pyruvate dehydrogenase kinase 4 (PDK4), pyruvate dehydrogenase kinase 1 (PDK1), peroxisome proliferator-activated receptor-γ coactivator (PGC1α), and insulin-like growth factor-binding protein 5 (IGFBP5). Energy consumption was investigated in miR-211-expressing cells. Using the Seahorse XF96 Analyzer, it was determined that miR-211-expressing melanoma cells (A375) consumed nearly double the amount of oxygen as control cells expressing the empty vector (FIG. 35). This result suggested that mitochondrial respiration was increased in miR-211-expressing cells. To probe this further, we analyzed the abundance of mitochondria in miR-211-expressing cells using MitoTracker, which showed that cells expressing miR-211 contained a higher number of mitochondria than did empty vector-expressing cells (FIG. 9). Finally, we measured the level of hypoxia-inducible factor 1 alpha (HIF-1α) in miR-211-expressing cells. HIF-1α expression was reduced by miR-211 expression which is an indication of cellular respiration changes (FIG. 37). Interestingly, when cells are treated with hypoxia mimetic agent deferoxomine (DFO-FDA approved drug), we observed increased cell death and we hypothesize that excessive hypoxia amplifies the miR-211 effects in melanoma cells. Though the underlying molecular mechanism of how miR-211 alters melanoma cell physiology is not clearly understood, these key results indicate that miR-211 may be an important regulator for melanoma development.

PDK4 is a primate specific miR-211 target gene according to the target scan database, and PDK4 expression was heavily downregulated in proteomics (mass spectrometric) data. This target was further confirmed by the cleavage assay, and the downregulation was verified by western blot analysis (FIG. 38). Similarly, peroxisome proliferator-activated receptor-γ coactivator (PGC1α) was identified by the proteomics data and validated by western blot analysis. PGC1α is a low express gene in A375 cells, but it is been targeted by miR-211 according to target cleavage and qPCR results. Finally, insulin-like growth factor-binding protein 5 (IGFBP5) was identified through the RNA-seq data and results are illustrated in FIG. 34.

Example 18: PDK-4, PGC1α, and IGFBP5 Influence Melanoma and Melanocyte Behavior

To determine how the miR-211 target genes PDK4, PGC1α, and IGFBP5 affect some critical processes in melanocyte transformation and melanoma cell behavior, two approaches are taken. In melanocytes and miR-211-expressing melanoma cells, these target genes are downregulated. To examine melanocytes, which express high levels of miR-211 and low levels of the target genes, a melanocyte cell line expressing a miR-211 sponge, which has been established at Sanford Burnham Medical Research Institute, is used. miRNA sponges are transcripts that are competitive antisense inhibitors expressed from strong promoters. These sponges contain multiple and tandem binding sites for miR-211. The cells will then be examined for PDK4, PGC1α, and IGFBP5 expression, which we expect to be increased. siRNA and shRNA for the knockdown experiments and cDNA expression constructs will be purchased from Open-Biosystems (https://www.openbiosystems.com). Each of the melanoma and melanocyte cell lines will be examined for the effects on cell behavior associated with tumorigenesis and energy metabolism: Cell invasion capacity will be assayed by standard methods using a modified Boyden chamber assay. Proliferation and cell viability will be assessed by two standard assays: MTT and the BrdU incorporation. Colony formation will be measured in vitro by soft agar assays. To examine apoptosis, three assays will be used. Cells will be assayed using a standard TUNEL [Terminal dUTP Nicked-End Labeling] assay. To examine necrosis, membrane permeability will be measured by the exclusion of trypan blue. Apoptosis will also be examined by annexin V staining and FACS analysis using an Annexin V-FITC Apoptosis Detection kit from BD Biosciences (San Jose, Calif.). Finally, apoptosis will be measured using an assay of caspase enzyme activation. Oxygen consumption and mitochondrial respiration will be measured using Seahorse XF96 Analyzer. The number of mitochondria will be measured using MitoTracker (Molecular Probes-Life Technologies). NADH and NADPH will be detected with the Omega High Speed, Full UV/Vis Absorbance Spectrometer (FLUOstar Omega machine). It is expected that changes in the cellular physiology and mitochondrial energy metabolism will be observed. Further, a knock-down or force-express HIF-1α in parental and miR-211 expressing cells will be created to monitor the oxygen consumption, numbers of mitochondria and NADH/NADPH ratio to associate miR-211 to hypoxia.

Example 19: Detection of miR-211 and Target Genes can Increase Accuracy of Early Melanoma Detection To examine expression of miR-211 and its target genes in melanoma patient samples, tissues will be obtained from James Goydos, M.D. (Director, The Melanoma and Soft Tissue Oncology Program, at the Robert Wood Johnson Medical School and Cancer Center, NJ) and Gregory Pennock, M.D. (Medical Oncologist, Section Leader, Melanoma & Sarcoma, Medical Director of Clinical Research Oncology, M.D. Anderson Cancer Center, Orlando). Although there is no perfect "normal" counterpart to melanoma in clinical skin samples, analysis of nevi should indicate the presence of miR-211 RNA in cells of the melanocytic lineage. Therefore, nevi and normal skin samples will serve as controls. miR-211 and its target genes will be measured by qPCR and northern blotting on tissue samples from different stages of melanoma (primary in situ, regional metastatic, nodular metastatic, and distant metastatic melanoma). Gene expression levels will then be correlated with patient group disease characteristics and the pathologically defined disease stage. Laser-capture microdissection (LCM) will be performed on some samples at the Sanford-Burnham Institute's Histology Core laboratory. LCM tissues will be characterized based on immunohistochemical staining of key markers (S100, Mart1, Tyrosinase, and Ki-67).

Based on preliminary qPCR results, the sample size required to obtain biologically (FC>=2) and statistically significant results for the primary in situ, regional metastatic, nodular metastatic, and distant metastatic melanomas, normal skin, and melanocytic nevi was calculated at power of 0.8 and p-value of 0.05. The calculated sample sizes are: (a) for nodal metastatic vs melanocytic nevi, 18/group; for normal skin vs melanocytic nevi, 11/group; for distant metastatic vs melanocytic nevi, 109/group. These power calculations were performed using preliminary data for miR-211 expression, but additional calculations will be performed once we have data on target gene expression in patient samples. Sample size calculations were performed using R with sizepower package and R bioconductor software using the t-test procedure.

Univariate and multivariate logistic regressions will be used to examine associations between the expression of miR-211 and target genes, and melanoma disease stage, as well as clinical variables such as age and gender. For multivariate logistic regression, the Akaike information criterion (AIC)-based backward selection will be used to drop insignificant variables. After the final model is determined, the predicted probability (TPR & FPR) will be used as input to generate the receiver-operating characteristic (ROC) curve, which will then be used to find potential biomarkers that can discriminate melanoma patients from normal controls. The hierarchical clustering method implemented in GenePattern and a leave-one-out cross-validation (LOOCV) will be used on the multiple identified biomarkers to distinguish cases from controls. If survival data is available, log-rank test, Kaplan-Meier analysis, and Cox proportional hazard regression analysis will be used to identify associations between clinical variables, potential melanoma biomarkers, and survival. All analyses will be performed with R or SAS software.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for detecting and treating melanoma in a human subject comprising:
   (a) detecting melanoma in a skin sample from the human subject, wherein detecting comprises:
      (i) detecting the expression level of human potassium channel, calcium activated large conductance subfamily M alpha, member 1 (KCNMA1) in the skin sample; and
      (ii) detecting the melanoma when the expression level of KCNMA1 in the skin sample is greater than a reference expression level from a control sample; and
   (b) administering to the human subject an effective amount of a nucleic acid encoding miR-211.

2. The method of claim 1, wherein the control sample is from a human subject known not to have melanoma or is a normal melanocyte sample.

3. The method of claim 1, wherein the biological sample comprises skin epidermis or melanocytes.

4. The method according to claim 1, wherein administering the nucleic acid encoding miR-211 reduces expression of KCNMA1 in the subject.

5. The method according to claim 4, wherein reducing KCNMA1 expression inhibits melanoma cell invasion.

6. The method according to claim 1, wherein detecting the expression level of KCNMA1 expression level comprises quantifying KCNMA1 mRNA by reverse transcriptase PCR (RT-PCR) or hybridizing KCNMA1 mRNA in the biological sample to a nucleic acid array.

7. The method of claim 1, wherein the nucleic acid encoding miR-211 is contained in a vector.

8. The method of claim 1, wherein the nucleic acid encoding miR-211 is contained within a liposome.

* * * * *